(12) United States Patent
An

(10) Patent No.: US 10,660,889 B2
(45) Date of Patent: *May 26, 2020

(54) COMPOUNDS FOR TREATMENT OF CANCER

(71) Applicant: Curegenix, Inc., Guangzhou (CN)

(72) Inventor: Songzhu An, Foster City, CA (US)

(73) Assignee: Curegenix, Inc., Guangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/261,353

(22) Filed: Jan. 29, 2019

(65) Prior Publication Data

US 2019/0142827 A1    May 16, 2019

Related U.S. Application Data

(63) Continuation of application No. 15/617,988, filed on Jun. 8, 2017, now Pat. No. 10,238,652, which is a continuation of application No. 14/772,337, filed as application No. PCT/US2014/024885 on Mar. 12, 2014, now Pat. No. 9,713,612.

(60) Provisional application No. 61/777,427, filed on Mar. 12, 2013.

(51) Int. Cl.

| | | |
|---|---|---|
| *A61K 31/4985* | (2006.01) | |
| *A61K 31/4375* | (2006.01) | |
| *A61K 31/495* | (2006.01) | |
| *A61K 31/444* | (2006.01) | |
| *A61K 31/472* | (2006.01) | |
| *A61K 31/4725* | (2006.01) | |
| *A61K 31/496* | (2006.01) | |
| *A61K 31/501* | (2006.01) | |
| *A61K 31/506* | (2006.01) | |
| *A61K 31/5377* | (2006.01) | |
| *A61K 31/541* | (2006.01) | |
| *A61K 31/497* | (2006.01) | |
| *A61K 31/519* | (2006.01) | |
| *A61K 31/5025* | (2006.01) | |

(52) U.S. Cl.
CPC ...... *A61K 31/4985* (2013.01); *A61K 31/4375* (2013.01); *A61K 31/444* (2013.01); *A61K 31/472* (2013.01); *A61K 31/4725* (2013.01); *A61K 31/496* (2013.01); *A61K 31/497* (2013.01); *A61K 31/501* (2013.01); *A61K 31/506* (2013.01); *A61K 31/5377* (2013.01); *A61K 31/541* (2013.01); *A61K 31/5025* (2013.01); *A61K 31/519* (2013.01)

(58) Field of Classification Search
CPC .... A61K 31/4985; A61K 31/43; A61K 31/75; A61K 31/495
See application file for complete search history.

(56) References Cited

U.S. PATENT DOCUMENTS

| | | |
|---|---|---|
| 9,556,144 B2 | 1/2017 | An |
| 9,713,612 B2 | 7/2017 | An |
| 10,087,181 B2 | 10/2018 | An |
| 10,238,652 B2 | 3/2019 | An |
| 2009/0004185 A1 | 1/2009 | Venkatesan et al. |
| 2009/0069338 A1 | 3/2009 | Dickson, Jr. et al. |
| 2011/0237573 A1 | 9/2011 | Cheng et al. |
| 2012/0196916 A1 | 8/2012 | deLong et al. |
| 2012/0270858 A1 | 10/2012 | Tao et al. |
| 2018/0112273 A1 | 4/2018 | Qin et al. |

FOREIGN PATENT DOCUMENTS

| | | |
|---|---|---|
| CN | 102558173 B | 5/2015 |
| WO | 2004/043925 A2 | 5/2004 |
| WO | 2005/040418 A2 | 5/2005 |
| WO | 2006/074428 A2 | 7/2006 |
| WO | 2013130364 A1 | 9/2013 |
| WO | 2013/185353 A1 | 12/2013 |

OTHER PUBLICATIONS

Songzhu, A. et al. CN 102558173—Translated chinese document per WIPO.*
Seshagiri et al. Nature, 2012, vol. 486, pp. 600-663.*
Seshagiri, et al. "Recurrent R-spondin fusions in colon cancer", Nature 488: 660-663, Aug. 30, 2012.
International Search Report, dated Jul. 11, 2014.
Supplementary European Search Report dated Oct. 12, 2016 for European Patent Application No. 14778108.2 filed on Mar. 12, 2014.
Niehrs, C. The complex world of WNT receptor signaling. Nature Reviews Molecular Cell Biology, vol. 13, pp. 767-779 (2012).
Holland et al., Wnt signaling in stem and cancer stem cells. Current Opinion in Cell Biology, vol. 25, No. 2, pp. 254-264 (2013).
Extended European Search Report for EP16800691 (PCT/US2016/034245), dated Dec. 11, 2018.
Liu et al. Targeting Wnt-driven cancer through inhibition of Porcupine by LGK974. Proc. Natl. Acad Sci. USA 110 (50):20224-20229 (2013).

* cited by examiner

*Primary Examiner* — Samira J Jean-Louis

(74) *Attorney, Agent, or Firm* — K&L Gates LLP; Louis C. Cullman; David Diamond

(57) ABSTRACT

The present invention relates to compounds as inhibitor of WNT signal transduction pathway, as well as a composition comprising the same. Further, the present invention relates to the use of the compounds in the treatment of cancer.

11 Claims, 9 Drawing Sheets

Specification includes a Sequence Listing.

Sequence of PCR product of Colorectal Tumor Model #1 with PTPRK (e1) – Rspo3 (e2) fusion (SEQ ID NO:17; 226bps):

<u>AAACTCGGCATGGATACGACTGCGGCGGCGGCGCTGCCTGCTTTTGTGGCGCTCTTGCTCCTCTCTCCTT</u>
GGCCTCTCCTGGGATCGGCCCAAGGCCAGTTCTCCGCAGtgcatcctaacgttagtcaaggctgccaagg
aggctgtgcaacatgctcagattacaatggatgtttgtcatgtaagcccagactattttt<u>tgctctggaa
agaattggcatgaagc</u>

Annotation: underlined: primers; capital letters: PTPRK sequence; lower case letters: Rspo3 sequence

FIG. 3

Sequence of PCR Product of Colorectal Tumor Model #5 with PTPRK (e7) -Rspo3 (e2) fusion (SEQ ID NO:18; 257bps):

<u>TGCAGTCAATGCTCCAACTTACAAATTATG</u>GCATTTAGATCCAGATACCGAATATGAGATCCGAGTTCTA
CTTACAAGACCTGGTGAAGGTGGAACGGGGCTCCCAGGACCTCCACTAATCACCAGAACAAAATGTGCAG
tgcatcctaacgttagtcaaggctgccaaggaggctgtgcaacatgctcagattacaatggatgtttgtc
atgtaagcccagactatttt<u>ttgctctggaaagaattggcatgaagc</u>

Annotation: underlined: primers; capital letters: PTPRK sequence; lower case letters: Rspo3 sequence

FIG. 4.

Sequence of the Rspo3-PTPRK Fusion from Gastric and Liver Tumor Models (PCR Product of 226 bp; SEQ ID NO:19):

RT-PCR product of gastric tumor model #G10 and liver tumor model #L2 and #L8 with gene fusion between PTPRK and Rspo3. Sequencing data show that these tumors have fusion between exon 1 of PTPRK to exon 2 of Rspo3.

<u>AAACTCGGCATGGATACGAC</u>TGCGGCGGCGGCGCTGCCTGCTTTTGTGGCGCTCTTGCTCCTCTCTCCTT
GGCCTCTCCTGGGATCGGCCCAAGGCCAGTTCTCCGCAGtgcatcctaacgttagtcaaggctgccaagg
aggctgtgcaacatgctcagattacaatggatgtttgtcatgtaagcccagactatttt<u>tgctctggaa
agaattggcatgaagc</u>

Annotation: underlined: primers; capital letters: PTPRK sequence; lower case letters: Rspo3 sequence

FIG. 6

Sequence of the Rspo3-PTPRK Fusion from an Esophageal Tumor Model (PCR Product of 257 bp; SEQ ID NO:20):

RT-PCR product of esophageal tumor model #E7 with gene fusion between PTPRK and Rspo3. Sequencing data show that this tumor has fusion between exon 7 of PTPRK and exon 2 of Rspo3.

<u>TGCAGTCAATGCTCCAACTTACAAATTATG</u>GCATTTAGATCCAGATACCGAATATGAGATCCGAGTTCTA
CTTACAAGACCTGGTGAAGGTGGAACGGGGCTCCCAGGACCTCCACTAATCACCAGAACAAAATGTGCAG
tgcatcctaacgttagtcaaggctgccaaggaggctgtgcaacatgctcagattacaatggatgtttgtc
atgtaagcccagactattt<u>ttgctctggaaagaattggcatgaagc</u>

Annotation: underlined: primers; capital letters: PTPRK sequence; lower case letters: Rspo3 sequence

FIG. 7

Sequence of the Rspo2-EIFE3 Fusion from Liver Tumor Model (PCR product of 155 bp; SEQ ID NO:21):

RT-PCR product of liver tumor model #L7 with gene fusion between exon 1 of EIF3E and exon 2 of Rspo2.

<u>ACTACTCGCATCGCGCACTTTT</u>TGGATCGGCATCTAGTCTTTCCGCTTCTTGAATTTCTCTCTGT
AAAGGAGgttcgtggcggagagatgctgatcgcgctgaactgaccggtgcggcccgggggtgagt
ggcga<u>gtctccctctgagtcctccc</u>

Annotation: underlined: primers; capital letters: EIFE3 sequence; lower case letters: Rspo2 sequence

FIG. 8

Sequence of the Rspo2-EIFE3 Fusion from Gastric and Liver Tumor Models (PCR product of 205 bp; SEQ ID NO:22):

RT-PCR product of gastric tumor models #G6 and #G13 and liver tumor model #L6 with gene fusion between exon 1 of EIF3E and exon 3 of Rspo2.

<u>ACTACTCGCATCGCGCACTTTT</u>TGGATCGGCATCTAGTCTTTCCGCTTCTTGAATTTCTCTCTGT AAAGGAGctagttatgtatcaaatcccatttgcaagggttgtttgtcttgttcaaaggacaatgg gtgtagccgatgtcaacagaagttgttcttcttccttcgaagagaagggatgcgc<u>cagtatggag agtgcctgca</u>

Annotation: underlined: primers; capital letters: EIFE3 sequence; lower case letters: Rspo2 sequence

FIG. 9

COMPOUNDS FOR TREATMENT OF CANCER

CROSS REFERENCE TO RELATED APPLICATIONS

This application is the continuation of U.S. patent application Ser. No. 15/617,988, now U.S. Pat. No. 10,238,652, which is the continuation of U.S. patent application Ser. No. 14/772,337, filed Sep. 2, 2015, now U.S. Pat. No. 9,713,612, which is the U.S. national phase of international application no. PCT/US2014/024885, filed Mar. 12, 2014, which claims the benefit of, and priority to, U.S. Provisional Patent Application Ser. No. 61/777,427, filed on Mar. 12, 2013. The entire disclosures of all these applications are hereby incorporated by references in their entireties.

FIELD OF THE INVENTION

The present invention relates to compounds as inhibitor of WNT signal transduction pathway, as well as compositions comprising the same. Further, the present invention relates to the use of the compounds in the treatment of cancer.

BACKGROUND OF THE INVENTION

Cancer is a class of diseases that affects people worldwide. Generally, cells in a benign tumor retain their differentiated features and do not divide in a completely uncontrolled manner. A benign tumor is usually localized and non-metastatic.

In a malignant tumor, cells become undifferentiated, do not respond to the body's growth control signals, and multiply in an uncontrolled manner. Malignant tumors are generally divided into two categories: primary and secondary. Primary tumors arise directly from the tissue in which they are found. Secondary tumors may be originated from the primary tumors or may be originated elsewhere in the body, and are capable of spreading to distant sites (metastasizing) or metastasis. The common routes for metastasis are direct growth into adjacent structures, spread through the vascular or lymphatic systems or blood streams.

WNT signaling is important to both embryogenesis and homeostasis in adult animals. The WNT pathway is comprised in general of a network of proteins that regulate the following processes: 1, the production and secretion of WNT proteins; 2, the binding of WNT with cellular receptors; and 3, the intracellular transduction of the biochemical responses triggered by the interaction (Mikels and Nusse, 2006; MacDonald, 2009; Moon, 2005).

The so-called canonical WNT pathway triggered by binding of WNT proteins to cell surface co-receptors Frizzled LRP5/6 results in a change in the amount of R-catenin that reaches the nucleus where it interacts with TCF/LEF family transcription factors to promote transcription of specific genes.

The non-canonical WNT pathway transduced by a different set of intracellular proteins controls planar cell polarity in insects and several processes such as gastrulation in vertebrates.

WNT signaling is also known for its roles in controlling pluripotency and differentiation of embryonic and adult stem cells (Nusse, 2008). For example, formation of the primitive streak during gastrulation was associated with localized WNT activation in the embryoid bodies (Ten Berge, 2008). The derivation of a number of cell types, such as heart cells, pancreatic beta cells, dopminergic neurons and liver hepatocytes from embryonic stem cells or iPS cells is influenced by WNT modulation (Yang, 2008; D'Amour, 2006; Inestrosa and Arenas, 2010; Sullivan, 2010). The WNT pathway plays a particularly important role in skeletal tissue development such as osteogenesis and chondrogenesis (Hoeppner, 2009; Chun, 2008). WNT signaling is also associated with neuro-regeneration of the adult central nervous system (Lie, 2005).

Diseases may arise from altered WNT pathway activity. For example, hyperactivation of the canonical WNT pathway can lead to aberrant cell growth (Reya and Clevers, 2005). Notably, 90% of colorectal cancers are initiated by the loss of the adenomatosis polyposis *coli* (APC) gene, a suppressor of the WNT/β-catenin pathway (Kinzler and Vogelstein, 1996). Increased expression of WNT proteins and loss of extracellular inhibitors that normally suppress WNT protein function may give rise to WNT-dependent tumors (Polakis, 2007). On the other hand, the non-canonical WNT pathway has also been shown to play a role in the progression of certain cancers (Camilli and Weeraratna, 2010). More recently, WNT signaling is also implicated in cancer stem cells (Takahashi-Yanaga and Kahn, 2010).

Evidence suggests that targeting the Wnt-mediated signal transduction pathway would be therapeutically useful in a broad range of diseases (Barker and Clevers, 2006). Mutations of APC, beta-catenin or axin-1 leading to constitutive activation of the canonical Wnt pathway are critical events in a variety of human cancers including colorectal cancer, melanoma, hepatocellular carcinoma, gastric cancer, ovarian cancer and others (Polakis, 2007). Blockade of the Wnt pathway in a variety of cancers using either genetic or chemical approaches has been shown to abrogate aberrant cell growth (Herbst and Kolligs, 2007). Furthermore, inhibition of this pathway may directly influence the cells that sustain cancer cell growth and enable metastasis, and that are thought to be resistant to traditional chemotherapeutic agents.

In addition to activation caused by mutations of gene products downstream of the receptors, aberrant Wnt pathway activity caused by other mechanisms have been associated with a broad range of cancers. These cancers include but not limited to: lung (small cell and non-small cell), breast, prostate, carcinoid, bladder, scarcinoma, esophageal, ovarian, cervical, endometrial, mesothelioma, melanoma, sarcoma, osteosarcoma, liposarcoma, thyroid, desmoids, chronic myelocytic leukemia (AML), and chronic myelocytic leukemia (CML). There are now multiple examples of cancer cells dependent upon upregulated autocrine or paracrine Wnt signaling, and cell lines from osteosarcoma, breast, head and neck and ovarian cancers have been shown to derive protection from apoptosis by autocrine or paracrine Wnt signaling (Kansara, 2009; Bafico, 2004; Akiri, 2009; DeAlmeida, 2007; Chan, 2007; Chen, 2009; Rhee, 2002).

Furthermore, aberrant Wnt pathway has been implicated in the development of fibrosis, include but are not limited to: lung fibrosis, such as idiopathic pulmonary fibrosis and radiation-induced fibrosis, renal fibrosis and liver fibrosis (Morrisey, 2003; Hwang, 2009; Cheng, 2008).

Other disorders associated with aberrant WNT signaling, include but are not limited to bone and cartilage disorders, such as osteoporosis and osteoarthritis, obesity associated type II diabetes, and neurodegenerative diseases such as Alzheimer's disease (Hoeppner, 2009; Ouchi, 2010; Blom, 2010; Boonen, 2009). WNT signaling also contributes to the self-renewal and maintenance of HSC's, and dysfunctional WNT signaling is responsible for various disorders resulting from HSC's, such as leukemias and various other blood related cancers (Reya, 2005).

Accordingly, identification of methods and compounds that modulate the WNT-dependent cellular responses may offer an avenue for regulating physiological functions and therapeutic treatment of diseases associated with aberrant activity of the pathways.

SUMMARY OF THE INVENTION

The present invention generally provides a compound and a pharmaceutical composition thereof, while the compound is used as WNT signaling inhibitor, and the use of such compound for treatment of diseases, such as cancer.

In one aspect, the present invention provides a method for treating cancer characterized by R-spondin overexpression and/or expression of an R-spondin fusion in a subject that has been diagnosed as having R-spondin overexpression and/or an R-spondin fusion and is in need of such treatment, comprising administering to the subject a pharmaceutical composition comprising a therapeutically effective amount of a compound of the following formula:

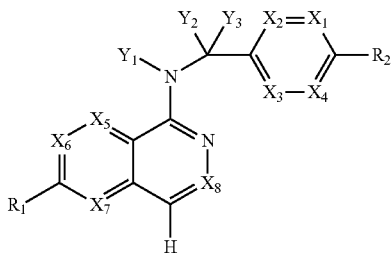

or a physiologically acceptable salt thereof, wherein
$X_1, X_2, X_3, X_4, X_5, X_6, X_7, X_8$ are independently $CR_4$ or N;
$Y_1$ is hydrogen or $CR_4$; $Y_2, Y_3$ are independently hydrogen, halo or $CR_3$;
$R_1$ is morpholinyl, piperazinyl, quinolinyl,

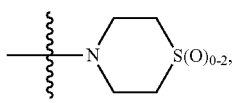

aryl, $C_{1-6}$ heterocycle, 5 or 6 membered heteroaryl containing 1-2 heteroatoms selected from N, O and S;
$R_2$ is hydrogen, halo, morpholinyl, piperazinyl, quinolinyl,

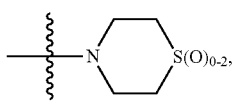

aryl, $C_{1-6}$ heterocycle, 5 or 6 membered heteroaryl containing 1-2 heteroatoms selected from N, O and S; $R_3$ is hydrogen, halo, cyano, $C_{1-6}$ alkyl, $C_{1-6}$ alkoxy optionally substituted with halo, amino, hydroxyl, alkoxy or cyano;
$R_4$ is hydrogen, halo, $C_{1-6}$alkoxy, $-S(O)_2R_5$, $-C(O)OR_5$, $-C(O)R_5$, $-C(O)NR_6R_7$, $C_{1-6}$ alkyl, $C_{2-6}$ alkenyl or $C_{2-6}$ alkynyl, each of which can be optionally substituted with halo, amino, hydroxyl, alkoxy or cyano;
$R_5, R_6$ and $R_7$ are independently hydrogen, $C_{1-6}$ alkyl, $C_{2-6}$ alkenyl or $C_{2-6}$ alkynyl, each of which may be optionally substituted with halo, amino, hydroxyl, alkoxy or cyano.

In some embodiments, the 5 or 6 membered heteroaryl is selected from:

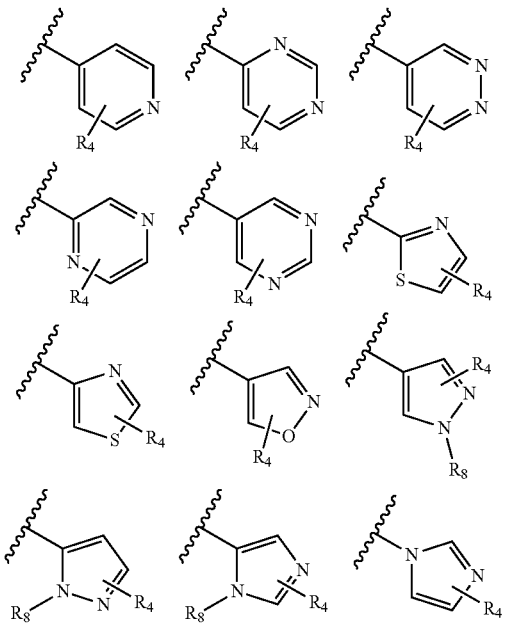

wherein,
$R_4$ is hydrogen, halo, $C_{1-6}$alkoxy, $-S(O)_2R_5$, $-C(O)OR_5$, $-C(O)R_5$, $-C(O)NR_6R_7$, $C_{1-6}$ alkyl, $C_{2-6}$ alkenyl or $C_{2-6}$ alkynyl, each of which can be optionally substituted with halo, amino, hydroxyl, alkoxy or cyano;
$R_5, R_6$ and $R_7$ are independently hydrogen, $C_{1-6}$ alkyl, $C_{2-6}$ alkenyl or $C_{2-6}$ alkynyl, each of which may be optionally substituted with halo, amino, hydroxyl, alkoxy or cyano; and
$R_8$ is hydrogen or $C_{1-6}$ alkyl.

In some embodiments, $R_1$ and $R_2$ is independently substituted with 1 or 2 $R_4$ groups.

In some embodiments, the atom in any the substituent groups is H, $^2$H, $^3$H, $^{11}$C, $^{13}$C, $^{14}$C $^{15}$N, $^{17}$O, $^{18}$O, $^{35}$S, $^{18}$F, $^{36}$I and/or $^{123}$I.

In some embodiments, the compound is selected from
N-((6-(2-methylpyridin-4-yl)pyridin-3-yl)methyl)-7-phenylquinazolin-4-amine;
N-((5-(2-methylpyridin-4-yl)pyridin-2-yl)methyl)-7-phenylquinazolin-4-amine;
N-(4-morpholinobenzyl)-7-phenylquinazolin-4-amine;
N-((6-morpholinopyridin-3-yl)methyl)-7-phenylquinazolin-4-amine;
N-((6-(2-methylmorpholino)pyridin-3-yl)methyl)-7-phenylquinazolin-4-amine;
N-((6-(4-methyl piperazin-1-yl)pyridin-3-yl)methyl)-7-phenylquinazolin-4-amine;
4-(5-(((7-phenylquinazolin-4-yl)amino)methyl)pyridin-2-yl)thiomorpholine 1,1-dioxide;
N-((6-(6-methylpyridin-3-yl)pyridin-3-yl)methyl)-7-phenylquinazolin-4-amine;
N-((6-(5-methylpyridin-3-yl)pyridin-3-yl)methyl)-7-phenylquinazolin-4-amine;
7-phenyl-N-((6-(pyridin-4-yl)pyridin-3-yl)methyl)quinazolin-4-amine;
7-phenyl-N-((6-(pyridin-3-yl)pyridin-3-yl)methyl)quinazolin-4-amine;
7-phenyl-N-((6-(pyridin-2-yl)pyridin-3-yl)methyl)quinazolin-4-amine;

7-phenyl-N-((6-(pyridazin-4-yl)pyridin-3-yl)methyl)quinazolin-4-amine;
7-phenyl-N-((6-(pyrazin-2-yl)pyridin-3-yl)methyl)quinazolin-4-amine;
7-phenyl-N-((6-(pyrimidin-5-yl)pyridin-3-yl)methyl)quinazolin-4-amine;
N-((6-(2-fluoropyridin-4-yl)pyridin-3-yl)methyl)-7-phenylquinazolin-4-amine;
N-((6-(4-methyl-1H-imidazol-1-yl)pyridin-3-yl)methyl)-7-phenylquinazolin-4-amine;
N-((6-(1-methyl-1H-pyrazol-4-yl)pyridin-3-yl)methyl)-7-phenylquinazolin-4-amine;
N-((5-(6-methylpyridin-3-yl)pyridin-2-yl)methyl)-7-phenylquinazolin-4-amine;
N-(4-(2-methylpyridin-4-yl)benzyl)-7-phenylquinazolin-4-amine;
N-(4-(2-fluoropyridin-4-yl)benzyl)-7-phenylquinazolin-4-amine;
N-benzyl-7-(2-methylpyridin-4-yl)quinazolin-4-amine;
N-(4-methylbenzyl)-7-(2-methylpyridin-4-yl)quinazolin-4-amine;
N-(4-methoxybenzyl)-7-(2-methylpyridin-4-yl)quinazolin-4-amine;
N-(4-fluorobenzyl)-7-(2-methylpyridin-4-yl)quinazolin-4-amine;
N-(4-chlorobenzyl)-7-(2-methylpyridin-4-yl)quinazolin-4-amine;
N-(4-bromobenzyl)-7-(2-methylpyridin-4-yl)quinazolin-4-amine;
N-(4-(trifluoromethyl)benzyl)-7-(2-methylpyridin-4-yl)quinazolin-4-amine;
4-((7-(2-methylpyridin-4-yl)quinazolin-4-ylamino)methyl)benzonitrile; N-(4-morpholinobenzyl)-7-(2-methylpyridin-4-yl)quinazolin-4-amine;
N-(4-phenylbenzyl)-7-(2-methylpyridin-4-yl)quinazolin-4-amine;
N-(3-fluoro-4-phenylbenzyl)-7-(2-methylpyridin-4-yl)quinazolin-4-amine;
N-(4-(3-fluorophenyl)benzyl)-7-(2-methylpyridin-4-yl)quinazolin-4-amine;
7-(3-fluorophenyl)-N-((6-(2-methylpyridin-4-yl)pyridin-3-yl)methyl)quinazolin-4-amine;
7-(3-chlorophenyl)-N-((6-(2-methylpyridin-4-yl)pyridin-3-yl)methyl)quinazolin-4-amine;
N-((6-(2-methylpyridin-4-yl)pyridin-3-yl)methyl)-7-m-tolylquinazolin-4-amine;
3-(4-((6-(2-methylpyridin-4-yl)pyridin-3-yl)methylamino)quinazolin-7-yl)benzonitrile;
4-(4-((6-(2-methylpyridin-4-yl)pyridin-3-yl)methylamino)quinazolin-7-yl)benzonitrile;
7-(2-methyl pyridin-4-yl)-N-((6-(2-methylpyridin-4-yl)pyridin-3-yl)methyl)quinazolin-4-amine;
7-(6-methyl pyridin-3-yl)-N-((6-(2-methylpyridin-4-yl)pyridin-3-yl)methyl)quinazolin-4-amine;
7-(5-methyl pyridin-3-yl)-N-((6-(2-methylpyridin-4-yl)pyridin-3-yl)methyl)quinazolin-4-amine;
N-((6-(2-methylpyridin-4-yl)pyridin-3-yl)methyl)-7-(pyridin-2-yl)quinazolin-4-amine;
N-((6-(2-methylpyridin-4-yl)pyridin-3-yl)methyl)-7-(pyridin-3-yl)quinazolin-4-amine;
N-((6-(2-methylpyridin-4-yl)pyridin-3-yl)methyl)-7-(pyridin-4-yl)quinazolin-4-amine;
N-((6-(2-methyl pyridin-4-yl)pyridin-3-yl)methyl)-7-(pyridazin-4-yl)quinazolin-4-amine;
N-((6-(2-methyl pyridin-4-yl)pyridin-3-yl)methyl)-7-(pyrazin-2-yl)quinazolin-4-amine;
N-((6-(2-methylpyridin-4-yl)pyridin-3-yl)methyl)-7-(pyrimidin-5-yl)quinazolin-4-amine;
7-(2-fluoropyridin-4-yl)-N-((6-(2-methylpyridin-4-yl)pyridin-3-yl)methyl)quinazolin-4-amine;
7-(2-(trifluoromethyl)pyridin-4-yl)-N-((6-(2-methylpyridin-4-yl)pyridin-3-yl)methyl)quinazolin-4-amine;
7-(2-methoxypyridin-4-yl)-N-((6-(2-methylpyridin-4-yl)pyridin-3-yl)methyl)quinazolin-4-amine;
7-(3-methyl pyridin-4-yl)-N-((6-(2-methylpyridin-4-yl)pyridin-3-yl)methyl)quinazolin-4-amine;
N-((6-(2-methylpyridin-4-yl)pyridin-3-yl)methyl)-7-morpholinoquinazolin-4-amine;
N-((6-(2-methylpyridin-4-yl)pyridin-3-yl)methyl)-7-(piperidin-1-yl)quinazolin-4-amine;
7-(4-methylpiperazin-1-yl)-N-((6-(2-methylpyridin-4-yl)pyridin-3-yl)methyl)quinazolin-4-amine;
1-(4-(4-((6-(2-methylpyridin-4-yl)pyridin-3-yl)methylamino)quinazolin-7-yl) piperazin-1-yl)ethanone;
4-(4-(((2'-methyl-[2,4'-bipyridin]-5-yl)methyl)amino)quinazolin-7-yl)thiomorpholine 1,1-dioxide;
7-(1,2,3,6-tetrahydropyridin-4-yl)-N-((6-(2-methylpyridin-4-yl)pyridin-3-yl)methyl)quinazolin-4-amine;
7-(1,2,3,6-tetrahydropyridin-4-yl)-N-((6-(2-methylpyridin-4-yl)pyridin-3-yl)methyl)quinazolin-4-amine;
1-(4-(4-((6-(2-methylpyridin-4-yl)pyridin-3-yl)methylamino)quinazolin-7-yl)piperidin-1-yl)ethanone;
N-((2'-methyl-[2,4'-bipyridin]-5-yl)methyl)-7-(4-(methylsulfonyl)piperazin-1-yl)quinazolin-4-amine;
7-(1-methyl-1H-pyrazol-4-yl)-N-((6-(2-methylpyridin-4-yl)pyridin-3-yl)methyl)quinazolin-4-amine;
7-(isoxazol-4-yl)-N-((6-(2-methylpyridin-4-yl)pyridin-3-yl)methyl)quinazolin-4-amine;
N-((6-(2-methylpyridin-4-yl)pyridin-3-yl)methyl)-7-(thiazol-2-yl)quinazolin-4-amine;
N-(3-methyl-4-(2-methylpyridin-4-yl)benzyl)-7-(2-methylpyridin-4-yl)quinazolin-4-amine;
N-(3-fluoro-4-(2-methylpyridin-4-yl)benzyl)-7-(2-methylpyridin-4-yl)quinazolin-4-amine;
N-(4-(2-methylpyridin-4-yl)benzyl)-7-(pyrazin-2-yl)quinazolin-4-amine;
N-(4-(2-methylpyridin-4-yl)benzyl)-7-(2-fluoropyridin-4-yl)quinazolin-4-amine;
N-(4-(2-methylpyridin-4-yl)benzyl)-7-morpholinoquinazolin-4-amine;
2-(3-fluorophenyl)-N-(4-(2-methylpyridin-4-yl)benzyl)pyrido[3,4-b]pyrazin-5-amine;
2-(3-fluorophenyl)-N-((2'-methyl-[2,4'-bipyridin]-5-yl)methyl)pyrido[3,4-b]pyrazin-5-amine;
2-(3-fluorophenyl)-N-(3-methyl-4-(2-methylpyridin-4-yl)benzyl)pyrido[3,4-b]pyrazin-5-amine;
N-(3-fluoro-4-(2-methylpyridin-4-yl)benzyl)-2-(3-fluorophenyl)pyrido[3,4-b]pyrazin-5-amine;
2-(2-methylpyridin-4-yl)-N-(4-(2-methylpyridin-4-yl)benzyl)pyrido[3,4-b]pyrazin-5-amine;
N-((2'-methyl-[2,4'-bipyridin]-5-yl)methyl)-2-(2-methylpyridin-4-yl)pyrido[3,4-b]pyrazin-5-amine;
N-(3-methyl-4-(2-methylpyridin-4-yl)benzyl)-2-(2-methylpyridin-4-yl)pyrido[3,4-b]pyrazin-5-amine;
N-(3-fluoro-4-(2-methylpyridin-4-yl)benzyl)-2-(2-methylpyridin-4-yl)pyrido[3,4-b]pyrazin-5-amine;
N-((2',3-dimethyl-[2,4'-bipyridin]-5-yl)methyl)-6-(pyrazin-2-yl)-2,7-naphthyridin-1-amine;
6-(2-methylmorpholino)-N-(4-(2-methylpyridin-4-yl)benzyl)-2,7-naphthyridin-1-amine;
(S)-6-(2-methylmorpholino)-N-(4-(2-methylpyridin-4-yl)benzyl)-2,7-naphthyridin-1-amine;

(R)-6-(2-methylmorpholino)-N-(4-(2-methylpyridin-4-yl)
benzyl)-2,7-naphthyridin-1-amine;
1-(4-(8-((4-(2-methylpyridin-4-yl)benzyl)amino)-2,7-naph-
thyridin-3-yl)piperazin-1-yl)ethanone;
6-(1H-imidazol-1-yl)-N-(4-(2-methylpyridin-4-yl)benzyl)-
2,7-naphthyridin-1-amine;
6-(4-methyl-1H-imidazol-1-yl)-N-(4-(2-methylpyridin-4-
yl)benzyl)-2,7-naphthyridin-1-amine;
N-(4-(2-methylpyridin-4-yl)benzyl)-6-(1H-tetrazol-5-yl)-2,
7-naphthyridin-1-amine;
6-(5-methyl-1,3,4-oxadiazol-2-yl)-N-(4-(2-methyl pyridin-
4-yl)benzyl)-2,7-naphthyridin-1-amine;
6-(1-methyl-1H-pyrazol-3-yl)-N-(4-(2-methylpyridin-4-yl)
benzyl)-2,7-naphthyridin-1-amine;
N-(4-(2-methylpyridin-4-yl)benzyl)-6-(thiazol-5-yl)-2,7-
naphthyridin-1-amine;
N-(4-(2-methylpyridin-4-yl)benzyl)-6-(oxazol-5-yl)-2,7-
naphthyridin-1-amine;
N-((2',3-dimethyl-[2,4'-bipyridin]-5-yl)methyl)-6-(5-meth-
ylpyridin-3-yl)-2,7-naphthyridin-1-amine;
N-((2',3-dimethyl-[2,4'-bipyridin]-5-yl)methyl)-6-(2-meth-
ylpyridin-4-yl)-2,7-naphthyridin-1-amine;
N-((3-fluoro-2'-methyl-[2,4'-bipyridin]-5-yl)methyl)-6-(2-
methylpyridin-4-yl)-2,7-naphthyridin-1-amine;
N-((2',3-dimethyl-[2,4'-bipyridin]-5-yl)methyl)-6-(5-fluoro-
pyridin-3-yl)-2,7-naphthyridin-1-amine;
N-(3-methyl-4-(2-methylpyridin-4-yl)benzyl)-6-(pyrazin-2-
yl)-2,7-naphthyridin-1-amine;
N-(3-fluoro-4-(2-methylpyridin-4-yl)benzyl)-6-(pyrazin-2-
yl)-2,7-naphthyridin-1-amine;
methyl 4-(8-((4-(2-methylpyridin-4-yl)benzyl)amino)-2,7-
naphthyridin-3-yl)piperazine-1-carboxylate;
4-(8-((4-(2-methylpyridin-4-yl)benzyl)amino)-2,7-naphthy-
ridin-3-yl)piperazin-2-one;
2-(4-(8-((4-(2-methylpyridin-4-yl)benzyl)amino)-2,7-naph-
thyridin-3-yl)piperazin-1-yl)acetonitrile;
2-methyl-4-(4-(((6-(2-methylpyridin-4-yl)-2,7-naphthyri-
din-1-yl)amino)methyl)phenyl)pyridine 1-oxide;
6-(2-chloropyridin-4-yl)-N-((2',3-dimethyl-[2,4'-bipyridin]-
5-yl)methyl)-2,7-naphthyridin-1-amine;
6-(2-chloropyridin-4-yl)-N-(4-(2-methylpyridin-4-yl)ben-
zyl)-2,7-naphthyridin-1-amine;
2'-methyl-4-(((6-(2-methylpyridin-4-yl)-2,7-naphthyridin-
1-yl)amino)methyl)-2H-[1,4'-bipyridin]-2-one;
2-(2-methylpyridin-4-yl)-5-(((6-(2-methylpyridin-4-yl)-2,7-
naphthyridin-1-yl)amino)methyl)benzonitrile;
N-(3-methoxy-4-(2-methyl pyridin-4-yl)benzyl)-6-(2-meth-
ylpyridin-4-yl)-2,7-naphthyridin-1-amine;
N-((3-chloro-2'-methyl-[2,4'-bipyridin]-5-yl)methyl)-6-(2-
methylpyridin-4-yl)-2,7-naphthyridin-1-amine;
2'-methyl-5-(((6-(2-methylpyridin-4-yl)-2,7-naphthyridin-
1-yl)amino)methyl)-[2,4'-bipyridine]-3-carbonitrile;
N-(4-(2-(difluoromethyl)pyridin-4-yl)benzyl)-6-(2-methyl-
pyridin-4-yl)-2,7-naphthyridin-1-amine;

In some embodiments, the pharmaceutical composition comprising at least one pharmaceutically acceptable carrier or diluent. In some embodiments, the pharmaceutical composition is oral composition, injectable composition or suppository. In some embodiments, the pharmaceutical composition is oral composition and is tablet or gelatin capsule. In some embodiments, the pharmaceutical composition comprises diluents, lubricants, binders, disintegrants, or additives, or combination thereof. In some embodiments, the diluent is lactose, dextrose, sucrose, mannitol, sorbitol, cellulose and/or glycine. In some embodiments, the lubricant is silica, talcum, stearic acid, its magnesium or calcium salt and/or polyethyleneglycol. In some embodiments, the binder is magnesium aluminum silicate, starch paste, gelatin, tragamayth, methylcellulose, sodium carboxymethylcellulose and/or polyvinylpyrrolidone. In some embodiments, the disintegrant is starches, agar, alginic acid or its sodium salt, or effervescent mixtures. In some embodiments, the additive is absorbent, colorant, flavor and/or sweetener.

In some embodiments, the pharmaceutical composition is injectable composition and is aqueous isotonic solution or suspension.

In some embodiments, the pharmaceutical composition is suppository and is prepared from fatty emulsions or suspensions. In some embodiments, the pharmaceutical composition further comprises adjuvants, wherein the adjuvants are preserving, stabilizing, wetting or emulsifying agents, solution promoters, salts for regulating the osmotic pressure and/or buffers.

In some embodiments, the pharmaceutical composition further contains solubilizers, stabilizers, tonicity enhancing agents, buffers and/or preservatives. In some embodiments, the pharmaceutical composition is for topical application and is aqueous solution, ointment, cream or gel.

In some embodiments, the therapeutically effective amount of the compound is about 0.03 to 2.5 mg/kg per body weight at daily dosages. In some embodiments, the therapeutically effective amount of the compound from about 0.5 mg to about 100 mg for humans.

In some embodiments, the pharmaceutical composition is administrated enterally, orally, parenterally, topically or in a nasal or suppository form.

In some embodiments, the R-spondin fusion comprises a gene fusion between PTPRK and Rspo3 genes. In some embodiments, the R-spondin fusion results in expression of R-spondin gene driven by promoter of the PTPRK gene. In some embodiments, the R-spondin fusion comprises a gene fusion between PTPRK exon 1 and Rspo3 exon 2, or between PTPRK exon7 and Rspo3 exon 2. In some embodiments, the R-spondin fusion comprises a gene fusion between EIF3E and Rspo2 genes. In some embodiments, the R-spondin fusion resulted in expression of R-spondin gene driven by promoter of the EIF3E gene. In some embodiments, the R-spondin fusion comprises a gene fusion between EIF3E exon 1 and Rspo2 exon 2 or between EIF3E exon 1 and Rspo2 exon 3.

In some embodiments, the cancer is colorectal cancer, gastric cancer, liver cancer, or esophageal cancer.

In another aspect, the present invention provides a method for determining whether a subject with cancer should be treated with a composition that inhibits Wnt activity, the method comprising: (a) isolating a biological sample from the subject; (b) performing an assay on the biological sample to identify the presence or absence of an R-spondin fusion; and (c) determining that the subject should be treated with a composition that inhibits Wnt activity if the biological sample contains an R-spondin fusion, wherein the composition comprises a compound of the following formula:

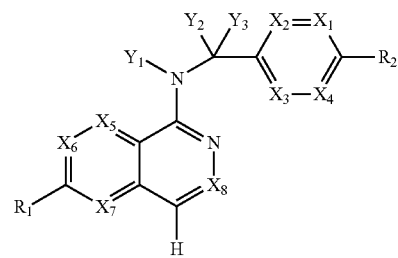

or a physiologically acceptable salt thereof, wherein
$X_1, X_2, X_3, X_4, X_5, X_6, X_7, X_8$ are independently $CR_4$ or N;
$Y_1$ is hydrogen or $CR_4$; $Y_2, Y_3$ are independently hydrogen, halo or $CR_3$;
$R_1$ is morpholinyl, piperazinyl, quinolinyl,

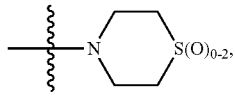

aryl, $C_{1-6}$ heterocycle, 5 or 6 membered heteroaryl containing 1-2 heteroatoms selected from N, O and S;
$R_2$ is hydrogen, halo, morpholinyl, piperazinyl, quinolinyl,

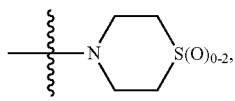

aryl, $C_{1-6}$ heterocycle, 5 or 6 membered heteroaryl containing 1-2 heteroatoms selected from N, O and S; $R_3$ is hydrogen, halo, cyano, $C_{1-6}$ alkyl, $C_{1-6}$ alkoxy optionally substituted with halo, amino, hydroxyl, alkoxy or cyano;
$R_4$ is hydrogen, halo, $C_{1-6}$alkoxy, —$S(O)_2R_5$, —$C(O)OR_5$, —$C(O)R_5$, —$C(O)NR_6R_7$, $C_{1-6}$ alkyl, $C_{2-6}$ alkenyl or $C_{2-6}$ alkynyl, each of which can be optionally substituted with halo, amino, hydroxyl, alkoxy or cyano;
$R_5$, $R_6$ and $R_7$ are independently hydrogen, $C_{1-6}$ alkyl, $C_{2-6}$ alkenyl or $C_{2-6}$ alkynyl, each of which may be optionally substituted with halo, amino, hydroxyl, alkoxy or cyano.

In yet another aspect, the present invention provides use of a compound for the manufacture of a medicament for treating cancer characterized by expression of an R-spondin fusion, wherein the compound is of the following formula:

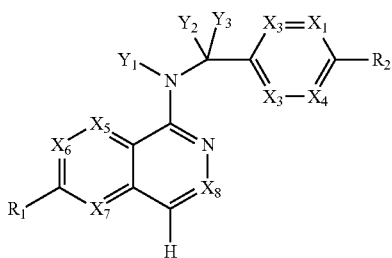

or a physiologically acceptable salt thereof, wherein
$X_1, X_2, X_3, X_4, X_5, X_6, X_7, X_8$ are independently $CR_4$ or N;
$Y_1$ is hydrogen or $CR_4$; $Y_2, Y_3$ are independently hydrogen, halo or $CR_3$;
$R_1$ is morpholinyl, piperazinyl, quinolinyl,

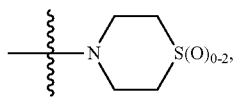

aryl, $C_{1-6}$ heterocycle, 5 or 6 membered heteroaryl containing 1-2 heteroatoms selected from N, O and S;

$R_2$ is hydrogen, halo, morpholinyl, piperazinyl, quinolinyl,

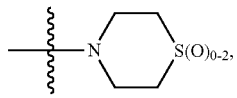

aryl, $C_6$ heterocycle, 5 or 6 membered heteroaryl containing 1-2 heteroatoms selected from N, O and S;
$R_3$ is hydrogen, halo, cyano, $C_{1-6}$ alkyl, $C_{1-6}$ alkoxy optionally substituted with halo, amino, hydroxyl, alkoxy or cyano;
$R_4$ is hydrogen, halo, $C_{1-6}$alkoxy, —$S(O)_2R_5$, —$C(O)OR_5$, —$C(O)R_5$, —$C(O)NR_6R_7$, $C_{1-6}$ alkyl, $C_{2-6}$ alkenyl or $C_{2-6}$ alkynyl, each of which can be optionally substituted with halo, amino, hydroxyl, alkoxy or cyano;
$R_5$, $R_6$ and $R_7$ are independently hydrogen, $C_{1-6}$ alkyl, $C_{2-6}$ alkenyl or $C_{2-6}$ alkynyl, each of which may be optionally substituted with halo, amino, hydroxyl, alkoxy or cyano.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 depicts sequences of PCR primers used in detecting Rspos and PTPRK fusion gene in one of the xenograft model (Model #1) and sequence of the resulted PCR product.

FIG. 4 depicts sequences of PCR primers used in detecting Rspos and PTPRK fusion gene in one of the xenograft model (Model #5) and sequence of the resulted PCR product.

FIG. 6 depicts gene fusions between PTPRK and Rspo3 in gastric and liver tumor models detected by RT-PCR. Data show that gastric tumor model # G10 and liver tumor model # L2 and # L8 have products of gene fusion between PTPRK and Rspo3. Sequencing data show that these tumors have fusion between exon 1 of PTPRK to exon 2 of Rspo3.

FIG. 7 depicts gene fusions between PTPRK and Rspo3 in an esophageal tumor model detected by RT-PCR. Data show that esophageal tumor model # E7 has product of gene fusion between PTPRK and Rspo3. Sequencing data show that this tumor has fusion between exon 7 of PTPRK and exon 2 of Rspo3.

FIG. 8 depicts gene fusions between EIF3E and Rspo2 in liver tumor model detected by RT-PCR. Data show that liver tumor model # L7 has a product of gene fusion between exon 1 of EIF3E and exon 2 of Rspo2.

FIG. 9 depicts gene fusions between EIF3E and Rspo2 in gastric and liver tumor models detected by RT-PCR. Data show that gastric tumor models # G6 and # G13 and liver tumor model # L6 have products of gene fusion between exon 1 of EIF3E and exon 3 of Rspo2.

DETAILED DESCRIPTION OF THE INVENTION

Figure 1:
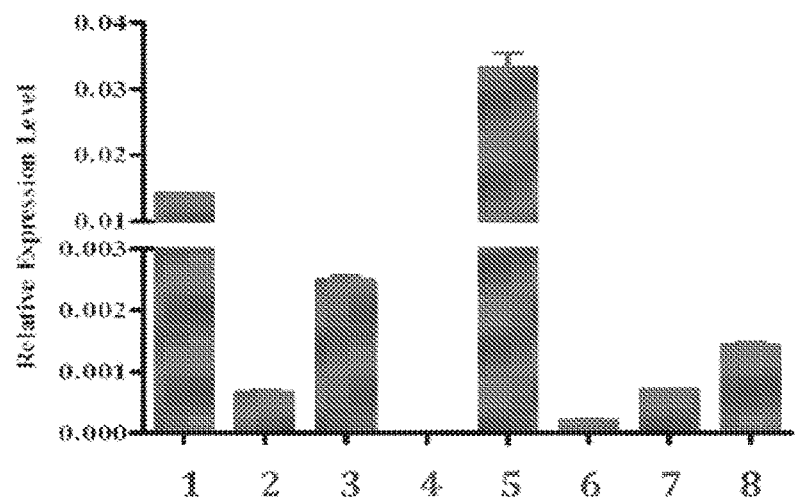
FIG. 1 depicts expression of Rspo3 in colorectal tumor models detected by quantitative RT-PCR. Data show that Model #1 and #5 have higher expression of Rspo3.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events.

Furthermore, not all illustrated acts or events are required to implement a methodology in accordance with the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

I. Definitions and Abbreviations

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references, which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

As used herein, "WNT signaling pathway" or "WNT pathway" refers to the pathway by which binding of the WNT protein to cellular receptors results in changes of cell behavior. The WNT pathway involves a variety of proteins including Frizzled, Disheveled, Axin, APC, GSK33, β-catenin, LEF/TCF transcription factors, and molecules involved in the synthesis and secretion of WNT proteins. Examples of proteins implicated in the secretion of functional WNTs include, but are not limited to wntless/evenness interrupted (Wls/Evi), porcupine (Porcn), and Vps35p. Wls/Evi is a 7 pass transmembrane protein which resides in the Golgi apparatus and is required for secretion of Wg (*drosophila*) MOM-2 (*C. elegans*) and Wnt3A. It contains a conserved structural motif whose structure and function are both unknown. Porcupine (Porcn) is a member of the membrane-bound O-acyltransferase (MBOAT) family of palmitoyl transferases. Fatty acid modification of Wnts is critical for their function. Wnts are palmitoylated on one or two highly conserved sites. Inhibitors of Porcn may therefore block all functional Wnt signaling. Vps35p is a subunit of a multiprotein complex called the retromer complex which is involved in intracellular protein trafficking. Vps35p functions in binding target proteins like WNTs for recruitment into vesicles.

"WNT pathway inhibitor" or "WNT signaling inhibitor" is a small organic molecule that inhibits WNT signaling activity and typically has a molecular weight of about 800 g/mol or less.

The term "a method of inhibiting WNT pathway" refers to methods of inhibiting known biochemical events associated with production of functional WNT proteins or with cellular responses to WNT proteins. As discussed herein, small organic molecules may inhibit WNT response in accordance with this definition.

"WNT protein" is a protein binds to Frizzled and LRP5/6 co-receptors so as to activate canonical or non-canonical WNT signaling. Specific examples of WNT proteins include: WNT-1 (NM005430), WNT-2 (NM003391), WNT-2B/WNT-13 (NM004185), WNT-3 (NM030753), WNT3a (NM033131), WNT-4 (NM030761), WNT-5A (NM003392), WNT-5B (NM032642), WNT-6 (NM006522), WNT-7A (NM004625), WNT-7B (NM058238), WNT-8A (NM058244), WNT-8B (NM003393), WNT-9A/WNT-14) (NM003395), WNT-9B/

WNT-15 (NM003396), WNT-10A (NM025216), WNT-10B (NM003394), WNT-11 (NM004626), WNT-16 (NM016087).

"WNT pathway disorder" is a condition or disease state with aberrant WNT signaling. In one aspect, the aberrant WNT signaling is a level of WNT signaling in a cell or tissue suspected of being diseased that exceeds the level of WNT signaling in a normal cell or tissue. In one specific aspect, a WNT-mediated disorder includes cancer or fibrosis.

The term "cancer" refers to the pathological condition in humans that is characterized by unregulated cell proliferation. Examples include but are not limited to: carcinoma, lymphoma, blastoma, and leukemia. More particular examples of cancers include but are not limited to: lung (small cell and non-small cell), breast, prostate, carcinoid, bladder, gastric, pancreatic, liver (hepatocellular), hepatoblastoma, colorectal, head and neck squamous cell carcinoma, esophageal, ovarian, cervical, endometrial, mesothelioma, melanoma, sarcoma, osteosarcoma, liposarcoma, thyroid, desmoids, chronic myelocytic leukemia (AML), and chronic myelocytic leukemia (CML).

The term "fibrosis" refers to the pathological condition in humans that is typically characterized by uncontrolled proliferation of fibroblast cells and tissue hardening. Specific examples include but not limited to: lung fibrosis (idiopathic pulmonary fibrosis and radiation-induced fibrosis), renal fibrosis and liver fibrosis including liver cirrhosis.

"Inhibiting" or "treating" or "treatment" refers to reduction and therapeutic treatment wherein the objective is to reduce the aimed pathologic disorder or condition. In one example, following administering of a WNT signaling inhibitor, a cancer patient may experience a reduction in tumor size. "Treatment" or "treating" includes (1) alleviating a disease in a subject experiencing or displaying the pathology or symptoms of the disease, (2) ameliorating a disease in a subject that is experiencing or displaying the pathology or symptoms of the disease, and/or (3) affecting any measurable decrease in a disease in a subject or patient that is experiencing or displaying the pathology or symptoms of the disease. To the extent the WNT pathway inhibitor may prevent growth and/or kill cancer cells, it may be cytostatic and/or cytotoxic.

The term "therapeutically effective amount" refers to an amount of a WNT pathway inhibitor effective to "treat" a WNT pathway disorder in a subject or mammal. In the case of cancer, the therapeutically effective amount of the drug may either reduce the number of cancer cells, reduce the tumor size, inhibit cancer cell infiltration into peripheral organs, inhibit tumor metastasis, inhibit tumor growth to certain extent, and/or relieve one or more of the symptoms associated with the cancer to some extent.

Administration "in combination with" one or more further therapeutic agents includes simultaneous (concurrent) and consecutive administration in any order. As used herein, the term "pharmaceutical combination" refers to a product obtained from mixing or combining active ingredients, and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

A "chemotherapeutic agent" is a chemical compound useful in the treatment of cancer. Examples are but not limited to: Gemcitabine, Irinotecan, Doxorubicin, 5-Fluorouracil, Cytosine arabinoside ("Ara-C"), Cyclophosphamide, Thiotepa, Busulfan, Cytoxin, TAXOL, Methotrexate, Cisplatin, Melphalan, Vinblastine and Carboplatin.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups, are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—

CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

In general, an "acyl substituent" is also selected from the group set forth above. As used herein, the term "acyl substituent" refers to groups attached to, and fulfilling the valence of a carbonyl carbon that is either directly or indirectly attached to the polycyclic nucleus of the compounds of the present invention.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroakyl substituents," respectively, and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively, and are varied and selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound of the invention includes more than one R group, for example, each of the R groups is independently selected as are each R', R", R'" and R"" groups when more than one of these groups is present.

Two of the aryl substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$) alkyl.

As used herein, the term "heteroatom" includes oxygen (O), nitrogen (N), sulfur (S), phosphorus (P) and silicon (Si).

II. The Compositions

In one aspect, the present invention provides a compound as WNT signaling inhibitor, which has the structure of Formula I:

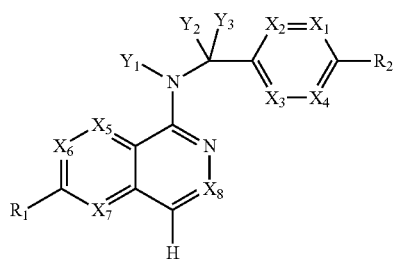

(I)

or a physiologically acceptable salt thereof, wherein,
X1, X2, X3, X4, X5, X6, X7, X8 are independently CR4 or N
Y$_1$ is hydrogen or CR$_4$;
Y$_2$, Y$_3$ are independently hydrogen, halo or CR$_3$;
R$_1$ is morpholinyl, piperazinyl, quinolinyl,

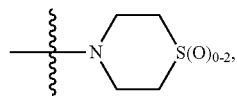

aryl, C$_{1-6}$ heterocycle, 5 or 6 membered heteroaryl containing 1-2 heteroatoms selected from N, O and S;
R$_2$ is hydrogen, halo, morpholinyl, piperazinyl, quinolinyl,

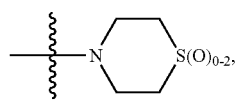

aryl, C$_{1-6}$ heterocycle, 5 or 6 membered heteroaryl containing 1-2 heteroatoms selected from N, O and S; wherein 5 or 6 membered heteroaryl includes the following selected groups but is not limited to:

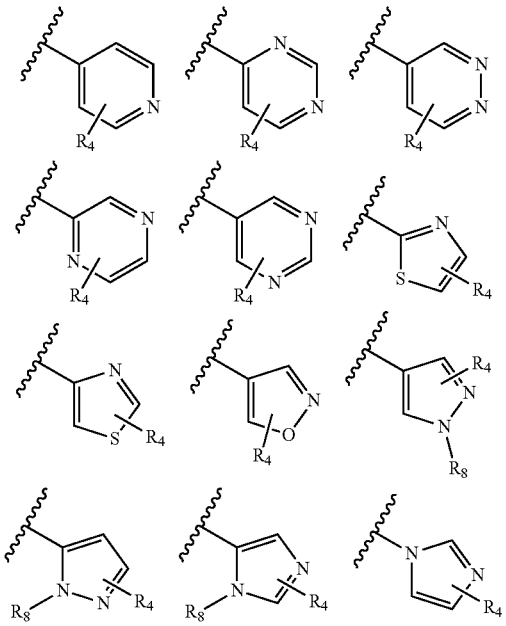

R$_1$ and R$_2$ could be independently and optionally substituted with 1-2 R$_4$ groups;
R$_a$ is hydrogen, halo, cyano, C$_{1-6}$ alkyl, C$_{1-6}$ alkoxy optionally substituted with halo, amino, hydroxyl, alkoxy or cyano;
R$_4$ is hydrogen, halo, C$_{1-6}$alkoxy, —S(O)$_2$R$_5$, —C(O)OR$_5$, —C(O)R$_5$, —C(O)NR$_6$R$_7$, C$_{1-6}$ alkyl, C$_{2-6}$ alkenyl or C$_{2-6}$ alkynyl, each of which can be optionally substituted with halo, amino, hydroxyl, alkoxy or cyano;
R$_5$, R$_6$ and R$_7$ are independently hydrogen, C$_{1-6}$ alkyl, C$_{2-6}$ alkenyl or C$_{2-6}$ alkynyl, each of which may be optionally substituted with halo, amino, hydroxyl, alkoxy or cyano;
R$_8$ is hydrogen or C$_{1-6}$ alkyl.

As used herein, an H atom in any substituent groups (e.g., CH$_2$) encompasses all suitable isotopic variations, e.g., H, $^2$H and $^3$H.

As used herein, other atoms in any substituent groups encompasses all suitable isotopic variations, including but not limited to $^{11}$C, $^{13}$C, $^{14}$C, $^{15}$N, $^{17}$O, $^{18}$O, $^{35}$S, $^{18}$F, $^{36}$I and/or $^{123}$I.

In some embodiments, example of the compound of the invention includes but is not limited to:
N-((6-(2-methylpyridin-4-yl)pyridin-3-yl)methyl)-7-phenylquinazolin-4-amine;
N-((5-(2-methylpyridin-4-yl)pyridin-2-yl)methyl)-7-phenylquinazolin-4-amine;
N-(4-morpholinobenzyl)-7-phenylquinazolin-4-amine;
N-((6-morpholinopyridin-3-yl)methyl)-7-phenylquinazolin-4-amine;
N-((6-(2-methylmorpholino)pyridin-3-yl)methyl)-7-phenylquinazolin-4-amine;
N-((6-(4-methyl piperazin-1-yl)pyridin-3-yl)methyl)-7-phenylquinazolin-4-amine;
4-(5-(((7-phenylquinazolin-4-yl)amino)methyl)pyridin-2-yl)thiomorpholine 1,1-dioxide;
N-((6-(6-methylpyridin-3-yl)pyridin-3-yl)methyl)-7-phenylquinazolin-4-amine;
N-((6-(5-methylpyridin-3-yl)pyridin-3-yl)methyl)-7-phenylquinazolin-4-amine;

7-phenyl-N-((6-(pyridin-4-yl)pyridin-3-yl)methyl)quinazolin-4-amine;
7-phenyl-N-((6-(pyridin-3-yl)pyridin-3-yl)methyl)quinazolin-4-amine;
7-phenyl-N-((6-(pyridin-2-yl)pyridin-3-yl)methyl)quinazolin-4-amine;
7-phenyl-N-((6-(pyridazin-4-yl)pyridin-3-yl)methyl)quinazolin-4-amine;
7-phenyl-N-((6-(pyrazin-2-yl)pyridin-3-yl)methyl)quinazolin-4-amine;
7-phenyl-N-((6-(pyrimidin-5-yl)pyridin-3-yl)methyl)quinazolin-4-amine;
N-((6-(2-fluoropyridin-4-yl)pyridin-3-yl)methyl)-7-phenylquinazolin-4-amine;
N-((6-(4-methyl-1H-imidazol-1-yl)pyridin-3-yl)methyl)-7-phenylquinazolin-4-amine;
N-((6-(1-methyl-1H-pyrazol-4-yl)pyridin-3-yl)methyl)-7-phenylquinazolin-4-amine;
N-((5-(6-methylpyridin-3-yl)pyridin-2-yl)methyl)-7-phenylquinazolin-4-amine;
N-(4-(2-methylpyridin-4-yl)benzyl)-7-phenylquinazolin-4-amine;
N-(4-(2-fluoropyridin-4-yl)benzyl)-7-phenylquinazolin-4-amine;
N-benzyl-7-(2-methylpyridin-4-yl)quinazolin-4-amine;
N-(4-methylbenzyl)-7-(2-methylpyridin-4-yl)quinazolin-4-amine;
N-(4-methoxybenzyl)-7-(2-methylpyridin-4-yl)quinazolin-4-amine;
N-(4-fluorobenzyl)-7-(2-methylpyridin-4-yl)quinazolin-4-amine;
N-(4-chlorobenzyl)-7-(2-methylpyridin-4-yl)quinazolin-4-amine;
N-(4-bromobenzyl)-7-(2-methylpyridin-4-yl)quinazolin-4-amine;
N-(4-(trifluoromethyl)benzyl)-7-(2-methylpyridin-4-yl)quinazolin-4-amine;
4-((7-(2-methylpyridin-4-yl)quinazolin-4-ylamino)methyl)benzonitrile; N-(4-morpholinobenzyl)-7-(2-methylpyridin-4-yl)quinazolin-4-amine;
N-(4-phenylbenzyl)-7-(2-methylpyridin-4-yl)quinazolin-4-amine;
N-(3-fluoro-4-phenylbenzyl)-7-(2-methylpyridin-4-yl)quinazolin-4-amine;
N-(4-(3-fluorophenyl)benzyl)-7-(2-methylpyridin-4-yl)quinazolin-4-amine;
7-(3-fluorophenyl)-N-((6-(2-methylpyridin-4-yl)pyridin-3-yl)methyl)quinazolin-4-amine;
7-(3-chlorophenyl)-N-((6-(2-methylpyridin-4-yl)pyridin-3-yl)methyl)quinazolin-4-amine;
N-((6-(2-methylpyridin-4-yl)pyridin-3-yl)methyl)-7-m-tolylquinazolin-4-amine;
3-(4-((6-(2-methylpyridin-4-yl)pyridin-3-yl)methylamino)quinazolin-7-yl)benzonitrile;
4-(4-((6-(2-methylpyridin-4-yl)pyridin-3-yl)methylamino)quinazolin-7-yl)benzonitrile;
7-(2-methylpyridin-4-yl)-N-((6-(2-methylpyridin-4-yl)pyridin-3-yl)methyl)quinazolin-4-amine;
7-(6-methylpyridin-3-yl)-N-((6-(2-methylpyridin-4-yl)pyridin-3-yl)methyl)quinazolin-4-amine;
7-(5-methylpyridin-3-yl)-N-((6-(2-methylpyridin-4-yl)pyridin-3-yl)methyl)quinazolin-4-amine;
N-((6-(2-methylpyridin-4-yl)pyridin-3-yl)methyl)-7-(pyridin-2-yl)quinazolin-4-amine;
N-((6-(2-methylpyridin-4-yl)pyridin-3-yl)methyl)-7-(pyridin-3-yl)quinazolin-4-amine;
N-((6-(2-methylpyridin-4-yl)pyridin-3-yl)methyl)-7-(pyridin-4-yl)quinazolin-4-amine;
N-((6-(2-methyl pyridin-4-yl)pyridin-3-yl)methyl)-7-(pyridazin-4-yl)quinazolin-4-amine;
N-((6-(2-methyl pyridin-4-yl)pyridin-3-yl)methyl)-7-(pyrazin-2-yl)quinazolin-4-amine;
N-((6-(2-methylpyridin-4-yl)pyridin-3-yl)methyl)-7-(pyrimidin-5-yl)quinazolin-4-amine;
7-(2-fluoropyridin-4-yl)-N-((6-(2-methylpyridin-4-yl)pyridin-3-yl)methyl)quinazolin-4-amine;
7-(2-(trifluoromethyl)pyridin-4-yl)-N-((6-(2-methylpyridin-4-yl)pyridin-3-yl)methyl)quinazolin-4-amine;
7-(2-methoxypyridin-4-yl)-N-((6-(2-methylpyridin-4-yl)pyridin-3-yl)methyl)quinazolin-4-amine;
7-(3-methyl pyridin-4-yl)-N-((6-(2-methylpyridin-4-yl)pyridin-3-yl)methyl)quinazolin-4-amine;
N-((6-(2-methylpyridin-4-yl)pyridin-3-yl)methyl)-7-morpholinoquinazolin-4-amine;
N-((6-(2-methylpyridin-4-yl)pyridin-3-yl)methyl)-7-(piperidin-1-yl)quinazolin-4-amine;
7-(4-methylpiperazin-1-yl)-N-((6-(2-methylpyridin-4-yl)pyridin-3-yl)methyl)quinazolin-4-amine;
1-(4-(4-((6-(2-methylpyridin-4-yl)pyridin-3-yl)methylamino)quinazolin-7-yl) piperazin-1-yl)ethanone;
4-(4-(((2'-methyl-[2,4'-bipyridin]-5-yl)methyl)amino)quinazolin-7-yl)thiomorpholine 1,1-dioxide;
7-(1,2,3,6-tetrahydropyridin-4-yl)-N-((6-(2-methylpyridin-4-yl)pyridin-3-yl)methyl)quinazolin-4-amine;
7-(1,2,3,6-tetrahydropyridin-4-yl)-N-((6-(2-methylpyridin-4-yl)pyridin-3-yl)methyl)quinazolin-4-amine;
1-(4-(4-((6-(2-methylpyridin-4-yl)pyridin-3-yl)methylamino)quinazolin-7-yl)piperidin-1-yl)ethanone;
N-((2'-methyl-[2,4'-bipyridin]-5-yl)methyl)-7-(4-(methylsulfonyl)piperazin-1-yl)quinazolin-4-amine;
7-(1-methyl-1H-pyrazol-4-yl)-N-((6-(2-methylpyridin-4-yl)pyridin-3-yl)methyl)quinazolin-4-amine;
7-(isoxazol-4-yl)-N-((6-(2-methylpyridin-4-yl)pyridin-3-yl)methyl)quinazolin-4-amine;
N-((6-(2-methylpyridin-4-yl)pyridin-3-yl)methyl)-7-(thiazol-2-yl)quinazolin-4-amine;
N-(3-methyl-4-(2-methylpyridin-4-yl)benzyl)-7-(2-methylpyridin-4-yl)quinazolin-4-amine;
N-(3-fluoro-4-(2-methylpyridin-4-yl)benzyl)-7-(2-methylpyridin-4-yl)quinazolin-4-amine;
N-(4-(2-methylpyridin-4-yl)benzyl)-7-(pyrazin-2-yl)quinazolin-4-amine;
N-(4-(2-methylpyridin-4-yl)benzyl)-7-(2-fluoropyridin-4-yl)quinazolin-4-amine;
N-(4-(2-methylpyridin-4-yl)benzyl)-7-morpholinoquinazolin-4-amine;
2-(3-fluorophenyl)-N-(4-(2-methylpyridin-4-yl)benzyl)pyrido[3,4-b]pyrazin-5-amine;
2-(3-fluorophenyl)-N-((2'-methyl-[2,4'-bipyridin]-5-yl)methyl)pyrido[3,4-b]pyrazin-5-amine;
2-(3-fluorophenyl)-N-(3-methyl-4-(2-methylpyridin-4-yl)benzyl)pyrido[3,4-b]pyrazin-5-amine;
N-(3-fluoro-4-(2-methylpyridin-4-yl)benzyl)-2-(3-fluorophenyl)pyrido[3,4-b]pyrazin-5-amine;
2-(2-methyl pyridin-4-yl)-N-(4-(2-methyl pyridin-4-yl)benzyl)pyrido[3,4-b]pyrazin-5-amine;
N-((2'-methyl-[2,4'-bipyridin]-5-yl)methyl)-2-(2-methylpyridin-4-yl)pyrido[3,4-b]pyrazin-5-amine;
N-(3-methyl-4-(2-methylpyridin-4-yl)benzyl)-2-(2-methylpyridin-4-yl)pyrido[3,4-b]pyrazin-5-amine;
N-(3-fluoro-4-(2-methylpyridin-4-yl)benzyl)-2-(2-methylpyridin-4-yl)pyrido[3,4-b]pyrazin-5-amine;

N-((2',3-dimethyl-[2,4'-bipyridin]-5-yl)methyl)-6-(pyrazin-2-yl)-2,7-naphthyridin-1-amine;
6-(2-methylmorpholino)-N-(4-(2-methylpyridin-4-yl)benzyl)-2,7-naphthyridin-1-amine;
(S)-6-(2-methylmorpholino)-N-(4-(2-methylpyridin-4-yl)benzyl)-2,7-naphthyridin-1-amine;
(R)-6-(2-methylmorpholino)-N-(4-(2-methylpyridin-4-yl)benzyl)-2,7-naphthyridin-1-amine;
1-(4-(8-((4-(2-methylpyridin-4-yl)benzyl)amino)-2,7-naphthyridin-3-yl)piperazin-1-yl)ethanone;
6-(1H-imidazol-1-yl)-N-(4-(2-methylpyridin-4-yl)benzyl)-2,7-naphthyridin-1-amine;
6-(4-methyl-1H-imidazol-1-yl)-N-(4-(2-methylpyridin-4-yl)benzyl)-2,7-naphthyridin-1-amine;
N-(4-(2-methylpyridin-4-yl)benzyl)-6-(1H-tetrazol-5-yl)-2,7-naphthyridin-1-amine;
6-(5-methyl-1,3,4-oxadiazol-2-yl)-N-(4-(2-methyl pyridin-4-yl)benzyl)-2,7-naphthyridin-1-amine;
6-(1-methyl-1H-pyrazol-3-yl)-N-(4-(2-methylpyridin-4-yl)benzyl)-2,7-naphthyridin-1-amine;
N-(4-(2-methylpyridin-4-yl)benzyl)-6-(thiazol-5-yl)-2,7-naphthyridin-1-amine;
N-(4-(2-methylpyridin-4-yl)benzyl)-6-(oxazol-5-yl)-2,7-naphthyridin-1-amine;
N-((2',3-dimethyl-[2,4'-bipyridin]-5-yl)methyl)-6-(5-methylpyridin-3-yl)-2,7-naphthyridin-1-amine;
N-((2',3-dimethyl-[2,4'-bipyridin]-5-yl)methyl)-6-(2-methylpyridin-4-yl)-2,7-naphthyridin-1-amine;
N-((3-fluoro-2'-methyl-[2,4'-bipyridin]-5-yl)methyl)-6-(2-methylpyridin-4-yl)-2,7-naphthyridin-1-amine;
N-((2',3-dimethyl-[2,4'-bipyridin]-5-yl)methyl)-6-(5-fluoropyridin-3-yl)-2,7-naphthyridin-1-amine;
N-(3-methyl-4-(2-methylpyridin-4-yl)benzyl)-6-(pyrazin-2-yl)-2,7-naphthyridin-1-amine;
N-(3-fluoro-4-(2-methylpyridin-4-yl)benzyl)-6-(pyrazin-2-yl)-2,7-naphthyridin-1-amine;
methyl 4-(8-((4-(2-methylpyridin-4-yl)benzyl)amino)-2,7-naphthyridin-3-yl)piperazine-1-carboxylate;
4-(8-((4-(2-methylpyridin-4-yl)benzyl)amino)-2,7-naphthyridin-3-yl)piperazin-2-one;
2-(4-(8-((4-(2-methylpyridin-4-yl)benzyl)amino)-2,7-naphthyridin-3-yl)piperazin-1-yl)acetonitrile;
2-methyl-4-(4-(((6-(2-methylpyridin-4-yl)-2,7-naphthyridin-1-yl)amino)methyl)phenyl)pyridine 1-oxide;
6-(2-chloropyridin-4-yl)-N-((2',3-dimethyl-[2,4'-bipyridin]-5-yl)methyl)-2,7-naphthyridin-1-amine;
6-(2-chloropyridin-4-yl)-N-(4-(2-methylpyridin-4-yl)benzyl)-2,7-naphthyridin-1-amine;
2'-methyl-4-(((6-(2-methylpyridin-4-yl)-2,7-naphthyridin-1-yl)amino)methyl)-2H-[1,4'-bipyridin]-2-one;
2-(2-methylpyridin-4-yl)-5-((((6-(2-methylpyridin-4-yl)-2,7-naphthyridin-1-yl)amino)methyl)benzonitrile;
N-(3-methoxy-4-(2-methyl pyridin-4-yl)benzyl)-6-(2-methylpyridin-4-yl)-2,7-naphthyridin-1-amine;
N-((3-chloro-2'-methyl-[2,4'-bipyridin]-5-yl)methyl)-6-(2-methylpyridin-4-yl)-2,7-naphthyridin-1-amine;
2'-methyl-5-(((6-(2-methylpyridin-4-yl)-2,7-naphthyridin-1-yl)amino)methyl)-[2,4'-bipyridine]-3-carbonitrile;
N-(4-(2-(difluoromethyl)pyridin-4-yl)benzyl)-6-(2-methylpyridin-4-yl)-2,7-naphthyridin-1-amine;
or physiologically acceptable salts thereof.

In some embodiments, examples of the compound of the invention include but are not limited to the compounds provided in Examples 1-5 and Table 1. A person skilled in the art can clearly understand and know that the other compounds could be prepared by the same strategy as examples 1-5.

TABLE 1

Compound Table

| No. | Compound Structure | Compound physical characterization |
|---|---|---|
| 6 | 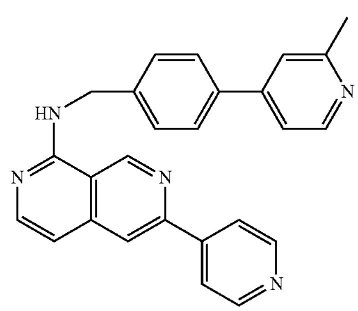 [SMILES: Cc1cc(-c2ccc(CNc3nccc4cc(-c5ccncc5)ncc34)cc2)ccn1] | MS m/z = 404.2 (M + 1); |
| 7 | 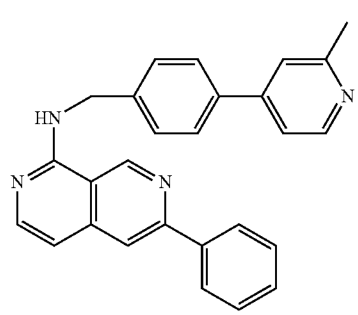 [SMILES: Cc1cc(-c2ccc(CNc3nccc4cc(-c5ccccc5)ncc34)cc2)ccn1] | MS m/z = 403.2 (M + 1); |

TABLE 1-continued

Compound Table

| No. | Compound Structure | Compound physical characterization |
|---|---|---|
| 8 | 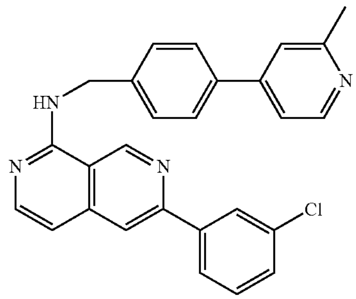 | MS m/z = 437.2 (M + 1); |
| 9 | 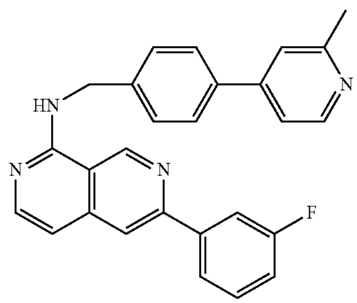 [SMILES: Cc1cc(-c2ccc(CNc3nccc4cc(-c5cccc(F)c5)ncc34)cc2)ccn1] | MS m/z = 421.2 (M + 1); $^1$H NMR (400 MHz, DMSO-d6) δ 9.82 (s, 1H), 8.76 (d, J = 6.0 Hz, 1H), 8.39 (s, 1H), 8.17 (s, 1H), 7.95-8.18 (m, 6H), 7.58-7.66 (m, 3H), 7.35 (t, J = 8.0 Hz, 1H), 7.07 (d, J = 6.0 Hz, 1H), 5.77 (s, 1H), 4.92 (d, J = 6.0 Hz, 1H), 2.70 (s, 3H) |
| 10 | 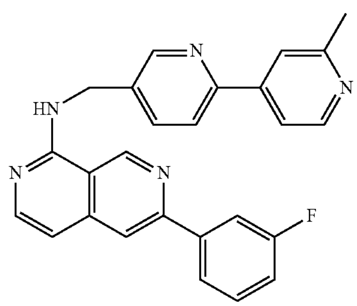 [SMILES: Cc1cc(-c2ccc(CNc3nccc4cc(-c5cccc(F)c5)ncc34)cn2)ccn1] | MS m/z = 422.2 (M + 1); |
| 11 | 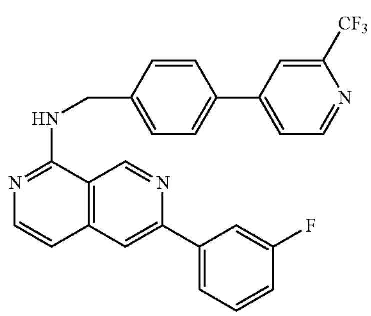 [SMILES: Fc1cccc(-c2cc3ccnc(NCc4ccc(-c5ccnc(C(F)(F)F)c5)cc4)c3cn2)c1] | MS m/z = 475.2 (M + 1); |
| 12 | 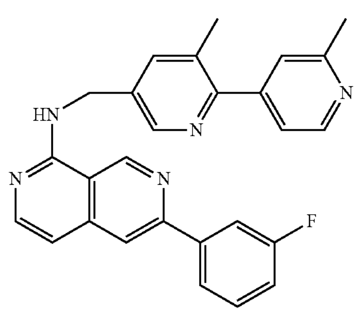 [SMILES: Cc1cc(-c2ncc(CNc3nccc4cc(-c5cccc(F)c5)ncc34)cc2C)ccn1] | MS m/z = 436.2 (M + 1); |

TABLE 1-continued

Compound Table

| No. | Compound Structure | Compound physical characterization |
|---|---|---|
| 13 | 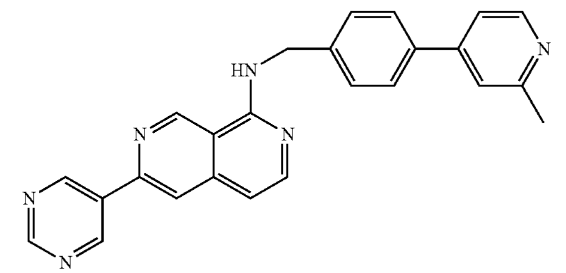 | MS m/z = 405.2 (M + 1); |
| 14 | 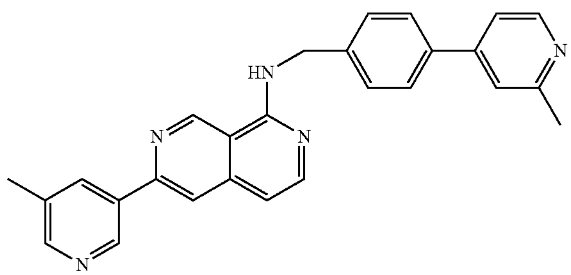 | MS m/z = 418.2 (M + 1); $^1$H NMR (300 MHz, CDCl$_3$): δ2.46 (s, 3H), 2.63 (s, 3H), 4.94 (d, J = 5.10 Hz, 2H), 5.94 (br, 1H), 6.97 (d, J = 5.70 Hz, 1H), 7.31 (d, J = 4.20 Hz, 1H), 7.36 (s, 1H), 7.54 (d, J = 8.10 Hz, 2H), 7.63 (d, J = 8.40 Hz, 2H), 7.90 (s, 1H), 8.19 (d, J = 6.00 Hz, 1H), 8.22 (s, 1H), 8.51 (m, 2H), 9.08 (s, 1H), 9.30 (s, 1H). |
| 15 | 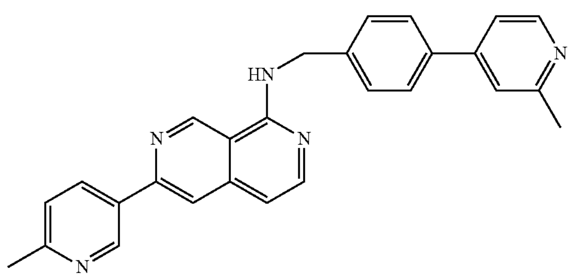 | MS m/z = 418.2 (M + 1); |
| 16 | 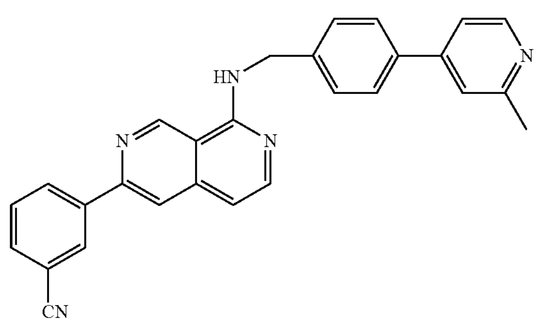 [SMILES: Cc1cc(-c2ccc(CNc3nccc4cc(-c5cccc(C#N)c5)ncc34)cc2)ccn1] | MS m/z = 428.2 (M + 1); $^1$H NMR (300 MHz, CDCl$_3$): δ2.64 (s, 3H), 4.96 (d, J = 5.10 Hz, 2H), 5.99 (br, 1H), 7.31 (d, J = 5.10 Hz, 1H), 7.37 (s, 1H), 7.63 (m, 1H), 7.73 (m, 1H), 7.91 (s, 1H), 8.22 (d, J = 5.70 Hz, 1H), 8.33 (m, 1H), 8.44 (s, 1H), 8.53 (d, J = 5.10 Hz, 1H), 9.33 (s, 1H). |
| 17 | 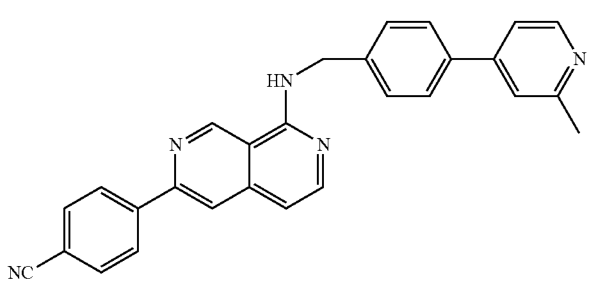 [SMILES: Cc1cc(-c2ccc(CNc3nccc4cc(-c5ccc(C#N)cc5)ncc34)cc2)ccn1] | MS m/z = 428.2 (M + 1); |

TABLE 1-continued

Compound Table

| No. | Compound Structure | Compound physical characterization |
|---|---|---|
| 18 | 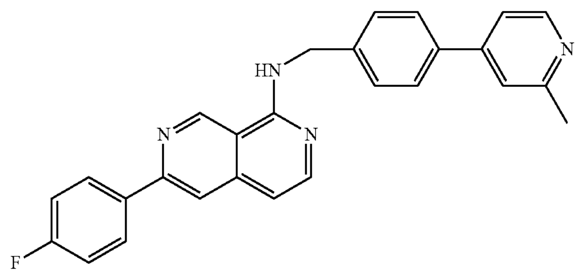 [SMILES: Cc1cc(-c2ccc(CNc3nccc4cc(-c5ccc(F)cc5)ncc34)cc2)ccn1] | MS m/z = 420.2 (M + 1); |
| 19 | 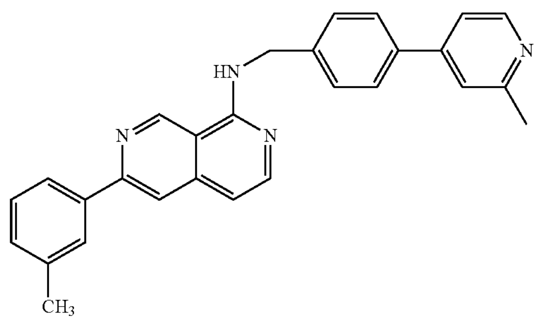 [SMILES: Cc1cccc(-c2cc3ccnc(NCc4ccc(-c5ccnc(C)c5)cc4)c3cn2)c1] | MS m/z = 417.2 (M + 1); |
| 20 | 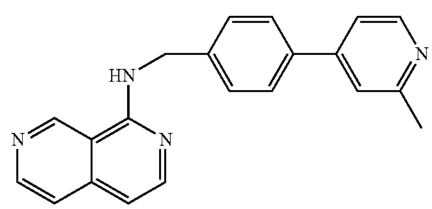 [SMILES: Cc1cc(-c2ccc(CNc3nccc4ccncc34)cc2)ccn1] | MS m/z = 326.1 (M + 1); $^1$H NMR (300 MHz, CDCl$_3$): δ2.58 (s, 3H), 4.90 (d, J = 5.1 Hz, 2H), 5.96 (br, 1H), 6.91 (d, J = 6.0 Hz, 1H), 7.48-7.58 (m, 4H), 7.62 (d, J = 5.7 Hz, 1H), 7.70 (d, J = 8.4 Hz, 2H), 8.02 (d, J = 5.7 Hz, 1H), 8.40 (d, J = 5.1 Hz, 1H), 8.53 (d, J = 5.7 Hz, 1H), 9.50 (s, 1H). |
| 21 | 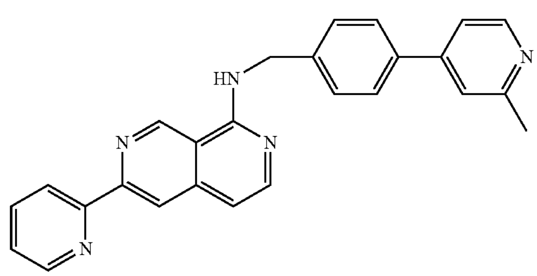 | MS m/z = 404.2 (M + 1); |
| 22 | 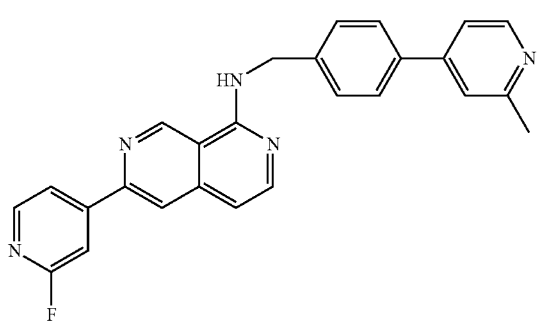 [SMILES: Cc1cc(-c2ccc(CNc3nccc4cc(-c5ccnc(F)c5)ncc34)cc2)ccn1] | MS m/z = 422.2 (M + 1); $^1$H NMR (300 MHz, CDCl$_3$): δ2.64 (s, 3H), 4.96 (d, J = 5.40 Hz, 2H), 5.96 (br, 1H), 7.01 (d, J = 6.00 Hz, 1H), 7.31 (m, 1H), 7.37 (s, 1H), 7.56 (d, J = 8.10 Hz, 2H), 7.64 (d, J = 8.10 Hz, 2H), 7.88 (m, 1H), 7.99 (s, 1H), 8.25 (d, J = 6.00 Hz, 1H), 8.36 (d, J = 8.10 Hz, 1H), 9.32 (s, 1H). |

TABLE 1-continued
Compound Table
| No. | Compound Structure | Compound physical characterization |
|---|---|---|
| 23 | 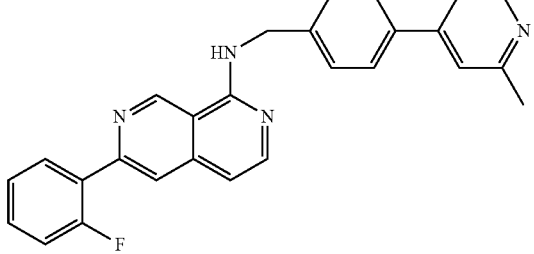 | MS m/z = 421.2 (M + 1); |
| 24 | 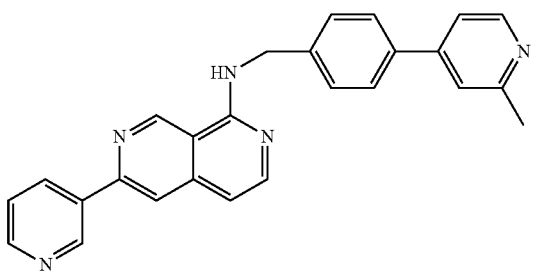 | MS m/z = 404.2 (M + 1); |
| 25 | 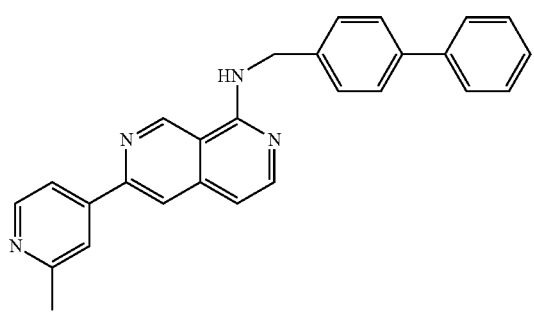 [SMILES: Cc1cc(-c2cc3ccnc(NCc4ccc(-c5ccccc5)cc4)c3cn2)ccn1] | MS M/z = 403.2 (M + 1); |
| 26 | 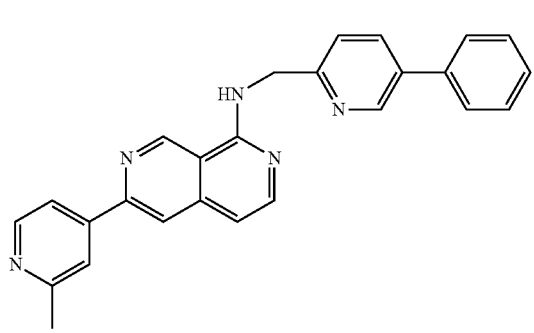 [SMILES: Cc1cc(-c2cc3ccnc(NCc4ccc(-c5ccccc5)cn4)c3cn2)ccn1] | MS m/z = 404.2 (M + 1); |
| 27 | 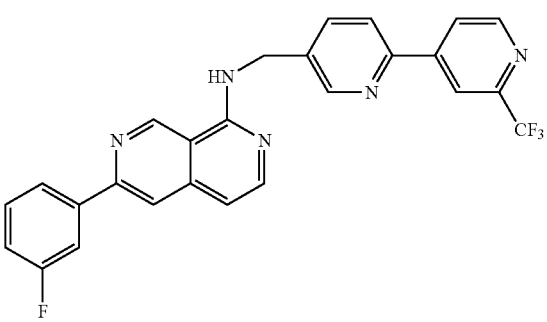 [SMILES: Fc1cccc(-c2cc3ccnc(NCc4ccc(-c5ccnc(C(F)(F)F)c5)nc4)c3cn2)c1] | MS m/z = 476.2 (M + 1); |

TABLE 1-continued

Compound Table

| No. | Compound Structure | Compound physical characterization |
|---|---|---|
| 28 | 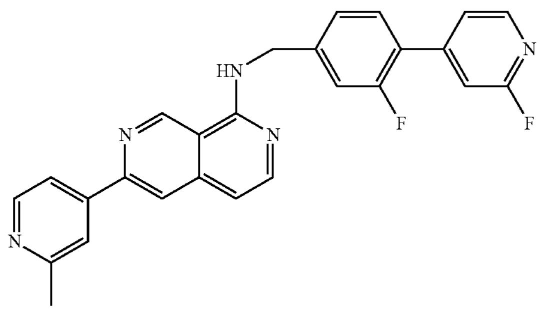 | MS m/z = 440.2 (M + 1); 1H NMR (300 MHz, CDCl3): δ2.61 (s, 3H), 4.88 (d, J = 5.70 Hz, 2H), 5.98 (br, 1H), 6.92 (d, J = 5.7 Hz, 1H), 7.02 (s, 1H), 7.26 (m, 3H), 7.37 (t, J = 7.8 Hz, 1H), 7.68 (d, J = 5.4 Hz, 1H), 7.79 (s, 1H), 7.89 (s, 1H), 8.11 (d, J = 6.0 Hz, 1H), 8.17 (d, J = 5.1 Hz, 1H), 8.55 (d, J = 5.4 Hz, 1H), 9.26 (s, 1H). |
| 29 | 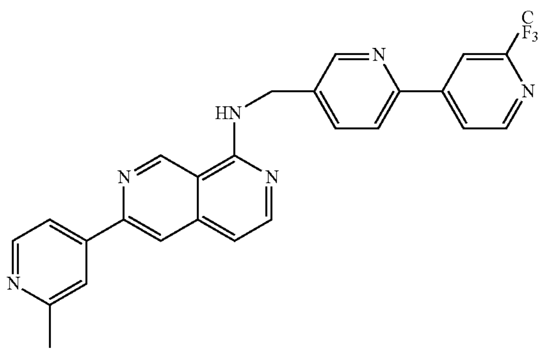 [SMILES: Cc1cc(-c2cc3ccnc(NCc4ccc(-c5ccnc(C(F)(F)F)c5)nc4)c3cn2)ccn1] | MS m/z = 473.2 (M + 1); |
| 30 | 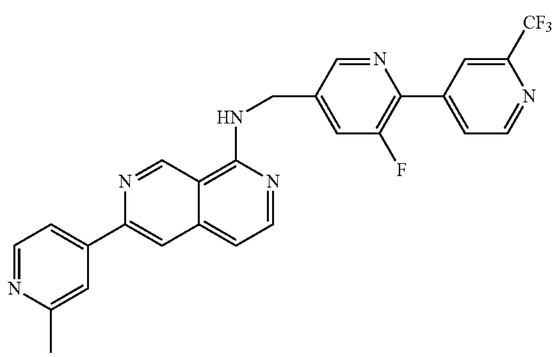 [SMILES: Cc1cc(-c2cc3ccnc(NCc4cnc(-c5ccnc(C(F)(F)F)c5)c(F)c4)c3cn2)ccn1] | MS m/z = 497.2 (M + 1); |
| 31 | 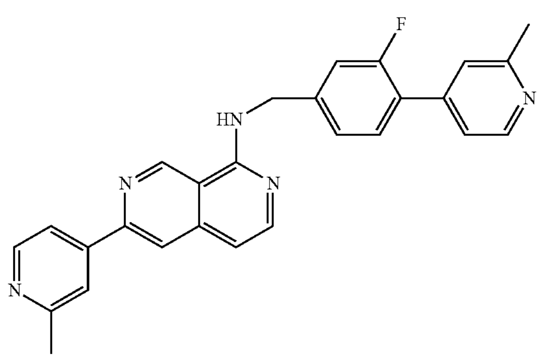 [SMILES: Cc1cc(-c2cc3ccnc(NCc4ccc(-c5ccnc(C)c5)c(F)c4)c3cn2)ccn1] | MS m/z = 436.2 (M + 1); $^1$H NMR (300 MHz, CDCl$_3$): δ2.63 (s, 3H), 2.70 (s, 3H), 4.96 (d, J = 5.70 Hz, 2H), 6.02 (br, 1H), 7.02 (d, J = 5.70 Hz, 1H), 7.34 (s, 1H), 7.45 (d, J = 7.80 Hz, 2H), 7.61 (s, 1H), 7.78 (d, J = 4.80 Hz, 2H), 7.88 (s, 1H), 7.98 (s, 1H), 8.22 (d, J = 5.70 Hz, 1H), 8.55 (d, J = 5.10 Hz, 2H), 8.64 (d, J = 5.10 Hz, 2H), 9.34 (s, 1H). |

TABLE 1-continued

Compound Table

| No. | Compound Structure | Compound physical characterization |
|---|---|---|
| 32 | 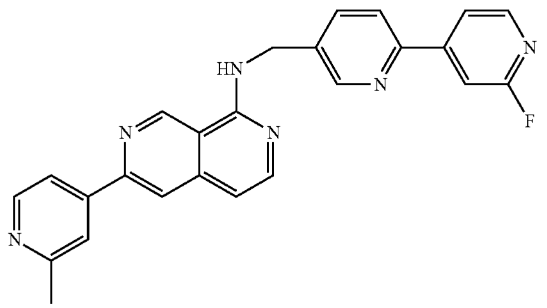 | MS m/z = 423.2 (M + 1); |
| 33 | 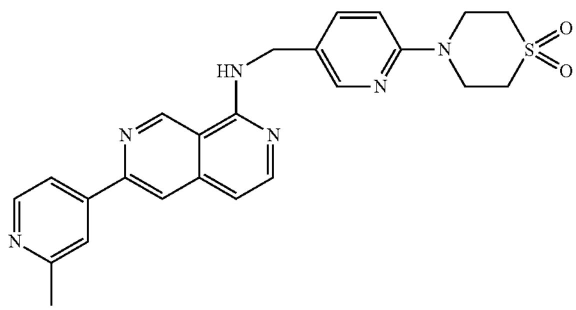 [SMILES: Cc1cc(-c2cc3ccnc(NCc4ccc(N5CCS(=O)(=O)CC5)nc4)c3cn2)ccn1] | MS m/z = 461.2 (M + 1); $^1$H NMR (300 MHz, CDCl$_3$): δ2.69 (s, 3H), 3.06 (t, 4H), 4.18 (t, 4H), 4.79 (d, J = 5.40 Hz, 2H), 5.85 (br, 1H), 6.76 (d, J = 8.70 Hz, 1H), 6.99 (d, J = 6.00 Hz, 1H), 7.69 (q, 1H), 7.76 (q, 1H), 7.86 (s, 1H), 7.96 (s, 1H), 8.22 (d, J = 6.00 Hz, 1H), 8.31 (s, 1H), 8.63 (d, J = 5.40 Hz, 1H), 9.27 (s, 1H). |
| 34 | 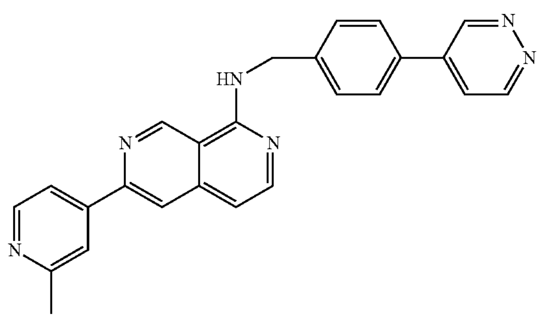 [SMILES: Cc1cc(-c2cc3ccnc(NCc4ccc(-c5ccnnc5)cc4)c3cn2)ccn1] | MS m/z = 405.2 (M + 1); |
| 35 | 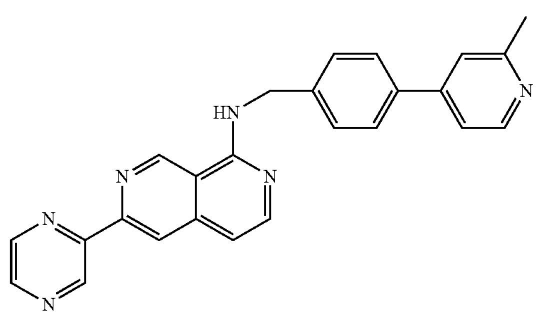 [SMILES: Cc1cc(-c2ccc(CNc3nccc4cc(-c5cnccn5)ncc34)cc2)ccn1] | MS m/z = 405.2 (M + 1); $^1$H NMR (300 MHz, CDCl$_3$): δ2.64 (s, 3H), 4.96 (d, J = 5.40 Hz, 2H), 5.96 (br, 1H), 7.05 (d, J = 5.70 Hz, 1H), 7.31 (m, 1H), 7.37 (s, 1H), 7.56 (d, J = 8.40 Hz, 2H), 7.64 (d, J = 8.40 Hz, 2H), 8.23 (d, J = 5.70 Hz, 1H), 8.54 (d, J = 5.40 Hz, 1H), 8.57 (s, 1H), 8.64 (d, J = 2.40 Hz, 1H), 8.67 (m, 1H), 9.32 (s, 1H), 9.71 (d, J = 1.50 Hz, 1H). |
| 36 | 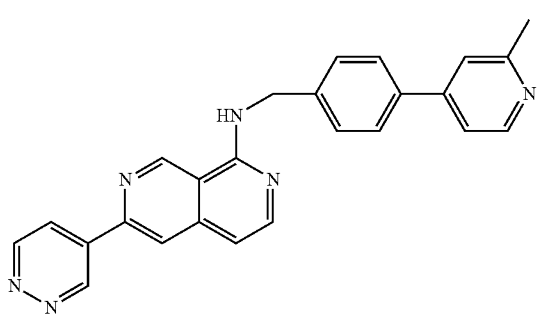 [SMILES: Cc1cc(-c2ccc(CNc3nccc4cc(-c5ccnnc5)ncc34)cc2)ccn1] | MS m/z = 405.2 (M + 1); |

TABLE 1-continued

Compound Table

| No. | Compound Structure | Compound physical characterization |
|---|---|---|
| 37 | 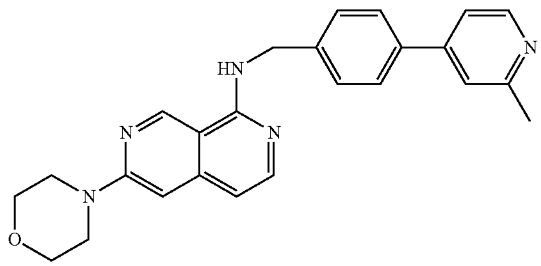 [SMILES: Cc1cc(-c2ccc(CNc3nccc4cc(N5CCOCC5)ncc34)cc2)ccn1] | MS m/z = 412.2 (M + 1); |
| 38 | 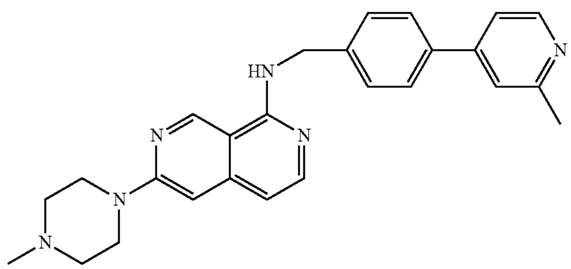 | MS m/z = 425.2 (M + 1); |
| 39 | 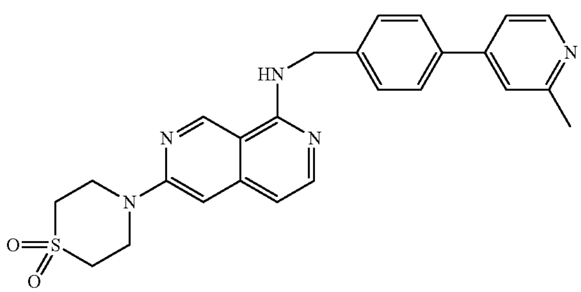 [SMILES: Cc1cc(-c2ccc(CNc3nccc4cc(N5CCS(=O)(=O)CC5)ncc34)cc2)ccn1] | MS m/z = 460.2 (M + 1); $^1$H NMR (300 MHz, CD$_3$OD): δ2.56 (s, 3H), 3.13 (t, 4H), 4.28 (t, 4H), 4.81 (s, 2H), 6.79 (d, J = 6.30 Hz, 1H), 6.99 (s, 1H), 7.47 (m, 2H), 7.51 (s, 1H), 7.55 (d, J = 6.60 Hz, 2H), 7.71 (d, J = 8.40 Hz, 2H), 8.38 (d, J = 5.40 Hz, 1H), 9.27 (s, 1H). |
| 40 | 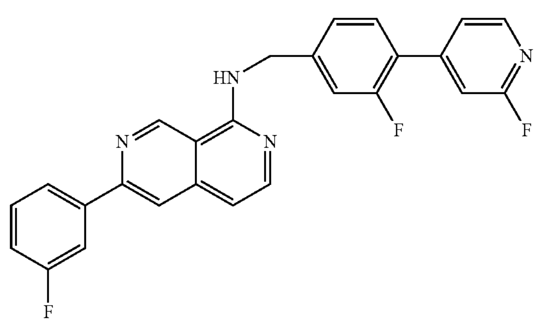 [SMILES: Fc1cccc(-c2cc3ccnc(NCc4ccc(-c5ccnc(F)c5)c(F)c4)c3cn2)c1] | MS M/z = 443.2 (M + 1); |
| 41 | 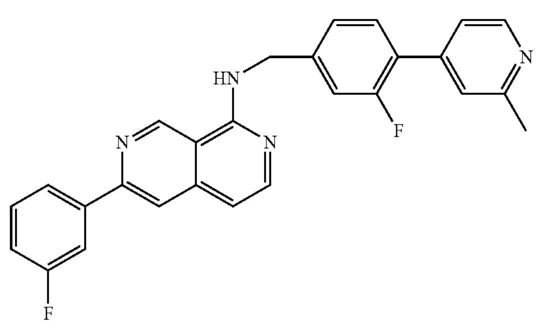 [SMILES: Cc1cc(-c2ccc(CNc3nccc4cc(-c5cccc(F)c5)ncc34)cc2F)ccn1] | MS m/z = 439.2 (M + 1); |

TABLE 1-continued

Compound Table

| No. | Compound Structure | Compound physical characterization |
|---|---|---|
| 42 | 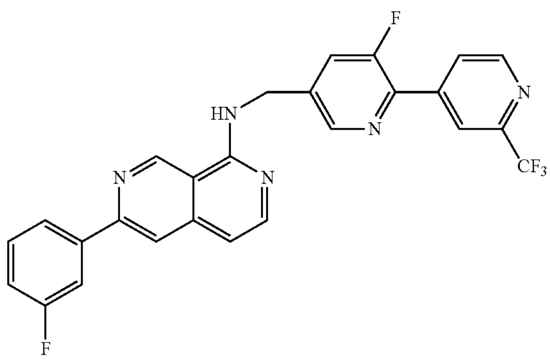 [SMILES: Fc1cccc(-c2cc3ccnc(NCc4cnc(-c5ccnc(C(F)(F)F)c5)c(F)c4)c3cn2)c1] | MS m/z = 494.2 (M + 1); |
| 43 | 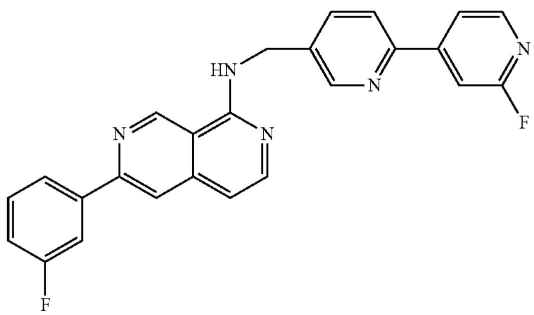 [SMILES: Fc1cccc(-c2cc3ccnc(NCc4ccc(-c5ccnc(F)c5)nc4)c3cn2)c1] | MS m/z = 426.2 (M + 1); |
| 44 | 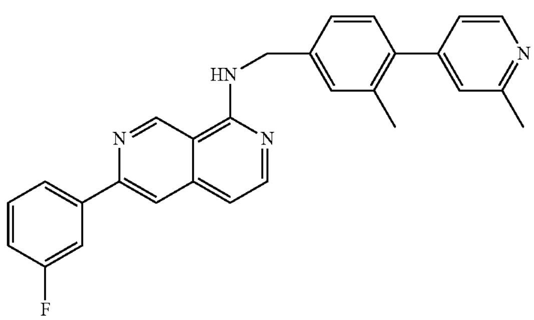 [SMILES: Cc1cc(-c2ccc(CNc3nccc4cc(-c5cccc(F)c5)ncc34)cc2C)ccn1] | MS m/z = 435.2 (M + 1); |
| 45 | 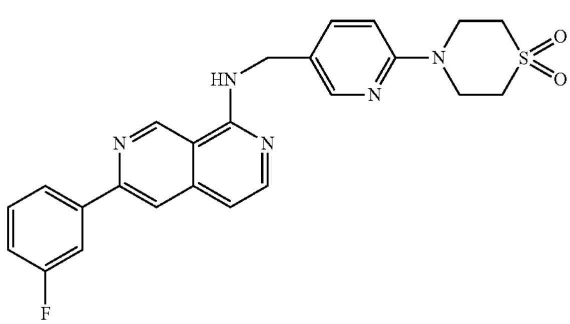 [SMILES: O=S1(=O)CCN(c2ccc(CNc3nccc4cc(-c5cccc(F)c5)ncc34)cn2)CC1] | MS m/z = 464.2 (M + 1); |

TABLE 1-continued

Compound Table

| No. | Compound Structure | Compound physical characterization |
|---|---|---|
| 46 | 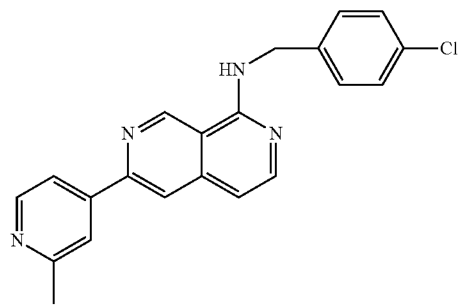 [SMILES: Cc1cc(-c2cc3ccnc(NCc4ccc(Cl)cc4)c3cn2)ccn1] | MS m/z = 361.2 (M + 1); |
| 47 | 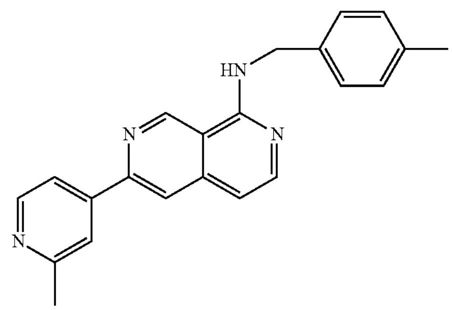 [SMILES: Cc1ccc(CNc2nccc3cc(-c4ccnc(C)c4)ncc23)cc1] | MS m/z = 341.1 (M + 1); $^1$H NMR (300 MHz, CD$_3$OD): δ2.31 (s, 3H), 2.65 (s, 3H), 4.76 (s, 2H), 6.98 (m, 1H), 7.12 (d, J = 7.80 Hz, 2H), 7.28 (d, J = 8.10 Hz, 2H), 7.92 (m, 1H), 8.03 (m, 2H), 8.17 (s, 1H), 8.52 (d, J = 5.40 Hz, 1H), 9.56 (s, 1H). |
| 48 | 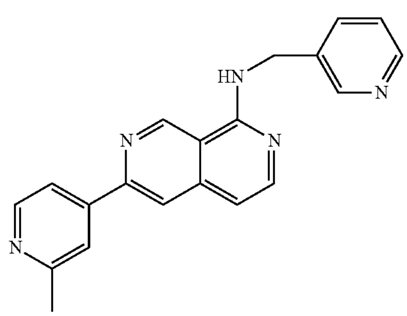 [SMILES: Cc1cc(-c2cc3ccnc(NCc4cccnc4)c3cn2)ccn1] | MS m/z = 328.1 (M + 1); |
| 49 | 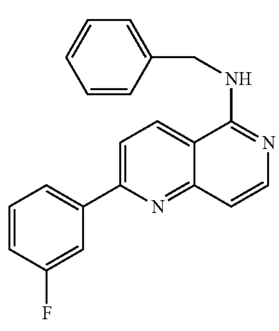 [SMILES: Fc1cccc(-c2ccc3c(NCc4ccccc4)nccc3n2)c1] | MS m/z = 330.1 (M + 1); |

TABLE 1-continued

Compound Table

| No. | Compound Structure | Compound physical characterization |
|---|---|---|
| 50 | 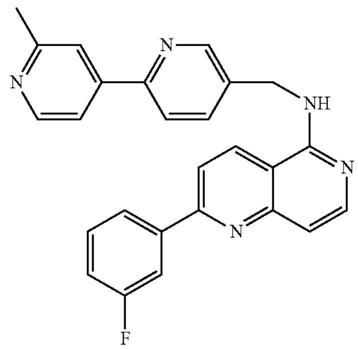 [SMILES: Cc1cc(-c2ccc(CNc3nccc4nc(-c5cccc(F)c5)ccc34)cn2)ccn1] | MS m/z = 422.2 (M + 1); ¹H NMR (400 MHz, DMSO-d6) δ 8.96 (d, J = 8.4 Hz, 1H), 8.87 (s, 1H), 8.76 (d, J = 6.0 Hz, 1H), 802-8.37 (m, 8H), 7.61-7.67 (m, 1H), 7.42 (t, J = 8.0 Hz, 1H), 7.19 (d, J = 6.4 Hz, 1H), 5.76 (s, 1H), 4.93 (d, J = 5.6 Hz, 2H), 2.69 (s, 3H). |
| 51 | 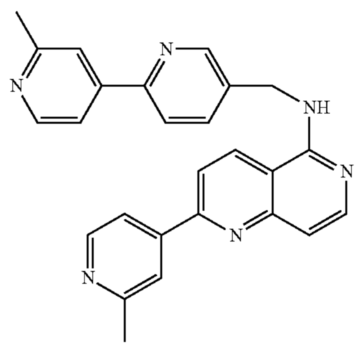 [SMILES: Cc1cc(-c2ccc(CNc3nccc4nc(-c5ccnc(C)c5)ccc34)cn2)ccn1] | MS m/z = 419.2 (M + 1); |
| 52 | 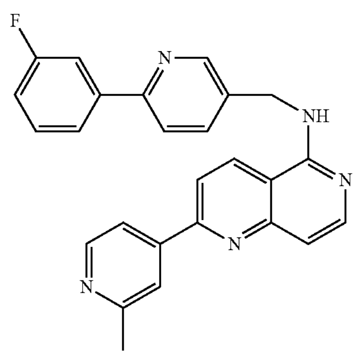 [SMILES: Cc1cc(-c2ccc3c(NCc4ccc(-c5cccc(F)c5)nc4)nccc3n2)ccn1] | MS m/z = 422.2 (M + 1); |
| 53 | 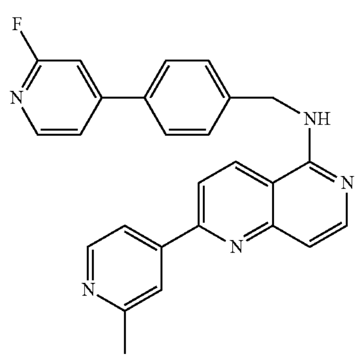 [SMILES: Cc1cc(-c2ccc3c(NCc4ccc(-c5ccnc(F)c5)cc4)nccc3n2)ccn1] | MS M/z = 422.2 (M + 1); |

TABLE 1-continued

Compound Table

| No. | Compound Structure | Compound physical characterization |
|---|---|---|
| 54 | 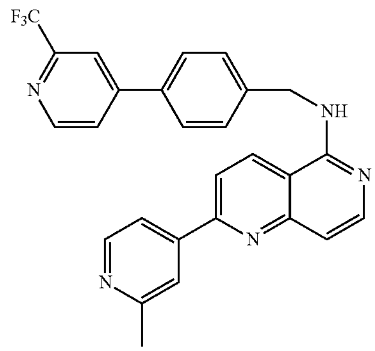 [SMILES: Cc1cc(-c2ccc3c(NCc4ccc(-c5ccnc(C(F)(F)F)c5)cc4)nccc3n2)ccn1] | MS m/z = 472.2 (M + 1); |
| 55 | 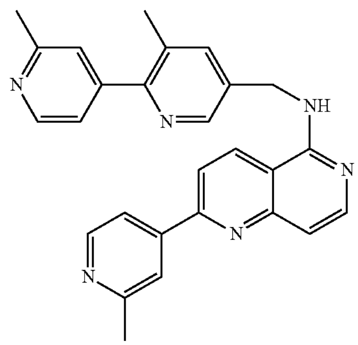 [SMILES: Cc1cc(-c2ccc3c(NCc4cnc(-c5ccnc(C)c5)c(C)c4)nccc3n2)ccn1] | MS m/z = 433.2 (M + 1); |
| 56 | 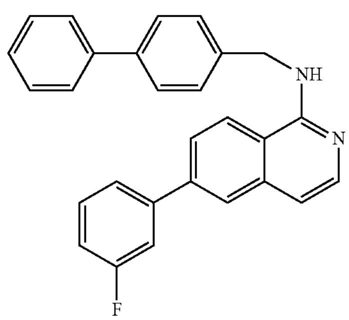 [SMILES: Fc1cccc(-c2ccc3c(NCc4ccc(-c5ccccc5)cc4)nccc3c2)c1] | MS m/z = 405.2 (M + 1); |
| 57 | 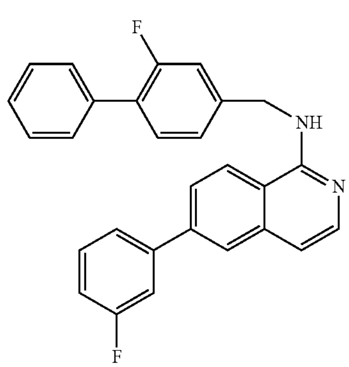 [SMILES: Fc1cccc(-c2ccc3c(NCc4ccc(-c5ccccc5)c(F)c4)nccc3c2)c1] | MS m/z = 423.2 (M + 1); |

TABLE 1-continued

Compound Table

| No. | Compound Structure | Compound physical characterization |
|---|---|---|
| 58 | 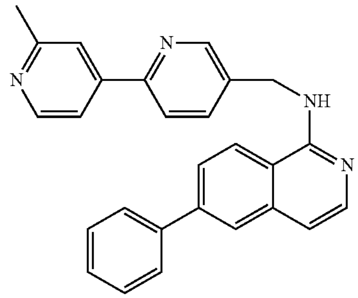 [SMILES: Cc1cc(-c2ccc(CNc3nccc4cc(-c5ccccc5)ccc34)cn2)ccn1] | MS m/z = 403.2 (M + 1); |
| 59 | 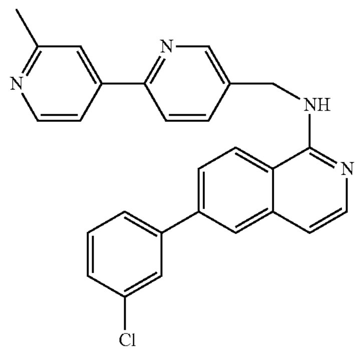 [SMILES: Cc1cc(-c2ccc(CNc3nccc4cc(-c5cccc(Cl)c5)ccc34)cn2)ccn1] | MS m/z = 437.2 (M + 1); |
| 60 | 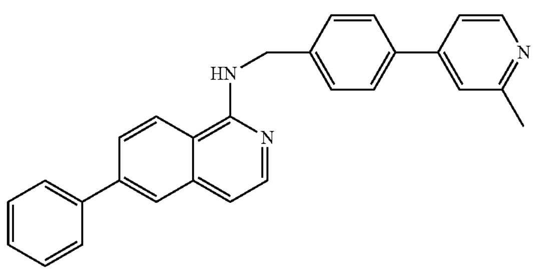 [SMILES: Cc1cc(-c2ccc(CNc3nccc4cc(-c5ccccc5)ccc34)cc2)ccn1] | MS m/z = 402.2 (M + 1); |
| 61 | 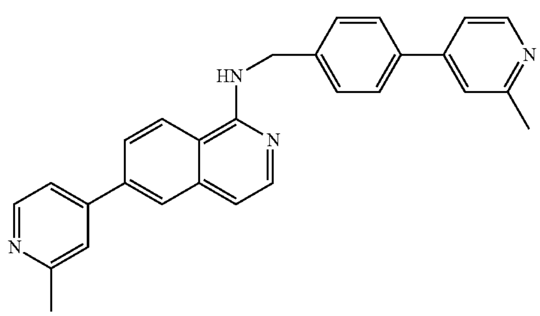 | MS m/z = 417.2 (M + 1); 1HNMR (300 MHz, CDCl3): δ2.45 (s, 3H), 2.64 (s, 3H), 4.94 (d, J = 5.10 Hz, 2H), 5.93 (br, 1H), 7.00 (d, J = 5.70 Hz, 1H), 7.32 (d, J = 5.10 Hz, 1H), 7.36 (s, 1H), 7.54 (d, J = 8.10 Hz, 1H), 7.63 (d, J = 8.10 Hz, 2H), 7.80 (m, 2H), 8.20 (d, J = 6.00 Hz, 1H), 8.21 (s, 1H), 8.53 (m, 2H), 9.10 (s, 1H), 9.31 (s, 1H). |
| 62 | 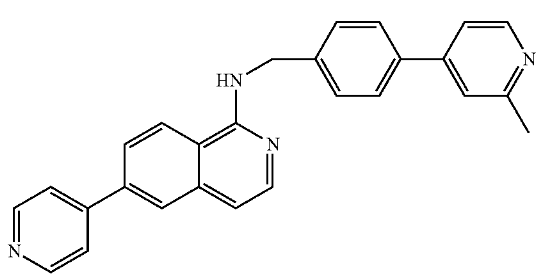 [SMILES: Cc1cc(-c2ccc(CNc3nccc4cc(-c5ccncc5)ccc34)cc2)ccn1] | MS m/z = 403.2 (M + 1); |

TABLE 1-continued

Compound Table

| No. | Compound Structure | Compound physical characterization |
|---|---|---|
| 63 | 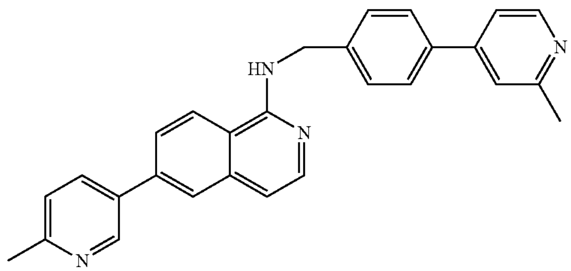 | MS m/z = 417.2 (M + 1); $^1$H NMR (300 MHz, CDCl$_3$): δ2.63 (s, 3H), 2.65 (s, 3H), 4.93 (d, J = 5.10 Hz, 2H), 7.06 (d, J = 6.00 Hz, 1H), 7.30 (m, 2H), 7.37 (s, 1H), 7.55 (d, J = 8.10 Hz, 2H), 7.63 (d, J = 8.10 Hz, 2H), 7.67 (m, 1H), 7.88 (m, 3H), 8.07 (d, J = 6.00 Hz, 1H), 8.53 (d, J = 5.10 Hz, 1H), 8.82 (d, J = 2.40 Hz, 1H). |
| 64 | 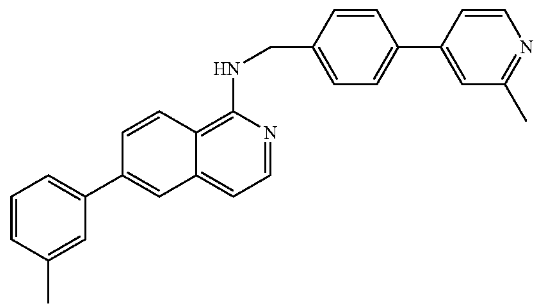 [SMILES: Cc1cccc(-c2ccc3c(NCc4ccc(-c5ccnc(C)c5)cc4)nccc3c2)c1] | MS m/z = 416.2 (M + 1); |
| 65 | 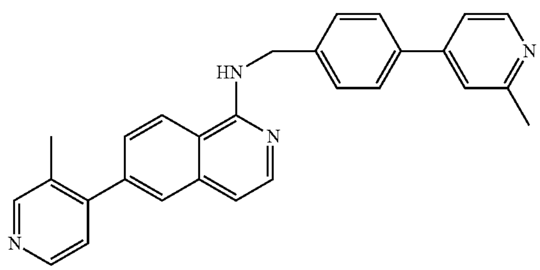 [SMILES: Cc1cc(-c2ccc(CNc3nccc4cc(-c5ccncc5C)ccc34)cc2)ccn1] | MS m/z = 417.2 (M + 1); |
| 66 | 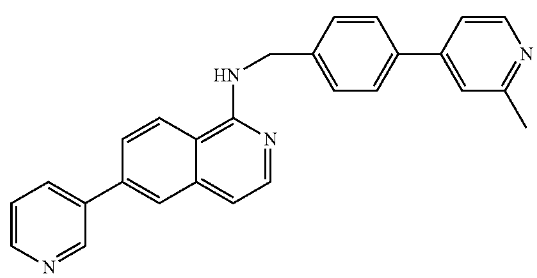 [SMILES: Cc1cc(-c2ccc(CNc3nccc4cc(-c5cccnc5)ccc34)cc2)ccn1] | MS m/z = 403.2 (M + 1); |
| 67 | 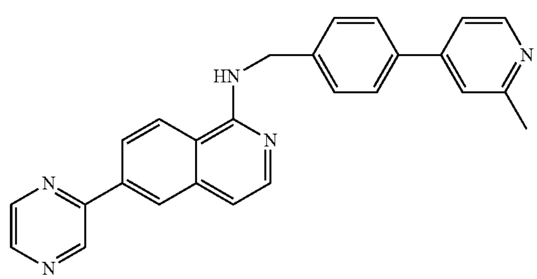 [SMILES: Cc1cc(-c2ccc(CNc3nccc4cc(-c5cnccn5)ccc34)cc2)ccn1] | MS m/z = 404.2 (M + 1); |

TABLE 1-continued

Compound Table

| No. | Compound Structure | Compound physical characterization |
|---|---|---|
| 68 | 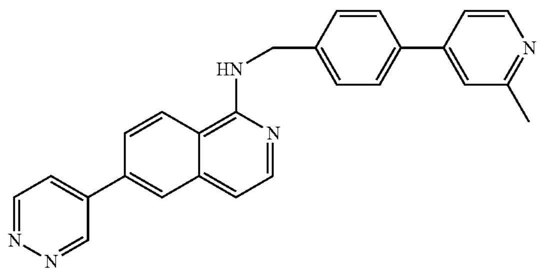 [SMILES: Cc1cc(-c2ccc(CNc3nccc4cc(-c5ccnnc5)ccc34)cc2)ccn1] | MS m/z = 404.2 (M + 1); |
| 69 | 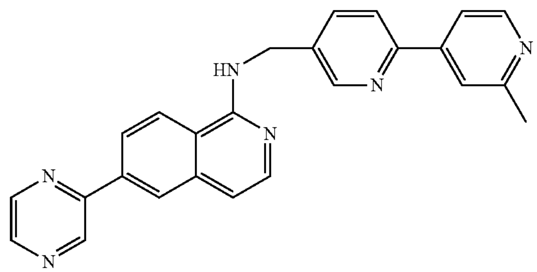 [SMILES: Cc1cc(-c2ccc(CNc3nccc4cc(-c5cnccn5)ccc34)cn2)ccn1] | MS m/z = 405.2 (M + 1); ¹H NMR (400 MHz, DMSO-d6) δ 9.52 (d, J = 1.2 Hz, 1H), 8.92 (d, J = 2.0 Hz, 1H), 8.84-8.86 (m, 1H), 8.75-8.82 (m, 4H), 8.56 (d, J = 8.8 Hz, 1H), 8.42 (s, 1H), 8.31 (d, J = 8.8 Hz, 2H), 8.12 (d, J = 8.0 Hz, 1H), 7.78 (d, J = 6.8 Hz, 1H), 7.40 (d, J = 6.8 Hz, 1H), 5.76 (s, 1H), 5.00 (d, J = 5.6 Hz, 2H), 2.73 (s, 1H). |
| 70 | 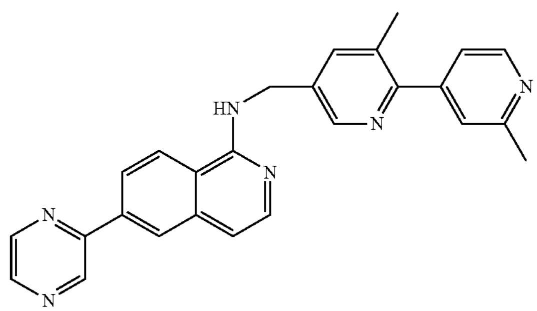 [SMILES: Cc1cc(-c2ncc(CNc3nccc4cc(-c5cnccn5)ccc34)cc2C)ccn1] | MS m/z = 419.2 (M + 1); |
| 71 | 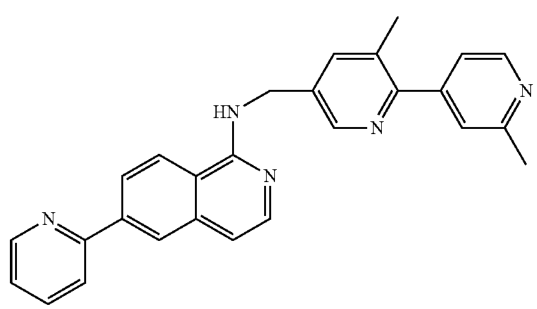 [SMILES: Cc1cc(-c2ncc(CNc3nccc4cc(-c5ccccn5)ccc34)cc2C)ccn1] | MS m/z = 418.2 (M + 1); |
| 72 | 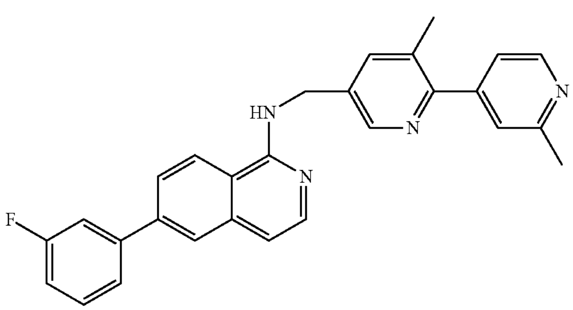 [SMILES: Cc1cc(-c2ncc(CNc3nccc4cc(-c5cccc(F)c5)ccc34)cc2C)ccn1] | MS m/z = 435.2 (M + 1); |

TABLE 1-continued

Compound Table

| No. | Compound Structure | Compound physical characterization |
|---|---|---|
| 73 | 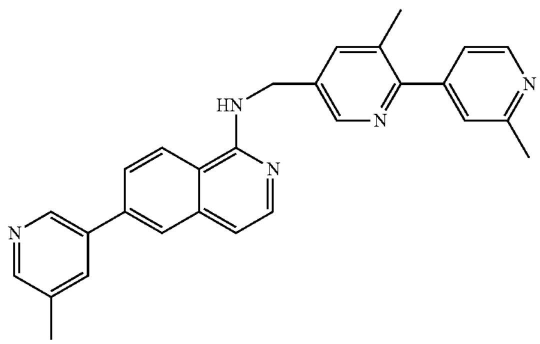 [SMILES: Cc1cncc(-c2ccc3c(NCc4cnc(-c5ccnc(C)c5)c(C)c4)nccc3c2)c1] | MS m/z = 432.2 (M + 1); |
| 74 | 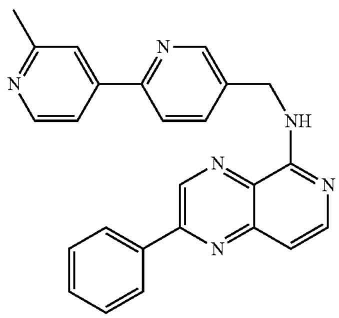 [SMILES: Cc1cc(-c2ccc(CNc3nccc4nc(-c5ccccc5)cnc34)cn2)ccn1] | MS m/z = 405.2 (M + 1); |
| 75 | 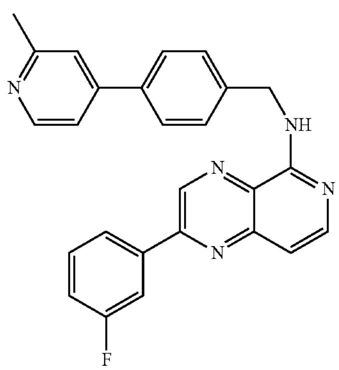 [SMILES: Cc1cc(-c2ccc(CNc3nccc4nc(-c5cccc(F)c5)cnc34)cc2)ccn1] | MS m/z = 422.2 (M + 1); |
| 76 | 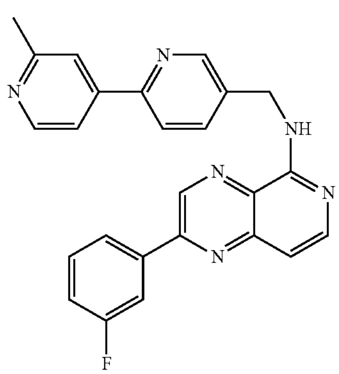 [SMILES: Cc1cc(-c2ccc(CNc3nccc4nc(-c5cccc(F)c5)cnc34)cn2)ccn1] | MS m/z = 423.2 (M + 1); |

TABLE 1-continued

Compound Table

| No. | Compound Structure | Compound physical characterization |
|---|---|---|
| 77 | 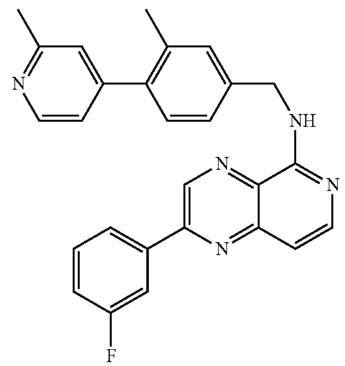 [SMILES: Cc1cc(-c2ccc(CNc3nccc4nc(-c5cccc(F)c5)cnc34)cc2C)ccn1] | MS m/z = 436.2 (M + 1); |
| 78 | 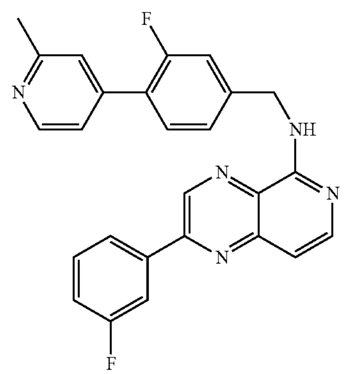 [SMILES: Cc1cc(-c2ccc(CNc3nccc4nc(-c5cccc(F)c5)cnc34)cc2F)ccn1] | MS m/z = 440.2 (M + 1); |
| 79 | 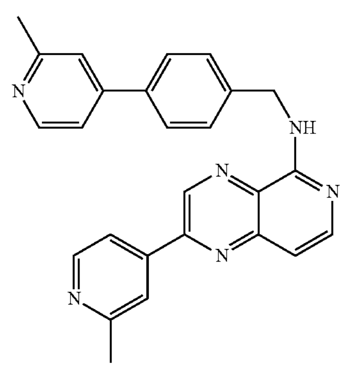 [SMILES: Cc1cc(-c2ccc(CNc3nccc4nc(-c5ccnc(C)c5)cnc34)cc2)ccn1] | MS m/z = 419.2 (M + 1); |
| 80 | 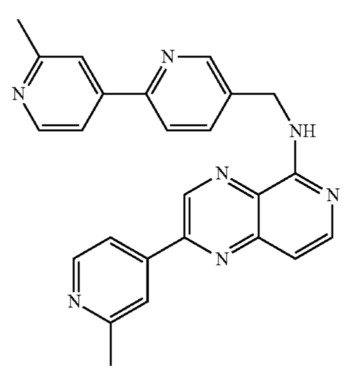 [SMILES: Cc1cc(-c2ccc(CNc3nccc4nc(-c5ccnc(C)c5)cnc34)cn2)ccn1] | MS m/z = 420.2 (M + 1); |

TABLE 1-continued

Compound Table

| No. | Compound Structure | Compound physical characterization |
|---|---|---|
| 81 | 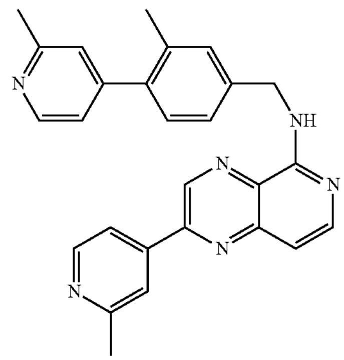 [SMILES: Cc1cc(-c2cnc3c(NCc4ccc(-c5ccnc(C)c5)c(C)c4)nccc3n2)ccn1] | MS m/z = 433.2 (M + 1); |
| 82 | 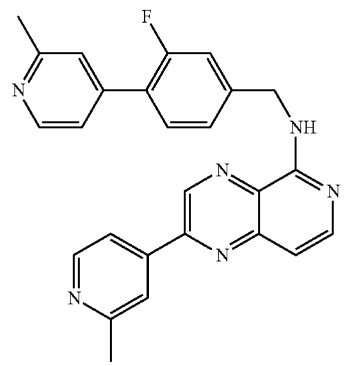 [SMILES: Cc1cc(-c2cnc3c(NCc4ccc(-c5ccnc(C)c5)c(F)c4)nccc3n2)ccn1] | MS m/z = 437.2 (M + 1); |
| 83 | 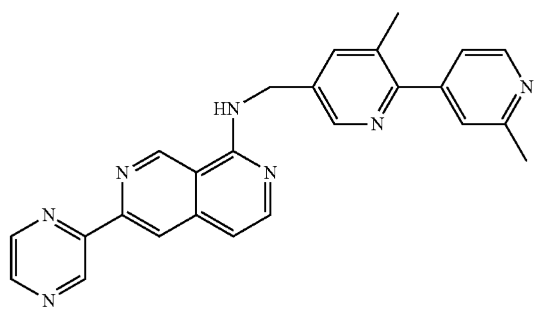 | MS m/z = 420.2 (M + 1); |
| 84 | 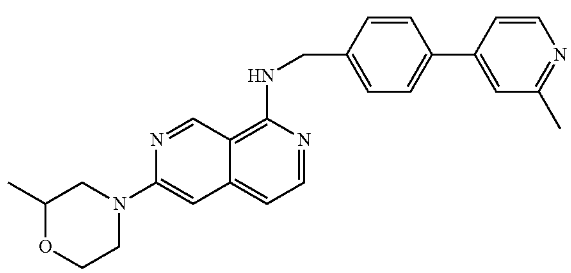 | MS m/z = 426.2 (M + 1); |
| 85 | 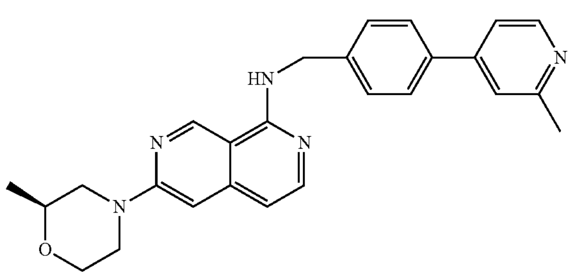 | MS m/z = 426.2 (M + 1); |

TABLE 1-continued

| No. | Compound Structure | Compound physical characterization |
|---|---|---|
| 86 | 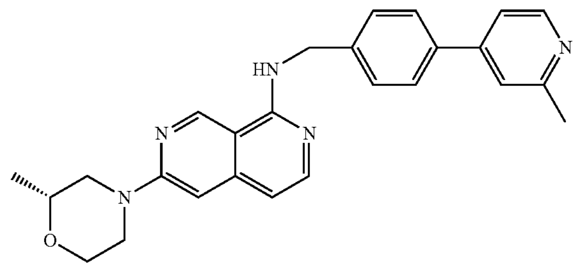 | MS m/z = 426.2 (M + 1); |
| 87 | 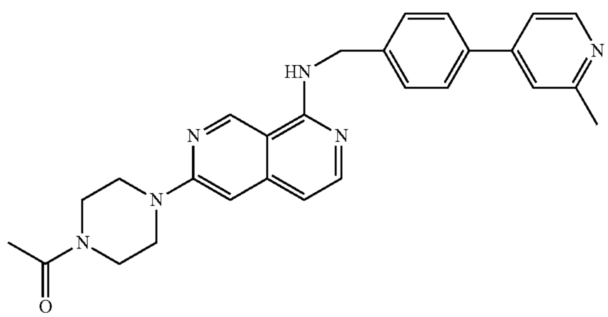 [SMILES: CC(=O)N1CCN(c2cc3ccnc(NCc4ccc(-c5ccnc(C)c5)cc4)c3cn2)CC1] | MS m/z = 453.2 (M + 1); |
| 88 | 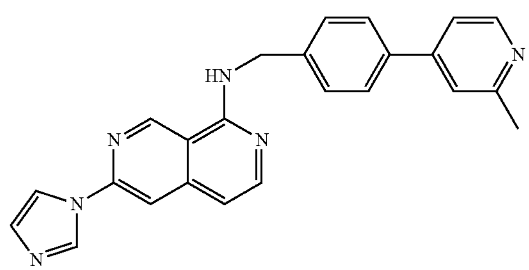 [SMILES: Cc1cc(-c2ccc(CNc3nccc4cc(-n5ccnc5)ncc34)cc2)ccn1] | MS m/z = 393.1 (M + 1); |
| 89 | 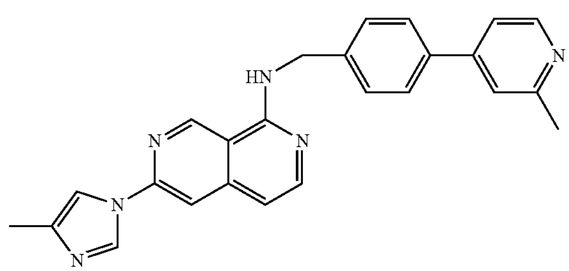 | MS m/z = 407.2 (M + 1); |
| 90 | 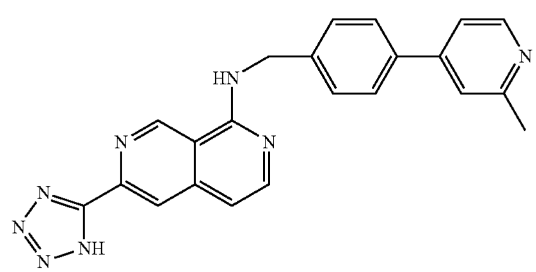 [SMILES: Cc1cc(-c2ccc(CNc3nccc4cc(-c5nnn[nH]5)ncc34)cc2)ccn1] | MS m/z = 395.1 (M + 1); |

TABLE 1-continued

Compound Table

| No. | Compound Structure | Compound physical characterization |
|---|---|---|
| 91 | 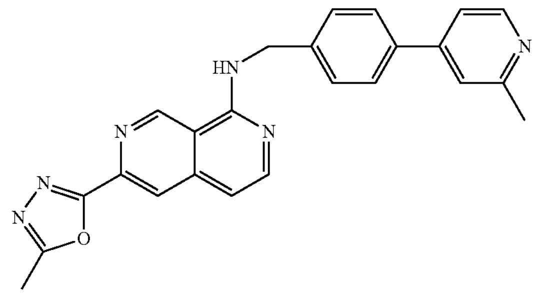 [SMILES: Cc1cc(-c2ccc(CNc3nccc4cc(-c5nnc(C)o5)ncc34)cc2)ccn1] | MS m/z = 409.2 (M + 1); |
| 92 | 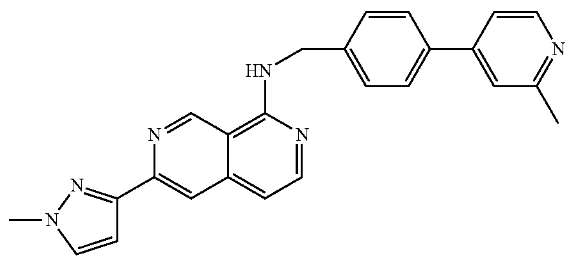 | MS m/z = 407.2 (M + 1); |
| 93 | 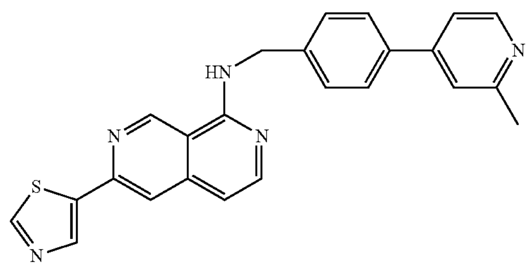 [SMILES: Cc1cc(-c2ccc(CNc3nccc4cc(-c5cncs5)ncc34)cc2)ccn1] | MS m/z = 410.2 (M + 1); |
| 94 | 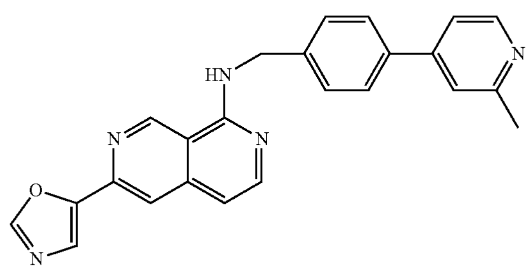 [SMILES: Cc1cc(-c2ccc(CNc3nccc4cc(-c5cnco5)ncc34)cc2)ccn1] | MS m/z = 394.1 (M + 1); |
| 95 | 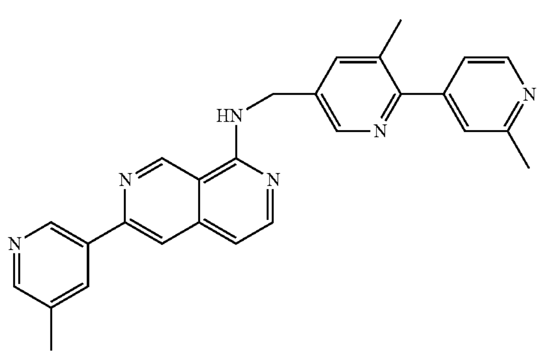 [SMILES: Cc1cncc(-c2cc3ccnc(NCc4cnc(-c5ccnc(C)c5)c(C)c4)c3cn2)c1] | MS m/z = 433.2 (M + 1); |

TABLE 1-continued

Compound Table

| No. | Compound Structure | Compound physical characterization |
|---|---|---|
| 96 | 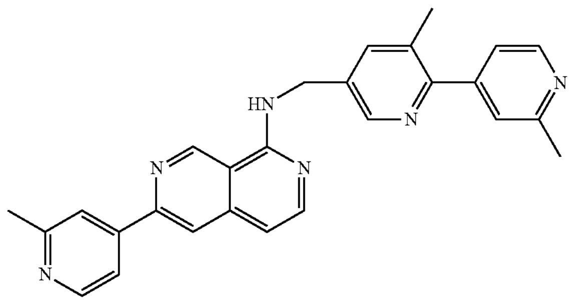 | MS m/z = 433.2 (M + 1); 1H NMR (300 MHz, CDCl3): δ2.30 (s, 3H), 2.55 (s, 3H), 2.61 (s, 3H), 4.86 (d, J = 5.4 Hz, 2H), 5.98 (br, 1H), 6.94 (d, J = 5.7 Hz, 1H), 7.17 (m, 1H), 7.24 (s, 1H), 7.61 (s, 1H), 7.70 (d, J = 5.1 Hz, 1H), 7.79 (s, 1H), 7.89 (s, 1H), 8.14 (d, J = 6.0 Hz, 1H), 8.49 (d, J = 5.1 Hz, 1H), 8.56 (m, 2H), 9.25 (s, 1H). |
| 97 | 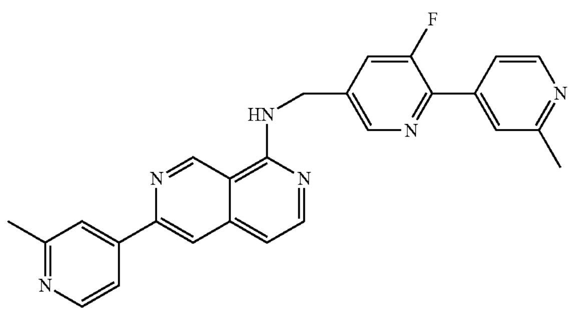 | MS m/z = 437.2 (M + 1); $^1$H NMR (300 MHz, CDCl3): δ2.31 (s, 3H), 2.61 (s, 3H), 4.90 (d, J = 5.4 Hz, 2H), 6.00 (br, 1H), 6.94 (d, J = 5.7 Hz, 1H), 7.18 (m, 1H), 7.24 (s, 1H), 7.63 (s, 1H), 7.70 (d, J = 5.1 Hz, 1H), 7.80 (s, 1H), 7.90 (s, 1H), 8.14 (d, J = 6.0 Hz, 1H), 8.33 (s, 1H), 8.50 (d, J = 5.1 Hz, 1H), 8.54 (m, 1H), 9.25 (s, 1H). |
| 98 | 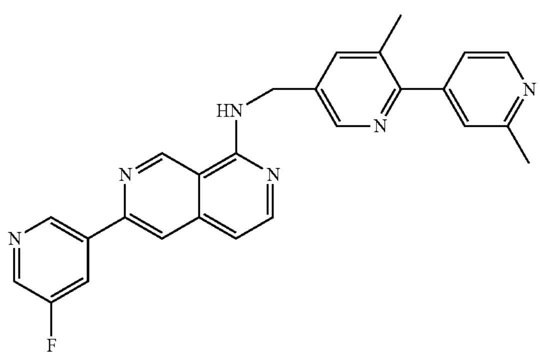 [SMILES: Cc1cc(-c2ncc(CNc3nccc4cc(-c5cncc(F)c5)ncc34)cc2C)ccn1] | MS m/z = 437.2 (M + 1); |
| 99 | 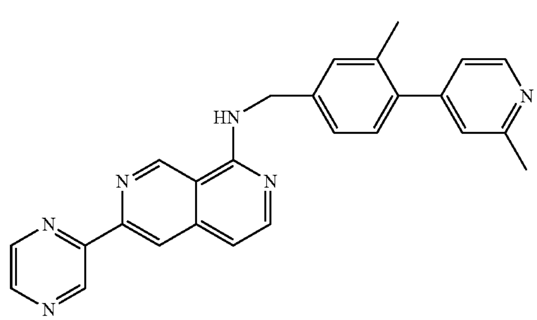 [SMILES: Cc1cc(-c2ccc(CNc3nccc4cc(-c5cnccn5)ncc34)cc2C)ccn1] | MS m/z = 419.2 (M + 1); |

TABLE 1-continued

Compound Table

| No. | Compound Structure | Compound physical characterization |
|---|---|---|
| 100 | 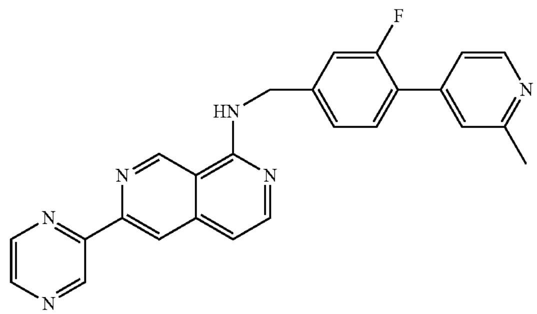 [SMILES: Cc1cc(-c2ccc(CNc3nccc4cc(-c5cnccn5)ncc34)cc2F)ccn1] | MS m/z = 423.2 (M + 1); |
| 101 | 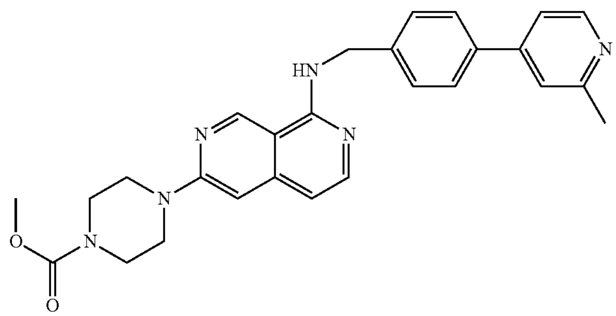 [SMILES: COC(=O)N1CCN(c2cc3ccnc(NCc4ccc(-c5ccnc(C)c5)cc4)c3cn2)CC1] | MS m/z = 469.2 (M + 1); |
| 102 | 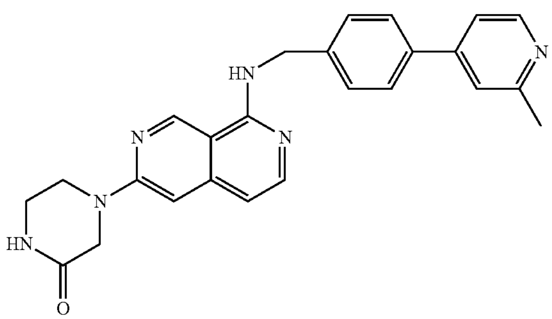 [SMILES: Cc1cc(-c2ccc(CNc3nccc4cc(N5CCNC(=O)C5)ncc34)cc2)ccn1] | MS m/z = 425.2 (M + 1); |
| 103 | 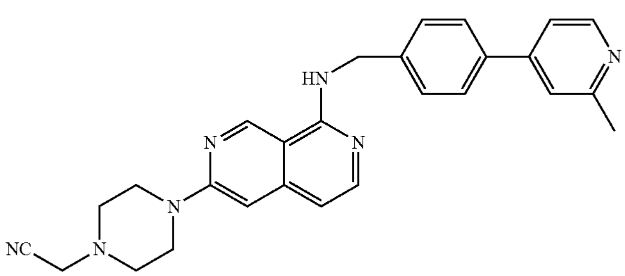 [SMILES: Cc1cc(-c2ccc(CNc3nccc4cc(N5CCN(CC#N)CC5)ncc34)cc2)ccn1] | MS m/z = 450.2 (M + 1); |
| 104 | 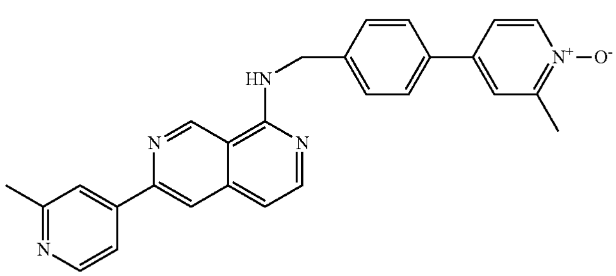 [SMILES: Cc1cc(-c2cc3ccnc(NCc4ccc(-c5cc[n+]([O-])c(C)c5)cc4)c3cn2)ccn1] | MS m/z = 434.2 (M + 1); |

TABLE 1-continued

Compound Table

| No. | Compound Structure | Compound physical characterization |
|---|---|---|
| 105 | 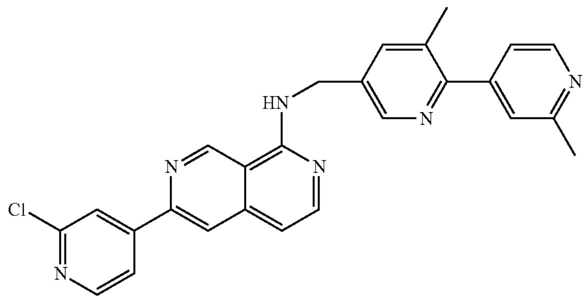 [SMILES: Cc1cc(-c2ncc(CNc3nccc4cc(-c5ccnc(Cl)c5)ncc34)cc2C)ccn1] | MS m/z = 453.2 (M + 1); |
| 106 | 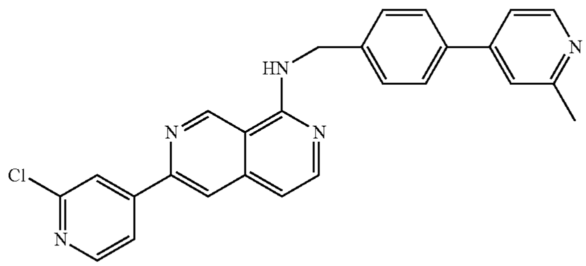 [SMILES: Cc1cc(-c2ccc(CNc3nccc4cc(-c5ccnc(Cl)c5)ncc34)cc2)ccn1] | MS m/z = 438.2 (M + 1); |
| 107 | 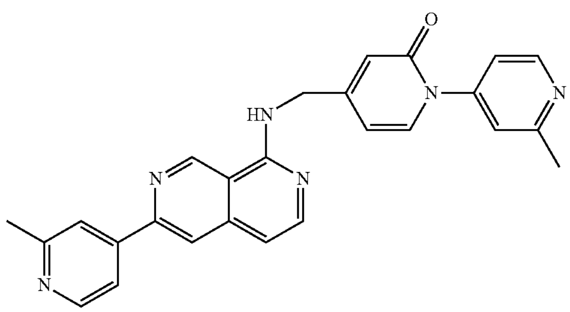 | MS m/z = 435.2 (M + 1): |
| 108 | 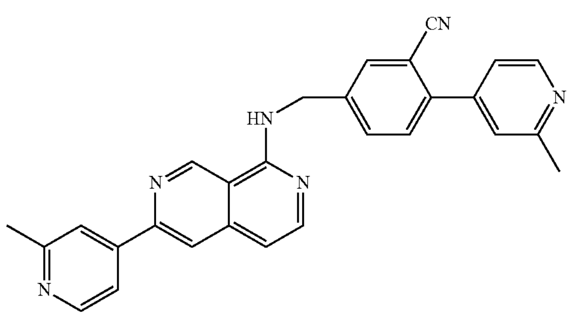 | MS m/z = 443.2 (M + 1); $^1$H NMR (300 MHz, CDCl3): δ2.30 (s, 3H), 2.61 (s, 3H), 4.98 (d, J = 5.7 Hz, 2H), 6.00 (br, 1H), 7.03 (d, J = 5.70 Hz, 1H), 7.35 (s, 1H), 7.45 (d, J = 7.8 Hz, 2H), 7.62 (s, 1H), 7.79 (d, J = 5.1 Hz, 2H), 7.89 (s, 1H), 7.98 (s, 1H), 8.20 (d, J = 5.70 Hz, 1H), 8.56 (d, J = 5.10 Hz, 2H), 8.66 (d, J = 5.10 Hz, 2H), 9.30 (s, 1H). |
| 109 | 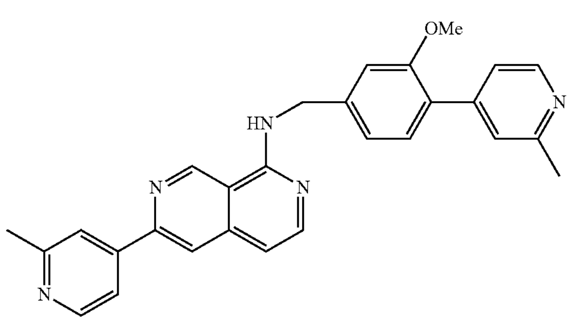 | MS m/z = 448.2 (M + 1); |

TABLE 1-continued

Compound Table

| No. | Compound Structure | Compound physical characterization |
|---|---|---|
| 110 | 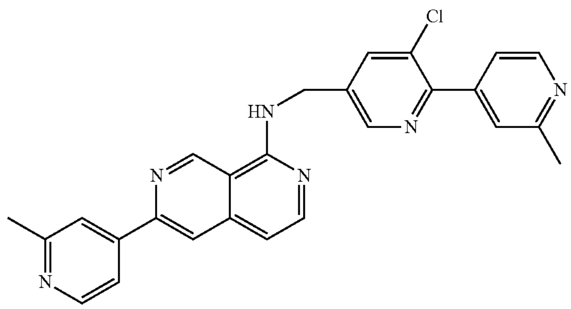 | MS m/z = 453.2 (M + 1); |
| 111 | 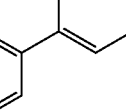 | MS m/z = 444.2 (M + 1); |
| 112 | 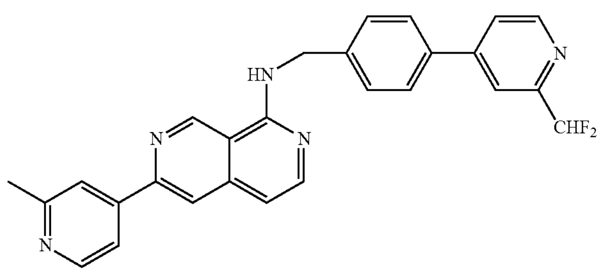 [SMILES: Cc1cc(-c2cc3ccnc(NCc4ccc(-c5ccnc(C(F)F)c5)cc4)c3cn2)ccn1] | MS m/z = 454.2 (M + 1); |

III. Medical and Pharmaceutical Uses

Compounds of the invention are indicated as pharmaceuticals. According to a further aspect of the invention there is provided a compound of the invention, as hereinbefore (but without any provisos, where applicable), for use as a pharmaceutical. There is also provided a synthetic form of a compound of the invention (but without any provisos, where applicable), for use as a pharmaceutical.

For the avoidance of doubt, although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolized in the body to form compounds of the invention. Such compounds (which may possess some pharmacological activity, provided that such activity is appreciably lower than that of the "active" compounds to which they are metabolized) may therefore be described as "prodrugs" of compounds of the invention.

By "prodrug of a compound of the invention", we include compounds that form a compound of the invention, in an experimentally-detectable amount, within a predetermined time (e.g. about 1 hour), following oral or parenteral administration. All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the "active" compounds of the invention to which they are metabolised), may also be described as "prodrugs".

Thus, the compounds of the invention are useful because they possess pharmacological activity, and/or are metabolised in the body following oral or parenteral administration to form compounds which possess pharmacological activity.

Compounds of the invention (as hereinbefore defined but without the proviso(s)) may be useful in the treatment of a cancer. By "cancer", we mean any disease that arises from an uncontrolled growth of cells (e.g. uncontrolled division), invasion (e.g. direct growth into adjacent tissue) or metastasis. By "uncontrolled growth", we include an increase in the number and/or size of cancer cells (also referred to herein as "proliferation"). By "metastasis" we mean the movement or migration (e.g. invasiveness) of cancer cells from a primary tumor site in the body of a subject to one or more other areas within the subject's body (where the cells can then form secondary tumors). Thus, in one embodiment the invention provides compounds and methods for inhibiting, in whole or in part, the formation of secondary tumors in a subject with cancer.

Advantageously, the compounds of the invention may be capable of inhibiting the proliferation and/or metastasis of cancer cells selectively.

By "selectively" we mean that the compounds of the invention may inhibit the proliferation and/or metastasis of cancer cells to a greater extent than it modulates the function (e.g. proliferation) of non-cancer cells. Preferably, the compounds of the invention inhibit the proliferation and/or metastasis of cancer cells only.

In another aspect, the present invention provides a pharmaceutical composition comprising the compound of the present invention and at least one pharmaceutically acceptable carrier or diluent, wherein said compound is in free form or in a pharmaceutically acceptable salt form. Such composition may be an oral composition, injectable composition or suppository. And the composition may be manufactured in a conventional manner by mixing, granulating or coating methods.

In an embodiment of the invention, the composition is an oral composition and it may be a tablet or gelatin capsule. Preferably, the oral composition comprises the present compound together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets, together with c) binders, e.g., magnesium aluminum silicate, starch paste, gelatin, tragamayth, methylcellulose, sodium carboxymethylcellulose and or polyvinylpyrrolidone; and if desired, d) disintegrants, e.g., starches, agar, alginic acid or its sodium salt, or effervescent mixtures; and/or e) additives, e.g., absorbents, colorants, flavors and sweeteners.

In another embodiment of the invention, the composition is an injectable composition, and may be an aqueous isotonic solution or suspension.

In yet another embodiment of the invention, the composition is a suppository and may be prepared from fatty emulsion or suspension.

Preferably, the composition is sterilized and/or contains adjuvant. Such adjuvant can be preserving, stabilizing, wetting or emulsifying agent, solution promoter, salt for regulating the osmotic pressure, buffer and/or any combination thereof.

Alternatively or in addition, the composition may further contain other therapeutically valuable substances for different applications, like solubilizers, stabilizers, tonicity enhancing agents, buffers and/or preservatives.

In an embodiment of the invention, the composition may be a formulation suitable for transdermal application. Such formulation includes an effective amount of the compound of the present invention and a carrier. Preferably, the carrier may include absorbable pharmacologically acceptable solvents to assist passage through the skin of the host. A transdermal device contain the formulation may also be used. The transdermal device may be in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Otherwise, a matrix transdermal formulation may also be used.

In another embodiment of the invention, the composition may be a formulation suitable for topical application, such as to the skin and eyes, and may be aqueous solution, ointment, cream or gel well known in the art.

In another aspect, the present invention provides a method of inhibiting WNT secretion from a cell.

In one embodiment, the cell is contained within a mammal, and the administered amount is a therapeutically effective amount. In another embodiment, the inhibition of WNT signaling further results in the inhibition of the growth of the cell. In a further embodiment, the cell is a cancer cell. In yet another embodiment, the cell is a fibrogenic cell.

Cell proliferation is measured by using methods known to those skilled in the art. For example, a convenient assay for measuring cell proliferation is the CellTiter-Glo™ Assay commercially available from Promega (Madison, Wis.). The assay procedure involves adding the CellTiter-Glo® reagent to cells cultured on multi-well dishes. The luminescent signal, measured by a luminometer or an imaging device, is proportional to the amount of ATP present, which is directly proportional to the number of viable cells present in culture. In addition, cell proliferation may also be measured using colony formation assays known in the art.

The present invention also provides a method for treating cancers or fibroses related to the WNT signaling pathway with an effective amount of the present compound. Those skilled in the art would readily be able to determine whether a cancer is related to the Wnt pathway by analyzing cancer cells using one of several techniques known in the art. For example, one could examine cancer cells for aberrations in the levels of proteins or mRNAs involved in Wnt signaling using immune and nucleic acid detection methods.

Cancers or fibroses related to the Wnt pathway include those in which activity of one or more components of the Wnt signaling pathways are upregulated from basal levels. In one embodiment, inhibiting the Wnt pathway may involve inhibiting Wnt secretion. As another example, inhibiting the Wnt pathway may involve inhibiting components downstream of the cell surface receptors. In another embodiment, inhibition of Wnt secretion may involve inhibiting the activity of any of the proteins implicated in the secretion of functional WNTs.

Furthermore, the invention provides a method for treating a WNT pathway disorder in a subject suffering from the disorder by administering to the subject a therapeutically effective amount of a WNT inhibitor. In one embodiment, the disorder is a cell proliferative disorder associated with aberrant, e.g., increased, activity of WNT signaling. In another embodiment, the disorder results from increased amount of a WNT protein. In yet another embodiment, the cell proliferative disorder is cancer, include but are not limited to: lung (small cell and non-small cell), breast, prostate, carcinoid, bladder, gastric, pancreatic, liver (hepatocellular), hepatoblastoma, colorectal, head cancer and neck squamous cell carcinoma, esophageal, ovarian, cervical, endometrial, mesothelioma, melanoma, sarcoma, osteosarcoma, liposarcoma, thyroid, desmoids, chronic myelocytic leukemia (AML), and chronic myelocytic leukemia (CML). In yet another embodiment, the cell proliferative disorder is fibrosis, include but are not limited to: lung fibrosis, such as idiopathic pulmonary fibrosis and radiation-induced fibrosis, renal fibrosis and liver fibrosis including liver cirrhosis. In yet another embodiment, the disorder is osteoarthritis, Parkinson's disease, retinopathy, macular degeneration.

For therapeutically use, the compound of the present invention could be administered in a therapeutically effective amount via any acceptable way known in the art singly. As used herein, the therapeutically effective amount may vary widely depending on the severity of the disease, the age and relative health of the subject, the potency of the compound used and other factors. Generally, the satisfactory result is indicated to be obtained systemically at a daily dosage of about 0.03 to 2.5 mg/kg per body weight of the subject. In one embodiment, the indicated daily dosage for larger mammal as human is in the range from about 0.5 mg to about 100 mg. Preferably, the compound is administered in divided doses up to four times a day or in retard form. In another embodiment, suitable unit dosage forms for oral administration comprise from ca. 1 to 100 mg active ingredient.

Alternatively, the compound of the present invention may be administered in a therapeutically effective amount as the active ingredient in combination with one or more therapeutic agents, such as pharmaceutical combinations. There may be synergistic effects when the compound of the present invention is used with a chemotherapeutic agent known in the art. The dosage of the co-administered compounds could vary depending on the type of co-drug employed, the specific drug employed, the condition being treated and so forth.

The compound of the present invention or the composition thereof may be administered by any conventional route. In one embodiment, it is administered enterally, such as orally, and in the form of tablets or capsules. In another embodiment, it is administered parenterally and in the form of injectable solutions or suspensions. In yet another embodiment, it is administered topically and in the form of lotions, gels, ointments or creams, or in a nasal or suppository form.

In another aspect, the invention also provides a pharmaceutical combination, preferably, a kit, comprising a) a first agent which is the compound of the present invention as disclosed herein, in free form or in pharmaceutically acceptable salt form, and b) at least one co-agent. In addition, the kit may comprise instructions for its administration.

The combination of the present invention may be used in vitro or in vivo. Preferably, the desired therapeutic benefit of the administration may be achieved by contacting cell, tissue or organism with a single composition or pharmacological formulation that includes the compound of the present invention and one or more agents, or by contacting the cell with two or more distinct compositions or formulations, wherein one composition includes one agent and the other includes another. The agents of the combination may be administered at the same time or separately within a period of time. Preferably, the separate administration can result in a desired therapeutic benefit. The present compound may precede, be co-current with and/or follow the other agents by intervals ranging from minutes to weeks. A person skilled in the art could generally ensure the interval of the time of each delivery, wherein the agents administered separately could still be able to exert an advantageously combined effect on the cell, tissue or organism. In one embodiment, it is contemplated that one may contact the cell, tissue or organism with two, three, four or more modalities substantially simultaneously as the candidate substance, i.e., with less than about one minute. In another embodiment, one or more agents may be administered about between 1 minute to 14 days.

In another aspect, the present provides a process for preparing the compound of the present invention or the salts or derivatives thereof.

In one embodiment, the compound having Formula (I) may be prepared following any one of the synthetic methodologies described in Examples below. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry", John Wiley and Sons, 1991). Suitable leaving groups for use in the synthetic methodologies described include halogen leaving groups and other conventional leaving groups known in the art. Preferably, the leaving group is chloro or bromo.

In another embodiment, the compound of the invention or the salts thereof may also be obtainable in the form of hydrates, or their crystals may include for example the solvent used for crystallization (present as solvates). Salts can usually be converted to compounds in free form by treating with suitable basic agents, preferably with alkali metal carbonates, alkali metal hydrogen carbonates, or alkali metal hydroxides, more preferably with potassium carbonate or sodium hydroxide. A compound of the invention in a base addition salt form may be converted to the corresponding free acid by treating with a suitable acid, such as hydrochloric acid. In view of the close relationship between the novel compounds in free form and those in the form of their salts, including those salts that may be used as intermediates, for example in the purification or identification of the novel compounds, any reference to the free compounds is to be understood as referring also to the corresponding salts, as appropriate.

Salts of the present compound with a salt-forming group may be prepared in a manner known in the art. Acid addition salts of compound of Formula (I) may thus be obtained by treatment with an acid or with a suitable anion exchange reagent. Pharmaceutically acceptable salts of the compound of the invention may be formed as acid addition salts from compound of Formula (I) with a basic nitrogen atom with organic or inorganic acids.

Preferably, suitable inorganic acids include, but are not limited to, halogen acids, such as hydrochloric acid, sulfuric acid, or phosphoric acid.

Preferably, suitable organic acids include, but are not limited to, carboxylic, phosphoric, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, -malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4 aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disuifonic acid, 2-, 3- or 4 methylbenzenesulfonic acid, methylsulfuric acid, ethylsulfuric acid, dodecylsulfuric acid, N cyclohexylsulfamic acid, N-methyl-, N-ethyl- or N-propyl-sulfamic acid, or other organic protonic acids, such as ascorbic acid.

Alternatively, it is also possible to use pharmaceutically unacceptable salts for isolation or purification, for example picrates or perchlorates. But for therapeutic use, only pharmaceutically acceptable salts or free compounds are employed, where applicable in the form of pharmaceutical preparations.

In yet another embodiment, compound of the present invention in unoxidized form may be prepared from N-oxides of compound of the invention by treating with a reducing agent in a suitable inert organic solvent at 0 to 80° C. Preferably, the reducing agent is sulfur, sulfur dioxide, triphenyl phosphine, lithium borohydride, sodium borohydride, phosphorus trichloride, tribromide, or the like. Preferably, the invert organic solvent is acetonitrile, ethanol, aqueous dioxane, or the like.

In yet another embodiment, prodrug derivatives of the compound of the present invention may be prepared by methods known in the art (for further details see Saulnier et al., (1994), Bioorganic and Medicinal Chemistry Letters, Vol. 4, p. 1985). In a preferable embodiment, an appropriate prodrug may be prepared by reacting a non-derivatized compound of the invention with a suitable carbamylating agent such as 1,1-acyloxyalkylcarbanochloridate, para-nitrophenyl carbonate, or the like.

In yet another embodiment, protected derivatives of the compound of the present invention may be made by means known in the art. A detailed description of techniques applicable to the creation of protecting groups and their removal may be found in T. W. Greene, "Protecting Groups in Organic Chemistry", 3rd edition, John Wiley and Sons, Inc., 1999.

In yet another embodiment, compound of the present invention may be prepared as their individual stereoisomers. The process includes reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compound of the present invention, or by using dissociable complexes such as crystalline diastereomeric salts. Diastereomers have distinct physical properties presented by melting points, boiling points, solubilities, reactivity, etc., and may be readily separated by taking advantage of these dissimilarities. The diastereomers may be separated by fractionated crystallization, chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture may be found in Jean Jacques, Andre Collet, Samuel H. Wilen, "Enantiomers, Racemates and Resolutions", John Wiley And Sons, Inc., 1981.

In conclusion, the compound of the present invention could be made by the process described in the Examples; optionally a pharmaceutically acceptable salt may be converted from the compound of the present invention; optionally a pharmaceutically acceptable N-oxide may be converted from an unoxidized form of the compound the present invention; optionally an individual isomer of the compound of the present invention is resolved from a mixture of isomers; and optionally a pharmaceutically acceptable prodrug derivative may be converted from a non-derivatized compound of the present invention.

Insofar as the production of the starting materials is not particularly described, the compounds are known or can be prepared analogously to methods known in the art or as disclosed in the Examples hereinafter. One of skill in the art will appreciate that the above transformations are only representative of methods for preparation of the compounds of the present invention, and that other well-known methods can similarly be used.

IV. Treatment of Cancer

In another aspect, the present invention provides compositions and methods for treatment of cancer characterized by overexpression of R-spondin and/or expression of an R-spondin fusion in a subject that has been diagnosed as having overexpression of R-spondin and/or R-spondin fusion and is in need of such treatment.

R-spondins (RSPOs) are a family of four cysteine-rich secreted proteins containing a single thrombospondin type I repeat (TSR) domain. The Rspo gene family is evolutionary conserved and can be found in the genomic and transcript databases of all deuterostomes including the hemichordate, *Saccoglossus kowalevskii* (acorn worm), the chordate, *Ciona intestinalis* (tunicate), and the echinoderm. RSPOs from different vertebrate species display the properties of the canonical WNT signaling activators. The CR domain of the RSPO proteins is primarily responsible for mediating the activation of the WNT/β-catenin signaling pathway. The TSR and BR domains are proposed to regulate the strength of RSPO activity on canonical WNT signaling, because the RSPO protein lacking the TSR and BR domains activates canonical WNT signaling less effectively. Yoon, J. K. & Lee, J. S. Cellular signaling and biological functions of R-spondins. Cell. Signal. 24, 369-377 (2012).

By "R-spondin fusion" herein is meant a fusion between one of the Rspo genes (including but not limited to Rspo2 and Rspo3 genes) and another gene ("Fusion partner gene"), including, but not limited to PTPRK and EIF3E genes. The fusion may due to deletion or inversion. The fusion of Rspo gene and the fusion partner gene generally leads to expression of Rspo gene (full length or partial as part of the fusion gene product) under the control of a promoter of a different gene (e.g. the fusion partner gene), which leads to change of expression level (e.g., elevated expression) of Rspo gene (e.g., a fusion gene) at the mRNA level and/or protein level. The Rspo fusion gene may produce to a functional or non-functional Rspo fragment.

"Characterized by" with respect to a cancer and mutant R-spondin polynucleotide and polypeptide is meant a cancer in which a gene deletion or translocation and/or expressed fusion polypeptide involving R-spondin are present as compared to a cancer in which such gene deletion and/or fusion polypeptide are not present. The presence of mutant polypeptide may drive, in whole or in part, the growth and survival of such cancer.

The compositions provided herein is used to treat a variety of cancers that involve Rspo fusion, such as colorectal cancer, gastric cancer, liver cancer, and esophageal cancer.

A mechanism for certain tumors, such as colorectal tumors, to gain activation of the WNT pathway is that two genes encoding enhancers of WNT ligands, R spondin-2 and R spondin-3, are transcriptionally activated by fusion to other genes, such as PTPRK and EIF3E genes. See Examples provided herein and Seshagiri S, et al. Recurrent R-spondin fusions in colon cancer. Nature. 2012 Aug. 30; 488(7413):660-4, which is incorporated by reference in its entirety. The Rsop fusion gene may lead to a functional or non-functional Rsop fragment. When a functional Rspo is generated, it may act as an activator of Wnt pathway, which may cause the proliferation of tumor cells.

The present invention provides methods and compositions for screening for cancer patients with Rspo fusions using methods known in the art and/or provided herein, and optionally treating such patients with Wnt inhibitor as provided herein.

The Rspo gene can be detected at genomic DNA level, mRNA level, or protein level. A biological sample from a subject in need of testing is obtained using methods known the art. The biological sample is optionally processed to obtain protein, RNA, and/or DNA, which is in turn used in assays to detect Rspo fusion.

A. Biological Sample

By "biological sample" herein is meant any biological sample suspected of containing Rspo fusion polynucleotides or polypeptides or fragments thereof (including Rspo-PTPRK and Rspo-EIF3E fusion polynucleotides and polypeptides), and may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells, blood, urine, marrow, or a tissue, and the like.

Biological samples useful in the practice of the methods of the invention may be obtained from any mammal in which a cancer characterized by the expression of an Rspo3-PTPRK or Rspo2-EIF3E fusion polypeptide is present or developing. In one embodiment, the mammal is a human, and the human may be a candidate for a Wnt-inhibiting therapeutic for the treatment of a cancer, e.g. colon, gastric and esophageal cancer. The human candidate may be a patient currently being treated with, or considered for treatment with, a Wnt inhibitor, such as those provided herein. In another embodiment, the mammal is large animal, such as a horse or cow, while in other embodiments, the mammal is a small animal, such as a dog or cat, all of which are known to develop cancers, including colon, gastric and esophageal carcinomas.

Any biological sample comprising cells (or extracts of cells) from a mammalian cancer is suitable for use in the methods of the invention. Circulating tumor cells may also be obtained from serum using tumor markers, cytokeratin protein markers or other methods of negative selection as described (see Ma et al., *Anticancer Res.* 23(1A): 49-62 (2003)). Serum and bone marrow samples may be particularly preferred for patients with leukemia. For cancers involving solid tumors, such as sarcomas and carcinomas, the biological sample may comprise cells obtained from a tumor biopsy, which maybe be obtained according to standard clinical techniques.

Circulating tumor cells ("CTCs") may be purified, for example, using the kits and reagents sold under the trademarks Vita-Assays™, Vita-Cap™, and CellSearch® (commercially available from Vitatex, LLC (a Johnson and Johnson corporation). Other methods for isolating CTCs are described (see, for example, PCT Publication No. WO/2002/020825, Cristofanilli et al., New Engl. J. of Med. 351 (8):781-791 (2004), and Adams et al., J. Amer. Chem. Soc. 130(27): 8633-8641 (July 2008)). In a particular embodiment, a circulating tumor cell ("CTC") may be isolated and identified as having originated from the lung, or colon, stomach, esophagus.

B. Detection of Rspo Fusion Polypeptide

In some embodiments, the Rspo fusion is detected by an immunoassay. An Rspo fusion protein or peptide is generated to produce antibodies (monoclonal or polyclonal) specific for Rspo fusion proteins. Such antibodies are then used in an assay to detect the presence of Rspo fusion.

Rspo fusion is generally detecgted using a Rspo fusion-specific reagent. By "Rspo fusion polypeptide-specific reagent" herien is meant any reagent, biological or chemical, capable of specifically binding to, detecting and/or quantifying the presence/level of expressed Rspo fusion polypeptide in a biological sample. The term includes, but is not limited to, the preferred antibody and reagents discussed below, and equivalent reagents are within the scope of the present invention.

Reagents suitable for use in practice of the methods of the invention include an Rspo3-PTPRK fusion polypeptide-specific antibody and or Rspo2-EIF3E fusion polypeptide-specific antibody. A fusion-specific antibody of the invention is an isolated antibody or antibodies that specifically bind(s) an Rspo3-PTPRK fusion polypeptide of the invention (e.g. the peptide corresponding to the Rspo3-PTPRK fusion sequences provided herein) but does not substantially bind either wild type Rspo or wild type PIPRK, or specifically bind(s) a Rspo2-EIF3E fusion polypeptide described herein (e.g. the peptide corresponding to the Rspo2-EIF3E fusion sequences provided herein) but does not substantially bind either wild type Rspo or wild type EIF3E.

Human Rspo3-PTPRK or Rspo2-EIF3E fusion polypeptide-specific antibodies may also bind to highly homologous and equivalent epitopic peptide sequences in other mammalian species, for example murine or rabbit, and vice versa. Antibodies useful in practicing the methods of the invention include (a) monoclonal antibodies, (b) purified polyclonal antibodies that specifically bind to the target polypeptide (e.g. the fusion junction of Rspo3-PTPRK fusion polypeptide or Rspo2-EIF3E fusion polypeptide, (c) antibodies as described in (a)-(b) above that bind equivalent and highly homologous epitopes or phosphorylation sites in other non-human species (e.g. mouse, rat), and (d) fragments of (a)-(c) above that bind to the antigen (or more preferably the epitope) bound by the exemplary antibodies disclosed herein By "antibody" or "antibodies" herein is meant all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. See, e.g., M. Walker et al., Molec. Immunol. 26: 403-11 (1989); Morrision et al., Proc. Nat'l. Acad. Sci. 81: 6851 (1984); Neuberger et al., Nature 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed specific antibodies made according to the method disclosed in U.S. Pat. No. 4,676,980 (Segel et al.)

The invention is not limited to use of antibodies, but includes equivalent molecules, such as protein binding domains or nucleic acid aptamers, which bind, in a fusion-protein or truncated-protein specific manner, to essentially the same epitope to which an Rspo3-PTPRK or Rspo2-EIF3E fusion polypeptide-specific antibody useful in the methods of the invention binds. See, e.g., Neuberger et al., Nature 312: 604 (1984). Such equivalent non-antibody reagents may be suitably employed in the methods of the invention further described below.

Polyclonal antibodies useful in practicing the methods of the invention may be produced according to standard techniques by immunizing a suitable animal (e.g., rabbit, goat, etc.) with an antigen encompassing a desired fusion-protein specific epitope (e.g. the fusion junction of an Rspo fusion protein described herein), collecting immune serum from the animal, and separating the polyclonal antibodies from the immune serum, and purifying polyclonal antibodies having the desired specificity, in accordance with known procedures. The antigen may be a synthetic peptide antigen comprising the desired epitopic sequence, selected and constructed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, Methods In Enzymology, 201: 264-283 (1991); Merrifield, J. Am. Chem. Soc. 85: 21-49 (1962)). Polyclonal antibodies produced as described herein may be screened and isolated as further described below.

Monoclonal antibodies may also be beneficially employed in the methods of the invention, and may be produced in hybridoma cell lines according to the well-known technique of Kohler and Milstein. Nature 265: 495-97 (1975); Kohler and Milstein, Eur. J. Immunol. 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of assay methods provided by the invention. For example, a solution containing the appropriate antigen (e.g. a synthetic peptide comprising the fusion junction of Rspo3-PTPRK or Rspo2-EIF3E fusion polypeptide) may be injected into a mouse and, after a sufficient time (in keeping with conventional techniques), the mouse sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063, K. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.*, 82: 8653 (1985); Spira et al., *J. Immunol. Methods*, 74: 307 (1984)). The antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Further still, U.S. Pat. No. 5,194,392, Geysen (1990) describes a general method of detecting or determining the sequence of monomers (amino acids or other compounds) that is a topological equivalent of the epitope (i.e., a "mimotope") that is complementary to a particular paratope (antigen binding site) of an antibody of interest. More generally, this method involves detecting or determining a sequence of monomers that is a topographical equivalent of a ligand that is complementary to the ligand binding site of a particular receptor of interest. Similarly, U.S. Pat. No. 5,480,971, Houghten et al. (1996) discloses linear $C_1$-C-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Antibodies useful in the methods of the invention, whether polyclonal or monoclonal, may be screened for epitope and fusion protein specificity according to standard techniques. See, e.g. Czernik et al., *Methods in Enzymology*, 201: 264-283 (1991). For example, the antibodies may be screened against a peptide library by ELISA to ensure specificity for both the desired antigen and, if desired, for reactivity only with, e.g. an Rspo3-PTPRK fusion polypeptide of the invention and not with wild-type Rspo3 or wild-type PTPRK. The antibodies may also be tested by Western blotting against cell preparations containing target protein to confirm reactivity with the only the desired target and to ensure no appreciable binding to other fusion proteins involving Rspo. The production, screening, and use of fusion protein-specific antibodies is known to those of skill in the art, and has been described. See, e.g., U.S. Patent Publication No. 20050214301, Wetzel et al., Sep. 29, 2005.

Fusion polypeptide-specific antibodies useful in the methods of the invention may exhibit some limited cross-reactivity with similar fusion epitopes in other fusion proteins or with the epitopes in wild type Rspo, wild type PTPRK, and wild type EIF3E that form the fusion junction. This is not unexpected as most antibodies exhibit some degree of cross-reactivity, and anti-peptide antibodies will often cross-react with epitopes having high homology or identity to the immunizing peptide. See, e.g., Czernik, supra. Cross-reactivity with other fusion proteins is readily characterized by Western blotting alongside markers of known molecular weight. Amino acid sequences of cross-reacting proteins may be examined to identify sites highly homologous or identical to the Rspo3-PTPRK or Rspo2-EIF3E fusion polypeptide sequence to which the antibody binds. Undesirable cross-reactivity can be removed by negative selection using antibody purification on peptide columns (e.g. selecting out antibodies that bind either wild type Rspo, wild type PTPRK, and/o wild type EIF3E).

Rspo3-PTPRK or Rspo2-EIF3E fusion polypeptide specific antibodies of the invention that are useful in practicing the methods disclosed herein are ideally specific for human fusion polypeptide, but are not limited only to binding the human species, per se. The invention includes the production and use of antibodies that also bind conserved and highly homologous or identical epitopes in other mammalian species (e.g. mouse, rat, monkey). Highly homologous or identical sequences in other species can readily be identified by standard sequence comparisons, such as using BLAST, with a human Rspo3-PTPRK or Rspo2-EIF3E fusion polypeptide.

Antibodies employed in the methods of the invention may be further characterized by, and validated for, use in a particular assay format, for example flow cytometry (FC), immunohistochemistry (IHC), and/or Immunocytochemistry (ICC). Antibodies may also be advantageously conjugated to fluorescent dyes (e.g. Alexa488, PE), or labels such as quantum dots, for use in multi-parametric analyses along with other signal transduction (phospho-AKT, phospho-Erk 1/2) and/or cell marker (cytokeratin) antibodies.

C. Detection of Rspo Fusion Polynucleotide

Fusion-specific reagents provided by the invention also include nucleic acid probes and primers suitable for detection of an Rspo3-PTPRK or Rspo2-EIF3E fusion polynucleotide. Such probes desirable include, among others, breakpoint probes corresponding to both sides of the breakpoints in wild-type Rspo and/or wildetype PTPRK genes, or wild-type Rspo and/or wild-type EIF3E genes, that produce the fusion. Specific use of such probes in assays such as fluorescence in-situ hybridization (FISH) or polymerase chain reaction (PCR) amplification is described herein.

In some embodiments, the Rspo fusion is detected by PCR, such as regular PCR, Real-time PCR (Q-PCR) or digital PCR. A pair of primers is used to amplify the fusion genes. The primers are designed based on the fusion gene sequence to be amplified. Preferably, one primer hybridizes to a first sequence of an Rspo gene and the second primer hybridizes to a second sequence of a fusion partner gene. PCR can be performed on either cDNA (as prepared from RNA using the biological sample) or genomic DNA, under conditions that can be optimized as known in the art.

In some embodiments, FISH is employed (as described in Verma et al. HUMAN CHROMOSOMES: A MANUAL OF BASIC TECHNIQUES, *Pergamon Press*, New York, N.Y. (1988)) and may be correlated with other physical chromosome mapping techniques and genetic map data. Examples of genetic map data can be found in the 1994 Genome Issue of *Science* (265: 1981f). Correlation between the location of the gene encoding Rspo3-PTPRK or Rspo2-EIF3E fusion polypeptide on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In some embodiments, a first probe hybridizes to an Rspo gene sequence and is labeled with a first color (e.g., red) and a second probe hybridizes to a fusion partner gene sequence and is labeled with a second color (e.g., green). In the case of Rspo fusion, the two probes hybridize to the fusion gene and become adjacent to each other. As a result, the images of the two probes will merger, which results in a different color (e.g., yellow).

It shall be understood that all of the methods (e.g., PCR and FISH) that detect Rspo3-PTPRK or Rspo2-EIF3E fusion polynucleotides of the invention may be combined with other methods that detect either mutant Rspo polynucleotides or mutant Rspo polypeptides. For example, detection of a Rspo3-PTPRK or Rspo2-EIF3E fusion polynucleotide in the genetic material of a biological sample (e.g., in a circulating tumor cell) may be followed by Western blotting analysis or immuno-histochemistry (IHC) analysis of the proteins of the sample to determine if the Rspo3-PTPRK or Rspo2-EIF3E fusion polynucleotide was actually expressed as a Rspo3-PTPRK or Rspo2-EIF3E fusion polypeptide in the biological sample. Such Western blotting or IHC analyses may be performed using an antibody that specifically binds to the polypeptide encoded by the detected Rspo3-PTPRK or Rspo2-EIF3E fusion polynucleotide, or the analyses may be performed using antibodies that specifically bind either to full length Rspo (e.g., bind to the N-terminus of the protein) or to full length PTPRK (e.g., bind an epitope in the kinase domain of PTPRK). Such assays are known in the art (see, e.g., U.S. Pat. No. 7,468,252).

In another example, the CISH technology of Dako allows chromatogenic in-situ hybridization with immuno-histochemistry on the same tissue section.

In some embodiments, the Rspo fusion is detected by hybridization in a Southern blot assay using a probe that comprise sequences from both the Rspo gene and the fusion partner gene.

In some embodiments, the Rspo fusion is detected by other hybridization-based methods, such as microarray, branched DNA (QuantiGene®), ViewRNA® or RNAscope®.

In some embodiments, the Rspo fusion is detected by hybridization using microarray where a custom fusion gene microarray is used to detect Rspo fusion transcripts from cancer specimens. The oligos are designed to enable combined measurements of chimeric transcript junctions with exon-wise measurements of individual fusion partners. See Skotheim, R I; Thomassen, G O; Eken, M; Lind, G E; Micci, F; Ribeiro, F R; Cerveira, N; Teixeira, M R et al. A universal assay for detection of oncogenic fusion transcripts by oligo microarray analysis. *Molecular Cancer* 8: 5. (2009).

In some embodiments, the Rspo fusion is detected by hybridization using branched DNA assay. In these embodiments a custom hybridization and signal amplification assay, such as the branched DNA assay (QuantiGene®), is used to detect Rspo fusion transcripts in lysis solutions from cancer specimens. The sequences of capture extender probes and the label extender probes are derived from the exon sequences of Rspo genes and fusion partner genes (e.g., PTPRK for Rspo3, EIF3E for Rspo2) such as those exemplified in Example 9. See, Lu B., et al. Detection of TMPRSS2-ERG fusion gene expression in prostate cancer specimens by a novel assay using branched DNA. *Urology* 74(5):1156-61 (2009).

In some embodiments, Rspo fusion is detected by in situ hybridization. A custom in situ hybridization and signal amplification assay, such as the RNAview® or RNAscope®, is used to detect Rspo fusion transcripts on formalin fixed paraffin embedded (FFPE) or frozen tissues from cancer specimens. The sequences of capture extender probes and the label extender probes are derived from the exon sequences of Rspo genes and fusion partner genes (e.g., PTPRK for Rspo3, EIF3E for Rspo2) such as those exemplified in Example 9. See, Wang F, Flanagan J, Su N, Wang L C, Bui S, Nielson A, Wu X, Vo H T, Ma X J, Luo Y. RNAscope: a novel in situ RNA analysis platform for formalin-fixed, paraffin-embedded tissues. *J Mol Diagn.* 14(1):22-9 (2012)

In some embodiments, the Rspo fusion is detected by sequencing, such as Sanger sequencing or Next-generation sequencing.

Sequencing by extending a sequencing primer or by extending an extension product can be carried out using a variety of methods. For example, sequencing can be carried out with a labeled reversible terminator or by ligation with a labeled oligonucleotide. Sequencing can be performed using any commercially available method, such as a reversible terminator based sequencing method that is commercially available from companies such as Illumina, Inc. (San Diego, Calif.), and Life Technologies (Ion Torrent).

In some embodiments, high-throughput sequencing involves the use of technology available from Roche/454 Lifesciences, Inc. (Branford, Conn.). Methods for using bead amplification followed by fiber optics detection are described in Marguiles, M., et al. "Genome sequencing in microfabricated high-density picolitre reactors", Nature, doi: 10.1038/nature03959; and well as in US Publication Application Nos. 20020012930, 20030058629, 20030100102, 20030148344, 20040248161, 20050079510, 20050124022 and 20060078909.

In some embodiments, high-throughput sequencing is performed using Clonal Single Molecule Array (Solexa, Inc/Illumina, Inc.) or sequencing-by-synthesis (SBS) utilizing reversible terminator chemistry. These technologies are described in part in, e.g., U.S. Pat. Nos. 6,969,488; 6,897,023; 6,833,246; 6,787,308; and US Publication Application Nos. 20040106130, 20030064398, 20030022207, and Constans, A., The Scientist 2003, 17(13):36.

In some embodiments, the method provided herein detects an R-spondin fusion comprising a gene fusion between PTPRK and Rspo3 genes. The R-spondin fusion generally results in expression of R-spondin gene driven by promoter of the PTPRK gene.

In some embodiments, the method detects an R-spondin fusion comprising a gene fusion between PTPRK exon 1 and Rspo3 exon 2, or between PTPRK exon7 and Rspo3 exon 2.

In some embodiments, the method detects an R-spondin fusion comprising a gene fusion between EIF3E and Rspo3 genes. Preferably, the R-spondin fusion results in expression of R-spondin gene driven by promoter of the EIF3E gene.

In some embodiments, the method detects an R-spondin fusion comprising a gene fusion between EIF3E exon 1 and Rspo2 exon 2 or between EIF3E exon 1 and Rspo2 exon 3.

D. Detection of R-Spondin Overexpression

In another aspect, the present invention provide compositions and methods for detection of R-spondin overexpression. Overexpression of R-spondi may or may not co-exist with overexpression or activation of Wnt.

R-spondin overexpression can be overexpression of either R-spondin mRNA or polypeptide, or both. The R-spondin can be either wild-type or a variant of R-spondin, such as R-spondin fusion as disclosed herein (e.g., Rspo3-PTPRK or Rspo2-EIF3E fusion).

R-spondin overexpression is determined relevant to a baseline expression level, which is obtained by measuring expression level of R-spodin (mRNA or polypeptide) in normal cells or a normal subject population (e.g., normal human population).

The expression level of R-spodin mRNA level is measured using methods known in the art, such as Northern blot, RT-PCR, RT-PCT combined with Real-time PCR, digital PCR, DNA array, high throughput sequencing, or in situ hybridization, and the like.

The expression level of R-spodin, either at mRNA level or protein level, is measured using methods known in the art, such as Western blot, protein array, immunohistology staining, and the like.

E. Screening and Treatment of Subject with Rspo Overexpression and/or Rspo Fusion Gene In another aspect, the present invention provides a method for determining whether a subject with cancer should be treated with a composition that inhibits Wnt activity, the method comprising: (a) isolating a biological sample from the subject; (b) performing an assay on the biological sample to determine expression of Rspo mRNA or polypeptide and/or identify the presence or absence of an R-spondin fusion; and (c) determining that the subject should be treated with a composition that inhibits Wnt activity if the biological sample contains Rspo mRNA or polypeptide overexpression and/or an R-spondin fusion, wherein the composition comprises a compound of the following formula:

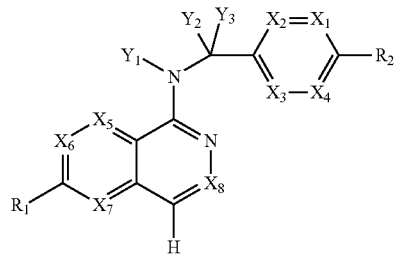

or a physiologically acceptable salt thereof, wherein
$X_1$, $X_2$, $X_3$, $X_4$, $X_5$, $X_6$, $X_7$, $X_8$ are independently $CR_4$ or N;
$Y_1$ is hydrogen or $CR_4$; $Y_2$, $Y_3$ are independently hydrogen, halo or $CR_3$;
$R_1$ is morpholinyl, piperazinyl, quinolinyl,

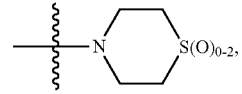

aryl, $C_{1-6}$ heterocycle, 5 or 6 membered heteroaryl containing 1-2 heteroatoms selected from N, O and S;
$R_2$ is hydrogen, halo, morpholinyl, piperazinyl, quinolinyl,

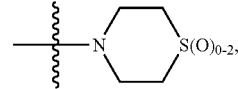

aryl, $C_{1-6}$ heterocycle, 5 or 6 membered heteroaryl containing 1-2 heteroatoms selected from N, O and S;
$R_3$ is hydrogen, halo, cyano, $C_{1-6}$ alkyl, $C_{1-6}$ alkoxy optionally substituted with halo, amino, hydroxyl, alkoxy or cyano;
$R_4$ is hydrogen, halo, $C_{1-6}$alkoxy, —$S(O)_2R_5$, —$C(O)OR_5$, —$C(O)R_5$, —$C(O)NR_6R_7$, $C_{1-6}$ alkyl, $C_{2-6}$ alkenyl or $C_{2-6}$ alkynyl, each of which can be optionally substituted with halo, amino, hydroxyl, alkoxy or cyano;
$R_5$, $R_6$ and $R_7$ are independently hydrogen, $C_{1-6}$ alkyl, $C_{2-6}$ alkenyl or $C_{2-6}$ alkynyl, each of which may be optionally substituted with halo, amino, hydroxyl, alkoxy or cyano.

In some embodiments, the method further comprises treating the subject with the a composition provided herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES

Akiri G, Cherian M M, Vijayakumar S, Liu G, Bafico A, Aaronson S A. Wnt pathway aberrations including autocrine Wnt activation occur at high frequency in human non-small-cell lung carcinoma. Oncogene. 2009 May 28; 28(21):2163-72.

Bafico A, Liu G, Goldin L, Harris V, Aaronson S A. An autocrine mechanism for constitutive Wnt pathway activation in human cancer cells. Cancer Cell. 2004 November; 6(5):497-506.

Barker N, Clevers H. Mining the Wnt pathway for cancer therapeutics. Nat Rev Drug Discov. 2006 December; 5(12):997-1014.

Blom A B, van Lent P L, van der Kraan P M, van den Berg W B. To seek shelter from the WNT in osteoarthritis? WNT-signaling as a target for osteoarthritis therapy. Curr Drug Targets. 2010 May; 11(5):620-9.

Boonen R A, van Tijn P, Zivkovic D. Wnt signaling in Alzheimer's disease: up or down, that is the question. Ageing Res Rev. 2009 April; 8(2):71-82.

Camilli T C, Weeraratna A T. Striking the target in Wnt-y conditions: intervening in Wnt signaling during cancer progression. Biochem Pharmacol. 2010 Sep. 1; 80(5): 702-11.

Chan S L, Cui Y, van Hasselt A, Li H, Srivastava G, Jin H, Ng K M, Wang Y, Lee K Y, Tsao G S, Zhong S, Robertson K D, Rha S Y, Chan A T, Tao Q. The tumor suppressor Wnt inhibitory factor 1 is frequently methylated in nasopharyngeal and esophageal carcinomas. Lab Invest. 2007 July; 87(7):644-50.

Chen B, Dodge M E, Tang W, Lu J, Ma Z, Fan C W, Wei S, Hao W, Kilgore J, Williams N S, Roth M G, Amatruda J F, Chen C, Lum L. Small molecule-mediated disruption of Wnt-dependent signaling in tissue regeneration and cancer. Nat Chem Biol. 2009 February; 5(2):100-7.

Cheng J H, She H, Han Y P, Wang J, Xiong S, Asahina K, Tsukamoto H. Wnt antagonism inhibits hepatic stellate cell activation and liver fibrosis. Am J Physiol Gastrointest Liver Physiol. 2008; 294(1):G39-49.

Chun J S, Oh H, Yang S, Park M. Wnt signaling in cartilage development and degeneration. BMB Rep. 2008 Jul. 31; 41(7):485-94.

Chien A J, Moon R T. WNTS and WNT receptors as therapeutic tools and targets in human disease processes. Front Biosci. 2007 Jan. 1; 12:448-57.

DeAlmeida V I, Miao L, Ernst J A, Koeppen H, Polakis P, Rubinfeld B. The soluble wnt receptor Frizzled-8CRD-hFc inhibits the growth of teratocarcinomas in vivo. *Cancer Res.* 2007 Jun. 1; 67(11):5371-9

D'Amour K A, Bang A G, Eliazer S, Kelly O G, Agulnick A D, Smart N G, Moorman M A, Kroon E, Carpenter M K, Baetge E E. Production of pancreatic hormone-expressing endocrine cells from human embryonic stem cells. Nat Biotechnol. 2006 November; 24(11):1392-401.

Herbst A, Kolligs F T. Wnt signaling as a therapeutic target for cancer. Method *Mol Biol.* 2007; 361:63-91.

Hoeppner L H, Secreto F J, Westendorf J J. Wnt signaling as a therapeutic target for bone diseases. Expert Opin Ther Targets. 2009 April; 13(4):485-96.

Hwang I, Seo E Y, Ha H. Wnt/beta-catenin signaling: a novel target for therapeutic intervention of fibrotic kidney disease. Arch Pharm Res. 2009 December; 32(12):1653-62.

Inestrosa N C, Arenas E. Emerging roles of Wnts in the adult nervous system. Nat Rev Neurosci. 2010 February; 11(2): 77-86.

Lie D C, Colamarino S A, Song H J, Desire L, Mira H, Consiglio A, Lein E S, Jessberger S, Lansford H, Dearie A R, Gage F H. WNT signalling regulates adult hippocampal neurogenesis. Nature 437 (7063): 1370-5, 2005.

Kansara M, et al. Wnt inhibitory factor 1 is epigenetically silenced in human osteosarcoma, and targeted disruption accelerates osteosarcomagenesis in mice. J Clin Invest. 2009 April; 119(4):837-51

MacDonald B T, Tamai K, He X. Wnt/beta-catenin signaling: components, mechanisms, and diseases. Dev Cell. 2009 July; 17(1):9-26.

Mikels A J, Nusse R. Wnts as ligands: processing, secretion and reception. Oncogene. 2006 Dec. 4; 25(57):7461-8.

Moon R T. Wnt/beta-catenin pathway. Sci STKE.; 2005 (271):cml.

Morrisey E E. Wnt signaling and pulmonary fibrosis. Am J Pathol. 2003 May; 162(5):1393-7.

Nusse R. WNT signaling and stem cell control". Cell Res. 18 (5): 523-7, 2008 Ouchi N, Higuchi A, Ohashi K, Oshima Y, Gokce N, Shibata R, Akasaki Y, Shimono A, Walsh K. Sfrp5 is an anti-inflammatory adipokine that modulates metabolic dysfunction in obesity. Science. 2010 Jul. 23; 329(5990):454-7.

Reya T, Clevers H. Wnt signalling in stem cells and cancer. Nature. 2005 Apr. 14; 434(7035):843-50.

Rhee C S, Sen M, Lu D, Wu C, Leoni L, Rubin J, Corr M, Carson D A. Wnt and frizzled receptors as potential targets for immunotherapy in head and neck squamous cell carcinomas. Oncogene. 2002 Sep. 26; 21(43):6598-605.

Sullivan G J, et al. Generation of functional human hepatic endoderm from human induced pluripotent stem cells. Hepatology. 2010 January; 51(1):329-35.

Takahashi-Yanaga F, Kahn M. Targeting Wnt signaling: can we safely eradicate cancer stem cells? Clin Cancer Res. 2010 Jun. 15; 16(12):3153-62.

Ten Berge, D. et al. WNT signaling mediates self-organization and axis formation in embryoid bodies. Cell Stem Cell 3, 508-518, 2008.

Yang L, Soonpaa M H, Adler E D, Roepke T K, Kattman S J, Kennedy M, Henckaerts E, Bonham K, Abbott G W, Linden R M, Field L J, Keller G M. Human cardiovascular progenitor cells develop from a KDR+ embryonic-stem-cell-derived population. Nature. 2008 May 22; 453 (7194):524-8.

EXAMPLES

The present invention is further exemplified, but not limited, by the following and Examples that illustrate the preparation of the compounds of the invention.

| Abbreviation | Definition or Explanation |
| --- | --- |
| DCM | Dichloromethane |
| DIEA | N,N'-Diisopropylethylamine |
| DMF | N,N-Dimethylformamide |
| eq. | equivalents |
| TEA | Triethylamine |
| THF | Tetrahydrofuran |
| RT | Room Temperature |
| EA | Ethyl acetate |
| $Pd_2(dba)_3$ | Tris(dibenzylideneacetone)dipalladium(0) |
| s-Phos | 2-Dicyclohexylphosphino-2',6'-dimethoxybiphenyl |
| $Pd(PPh_3)_4$ | Tetrakis(triphenylphosphine)palladium |

Example 1

Synthesis of N-(4-(2-methylpyridin-4-yl)benzyl)-6-(2-methylpyridin-4-yl)-2,7-naphthyridin-1-amine (Compound No. 1)

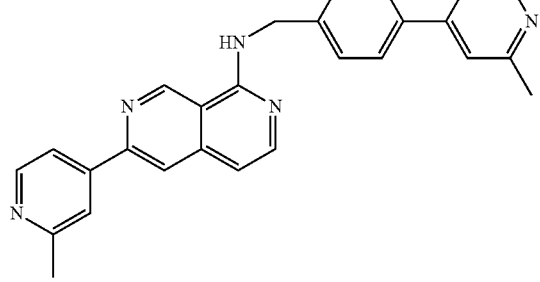

Step 1:

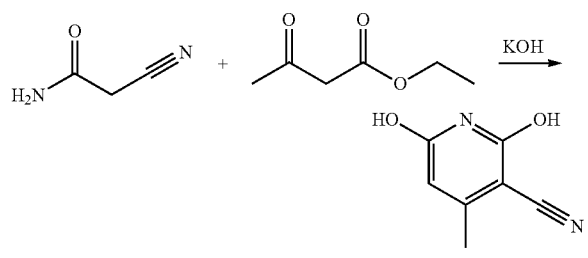

2-Cyanoacetamide (50 g, 601.8 mmol) and ethyl acetoacetate (75 mL, 601.8 mmol) were dissolved in MeOH. KOH (37.0 g, 1.1 eq) was dissolved in MeOH, and added dropwise into the mixture, some white solid came out. The mixture was heated up to reflux at oil bath for 8 h, and then cooled down to RT. The solid was filtered and then re-dissolved into hot water, and then filtered again. 6N HCl was added into the filtration to neutralize till pH<7. The white solid was out again and filtered. The solid was further washed with MeOH, water and MeOH, and then dried by vacuum to get the final product 3-ethynyl-4-methylpyridine-2,6-diol (yield ~41%).

Step 2:

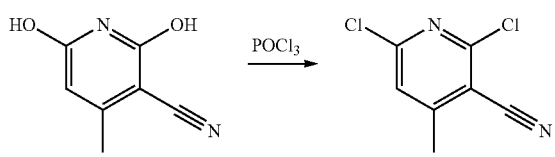

3-ethynyl-4-methylpyridine-2,6-diol (28.0 g, 195.2 mmol) was dissolved in POCl₃ (60.0 mL). The reaction mixture was sealed in a pressure tube and heated up to 180° C. for 6 h. After the reaction was cooled down to room temperature, the excessive POCl₃ was removed under the vacuum. Slowly added crushed ice into the mixture, and the solid came out. Filtered the solid out and dried under the vacuum to get the final product 2,6-dichloro-4-methylpyridine-3-carbonitrile (yield ~92%) without further purity.

Step 3:

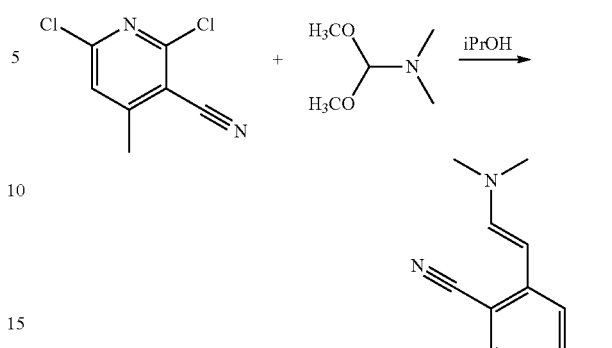

2,6-dichloro-4-methylpyridine-3-carbonitrile (20.0 g, 107.5 mmol) in 200 mL of isopropyl alcohol was added N,N-dimethylformamide dimethlacetal (12.82 g, 107.5 mmol) and the reaction was stirred at 65° C. for 18 h. After cooling down the reaction to RT, the precipitate was collected by filtration and washed with 50 mL of isopropyl alcohol, and air dried to give the product 2,6-dichloro-4-((E)-2-(dimethylamino)vinyl)pyridine-3-carbonitrile (yield 26%) without further purification.

Step 4:

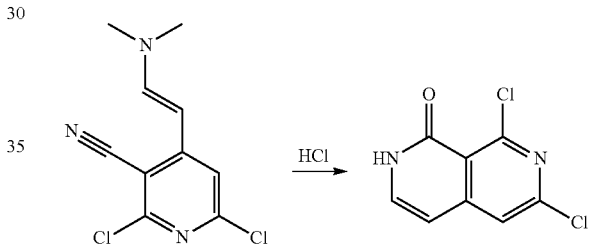

2,6-dichloro-4-((E)-2-(dimethylamino)vinyl)pyridine-3-carbonitrile (4.0 g, 16.6 mmol) was added with 20 mL concentrated HCl in a sealed tube. The reaction is stirred at 45° C. for 18 h. After cooling down the reaction to RT, ice water was added to the solution resulting heavy yellow slurry. The precipitate was collected by filtration, washed with cold water, ether and ethyl acetate, and dried under vacuum to get light yellow solid 6,8-dichloro-2,7-naphthyridin-1(2H)-one (yield ~80%). MS m/z 215.0 (M+1). ¹HNMR (300 MHz, DMSO-d6): δ11.75 (s, 1H), 7.76 (s, 1H), 7.50 (t, J=6.6 Hz, 1H), 6.52 (d, J=6.6 Hz, 1H).

Step 5:

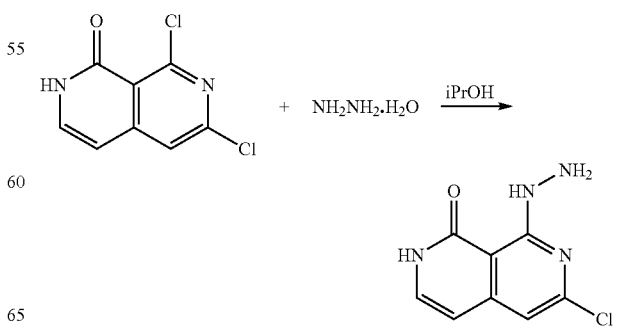

6,8-dichloro-2,7-naphthyridin-1(2H)-one (3.0 g, 13.96 mmol) was dissolved in iPrOH (120 mL) to form a kind of suspension. The solution was cooled down to 0° C. in ice bath, and then hydrazine solution (5.6 g, 80%, 10 eq) was added dropwise. The mixture was stirred at RT for 15 minutes, and then heated in oil bath at 55° C. for overnight. After the reaction mixture was cooled down to RT, filtered to get the solid directly, and then the solid was washed with 70 mL MeOH and dried by vacuum. The product 6-chloro-8-hydrazinyl-2,7-naphthyridin-1(2H)-one (yield ~98%) was used in the next step reaction directly without further purification.

Step 6:

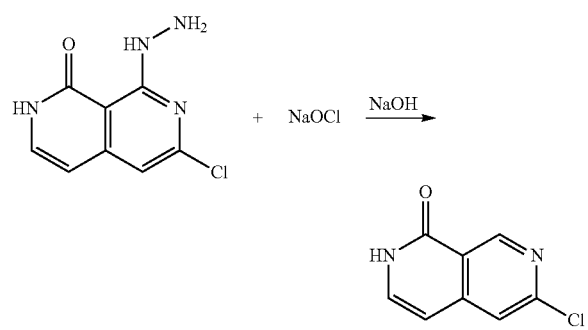

6-chloro-8-hydrazinyl-2,7-naphthyridin-1(2H)-one (1.50 g, 7.12 mmol) was dissolved into MeCN (90 mL) to form a kind of suspension. 1N NaOH (17.80 mL, 2.5 eq) was added, and then equal amount of water (107.80 mL) was added into the mixture. The reaction mixture was heated at 50° C., stirred till becoming the clear solution. The solution was cooled down to 0° C. again, and NaOCl (11.05 g, 12% solution, 2.5 eq) was added dropwise, and then reaction was stirred at RT for overnight. After the reaction was done, the solution was cooled down to 0° C. and then added into 1N HCl to neutralize (pH ~6). Precipitate was collected and the filtrate was extracted with 100 mL×2 EA. The organic layer was combined and dried over Na$_2$SO$_4$ and evaporated to give additional crude product. The combined solid material 6-chloro-2,7-naphthyridin-1(2H)-one (yield ~93%) was used in the next reaction without further purification. MS m/z 181.1 (M+1).

Step 7:

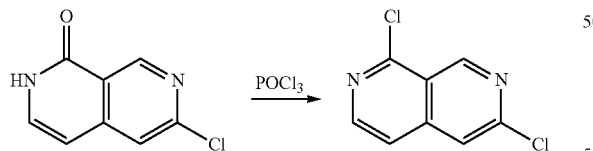

6-chloro-2,7-naphthyridin-1(2H)-one (400 mg, 2.2 mmol) was added in POCl$_3$ (20.0 mL) in a pressure tube. The reaction mixture was heated up to 160° C. for 4 h to get a clear solution. The solution was cooled down to room temperature and poured in DCM, and added crushed ice slowly. Saturated NaHCO$_3$ was added into the mixture to neutralize HCl generated in the reaction. Vacuum to remove DCM and the left water solution was extracted by 100 mL×2 EA. The combined organic layers were washed with brine once, and dried by Na$_2$SO$_4$, and then evaporated under the vacuum to get the solid 1,6-dichloro-2,7-naphthyridine (yield ~73%) to use in the next step reaction without further purifications. MS m/z 199.0 (M+1).

Step 8:

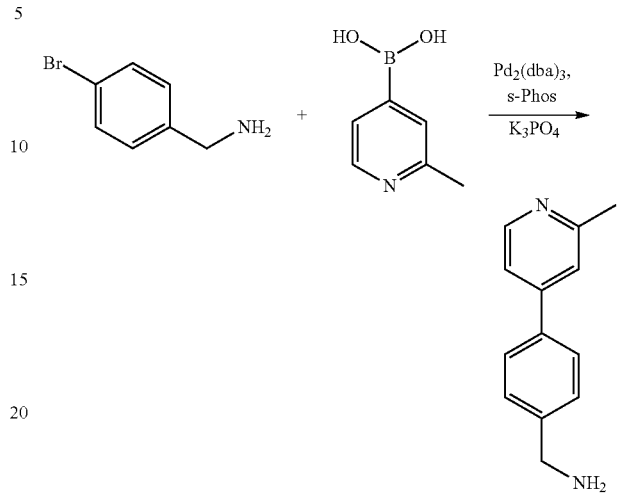

(4-bromophenyl)methanamine (1.00 g, 5.37 mmol) and 2-methylpyridin-4-yl-4-boronic acid (883.30 mg, 6.45 mmol) were dissolved in BuOH (10.0 mL) and water (2.0 mL). K$_3$PO$_4$ (2.28 g, 10.75 mmol), Pd$_2$(dba)$_3$ (120.20 mg, 0.27 mmol) and S-phos (220.70 mg, 0.54 mmol) were added in under N$_2$. The reaction mixture was sealed in a pressure tube and heated up to 125° C. for 1 h. After cooling down the reaction to RT, the mixture was poured into the water and extracted by 100 mL×3 EA. The combined organic layer was washed with brine, dried over Na$_2$SO$_4$, and concentrated under the vacuum to give the crude product. The solid was purified by silicone gel column with 10% MeOH (containing ~2N NH$_3$) in DCM to get the pure (4-(2-methylpyridin-4-yl)phenyl)methanamine (yield ~89%). MS m/z 199.1 (M+1).

Step 9:

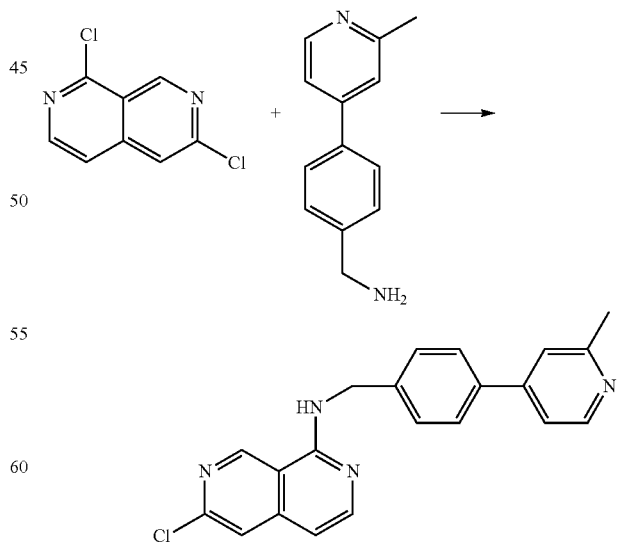

1,6-dichloro-2,7-naphthyridine (160 mg, 0.80 mmol) and (4-(2-methylpyridin-4-yl)phenyl)methanamine (239.10 mg, 1.21 mmol) were dissolved in BuOH (5.0 mL) and heated up to 115° C. for overnight. After the reaction was cooled down to RT, the organic solvent was removed under the vacuum. The crude product was purified by silicone gel flash chromatography with EA/Hexane (1:1) to get the solid N-(4-(2-methylpyridin-4-yl)benzyl)-6-chloro-2,7-naphthyridin-1-amine (yield ~90%). MS m/z 361.1 (M+1).

Step 10:

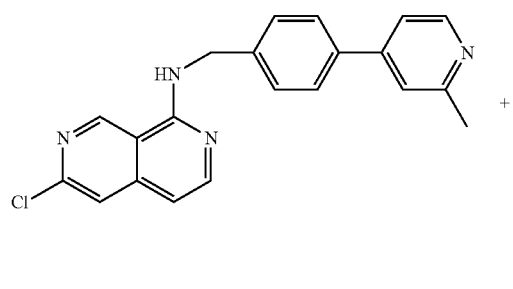

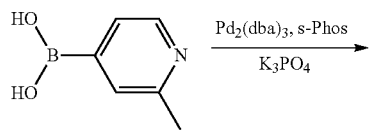

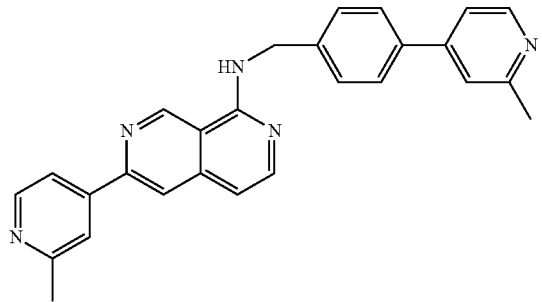 [SMILES: Cc1cc(-c2ccc(CNc3nccc4cc(-c5ccnc(C)c5)ncc34)cc2)ccn1]

N-(4-(2-methylpyridin-4-yl)benzyl)-6-chloro-2,7-naphthyridin-1-amine (50.00 mg, 0.14 mmol) and 2-methylpyridin-4-yl-4-boronic acid (56.90 mg, 0.42 mmol) were dissolved in BuOH (3.0 mL) and water (0.6 mL). $K_3PO_4$ (88.20 mg, 0.028 mmol), $Pd_2(dba)_3$ (6.20 mg, 0.014 mmol) and S-phos (11.40 mg, 0.011 mmol) were added into the mixture under $N_2$. The reaction was sealed in a pressure tube and heated up to 105° C. for overnight. After cooling down the reaction to RT, the mixture was poured in water and extracted by EA for three times. The combined organic layer was washed with brine, dried by $Na_2SO_4$, and concentrated under the vacuum.

The crude product was further purified by prep-TLC with 5% MeOH in DCM to get the final product N-(4-(2-methylpyridin-4-yl)benzyl)-6-(2-methylpyridin-4-yl)-2,7-naphthyridin-1-amine (yield ~70%). MS m/z 418.2 (M+1). $^1$HNMR (300 MHz, $CDCl_3$): 52.46 (s, 3H), 2.63 (s, 3H), 4.94 (d, J=5.10 Hz, 2H), 5.94 (br, 1H), 6.97 (d, J=5.70 Hz, 1H), 7.31 (d, J=4.20 Hz, 1H), 7.36 (s, 1H), 7.54 (d, J=8.10 Hz, 2H), 7.63 (d, J=8.40 Hz, 2H), 7.90 (s, 1H), 8.19 (d, J=6.00 Hz, 1H), 8.22 (s, 1H), 8.51 (m, 2H), 9.08 (s, 1H), 9.30 (s, 1H).

Example 2

Synthesis of N-(3-methyl-4-(2-methylpyridin-4-yl)benzyl)-6-(2-methylpyridin-4-yl)-2,7-naphthyridin-1-amine (Compound No. 2)

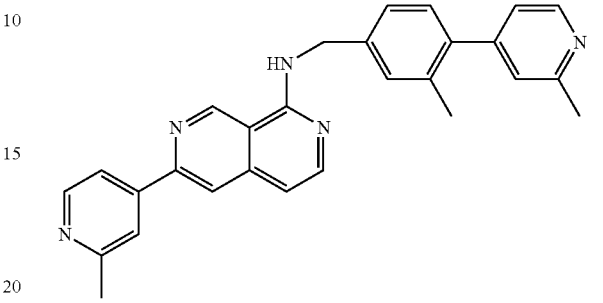

Step 1:

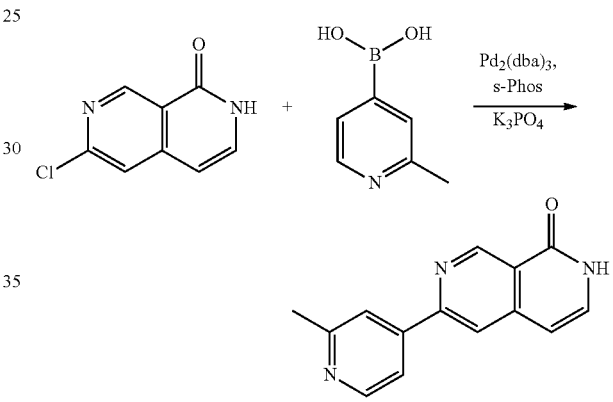

6-chloro-2,7-naphthyridin-1(2H)-one (200 mg, 1.10 mmol) and 2-methylpyridin-4-yl-4-boronic acid (227.60 mg, 1.66 mmol) were dissolved in BuOH (5.0 mL) and water (1.0 mL). $K_3PO_4$ (705.20 g, 3.32 mmol), $Pd_2(dba)_3$ (49.60 mg, 0.22 mmol) and S-phos (91.00 mg, 0.11 mmol) were added under $N_2$. The reaction mixture in the pressure tube was heated up to 130° C. for 1 h. After cooling down the reaction to RT, poured the mixture into the water, extracted by EA for three times. The combined organic layer was washed with brine, dried over $Na_2SO_4$, concentrated under the vacuum to get the crude. The crude product was purified by column with 5% MeOH in DCM to get the final compound 6-(2-methylpyridin-4-yl)-2,7-naphthyridin-1 (2H)-one (yield 61%). MS m/z 238.1 [M+1]+.

Step 2:

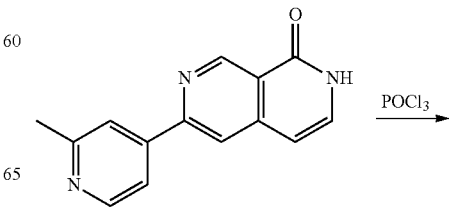

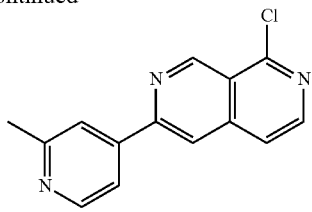

6-(2-methylpyridin-4-yl)-2,7-naphthyridin-1(2H)-one (150 mg, 0.63 mmol) was dissolved in POCl$_3$ (15.0 mL), the pressure tube was sealed and heated up to 160° C. for 4 h. After cooling down the reaction to RT, excessive POCl$_3$ was removed under vacuum. Crushed ice was slowly added into the mixture, and then added into NaHCO$_3$ to neutralize until pH ~7.5. Extracted the solution by EA three times, the combined organic layer was washed with brine, dried over Na$_2$SO$_4$, and concentrated under vacuum. The crude was purified by column with EA/Hexane (1:1) to get the compound 1-chloro-6-(2-methylpyridin-4-yl)-2,7-naphthyridine (yield ~55%). MS m/z 256.1 (M+1).

Step 3:

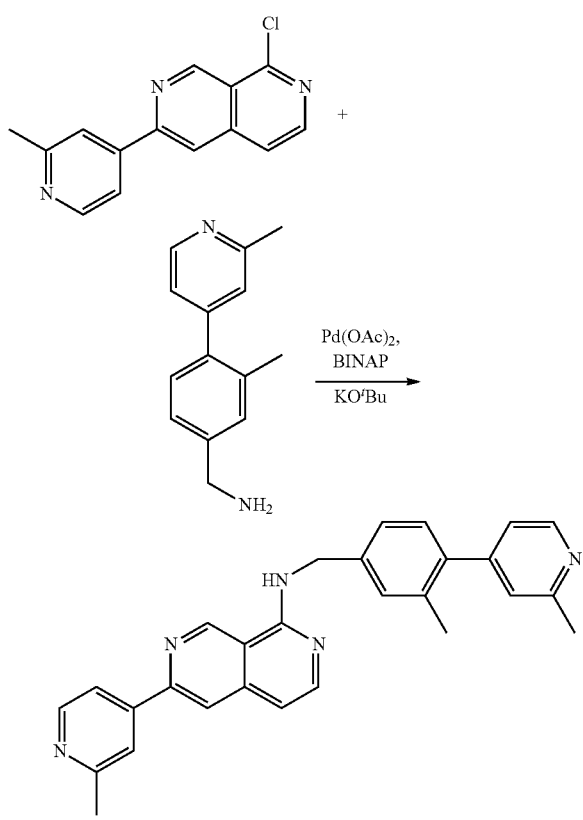

1-chloro-6-(2-methylpyridin-4-yl)-2,7-naphthyridine (10.00 mg, 0.039 mmol) and (3-methyl-4-(2-methylpyridin-4-yl)phenyl)methanamine (10.00 mg, 0.047 mmol) were dissolved in Toluene (1.0 mL). KO$^t$Bu (8.80 mg, 0.078 mmol), Pd(OAc)$_2$ (0.90 mg, 0.0039 mmol) and BINAP (4.90 mg, 0.0078 mmol) was added into the mixture under N$_2$. The reaction was heated up to 100° C. for overnight. After cooling down the reaction to RT, poured the mixture into the water, extracted by EA for three times. The combined organic layer was washed with brine, dried over Na$_2$SO$_4$, then concentrated under vacuum. The crude product was purified by prep-TLC by EA/Hexane (4:1) to get N-(3-methyl-4-(2-methylpyridin-4-yl)benzyl)-6-(2-methylpyridin-4-yl)-2,7-naphthyridin-1-amine (8.8 mg, yield ~52%). 1H NMR (300 MHz, CDCl3): δ2.31 (s, 3H), 2.63 (s, 3H), 2.70 (s, 3H), 4.91 (d, J=5.10 Hz, 2H), 5.88 (br, 1H), 7.00 (d, J=5.40 Hz, 1H), 7.08 (d, J=5.10 Hz, 1H), 7.12 (s, 1H), 7.22 (d, J=7.50 Hz, 1H), 7.36 (m, 2H), 7.77 (d, J=4.50 Hz, 1H), 7.88 (s, 1H), 7.98 (s, 1H), 8.24 (d, J=6.00 Hz, 1H), 8.53 (d, J=4.80 Hz, 1H), 8.64 (d, J=5.40 Hz, 1H), 9.31 (s, 1H). MS m/z 432.2 (M+1).

Example 3

Synthesis of 6-(3-fluorophenyl)-N-((6-(2-methylpyridin-4-yl)pyridin-3yl)methyl)isoquinolin-1-amine (Compound No. 3)

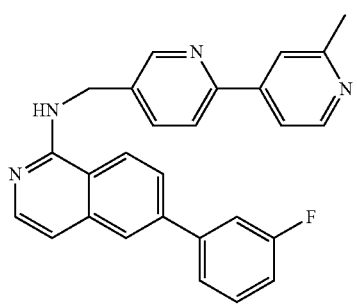 [SMILES: Cc1cc(-c2ccc(CNc3nccc4cc(-c5cccc(F)c5)ccc34)cn2)ccn1]

Step 1:

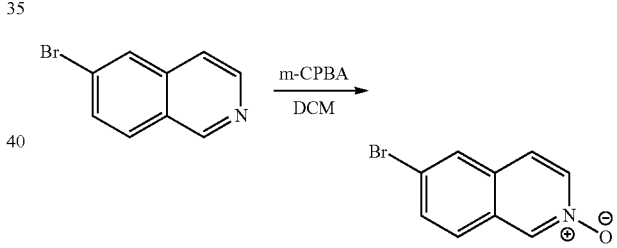

6-bromoisoquinoline (1.80 g, 8.66 mmol) was dissolved in DCM (40 mL), after cooling down the reaction to 0° C. m-CPBA (2.30 g, 1.3 eq, 77% max) was added slowly in small portion. The reaction was warmed up to RT to become a kind of white suspension. In 4 hours, 100 mL DCM was added into the solution, and washed with saturated Na$_2$CO$_3$ solution, water and brine. The separated organic layer was dried over Na$_2$SO$_4$ and removed under the vacuum to get the yellow solid N-oxide 6-bromoisoquinoline without further purification (1.82 g, yield ~93%).

Step 2:

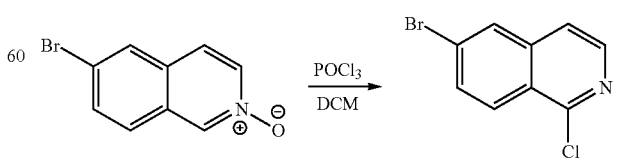

N-oxide 6-bromoisoquinoline (1.82 g, 8.12 mmol) was dissolved in dry DCM (80 mL), POCl$_3$ (1.12 ml, 1.5 eq) was added dropwise at RT. The reaction was heated to 45° C. for 2 hours. After cooling down the reaction to RT, DCM and excessive POCl₃ were removed under the vacuum. The crude was re-dissolved into 100 mL DCM and was washed by saturated Na₂CO₃, water and brine. The separated organic layer was dried over Na₂SO₄, and concentrated to give brown solid. The crude was purified by flash column using 2% MeOH in DCM to get the pale yellow solid 6-bromo-1-chloroisoquinoline (1.27 g, yield ~65%). MS m/z 242.0 (M+1).

Step 3:

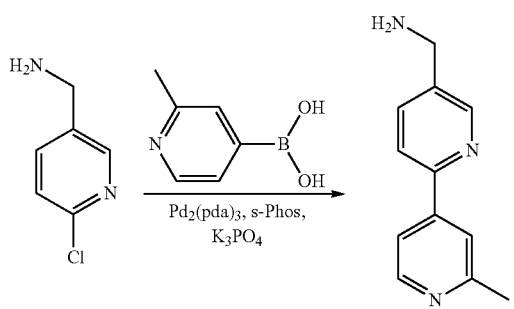

(6-chloropyridin-3-yl)methanamine (300 mg, 2.1 mmol) and 2-methylpyridin-4-ylboronic acid (345 mg, 2.52 mmol) were dissolved in a pressure tube with n-butanol (10 mL) and water (2 mL). K₃PO₄ (893 mg, 4.2 mmol), Pd₂(dba)₃ (96.3 mg, 0.105 mmol), and S-phos (86.4 mg, 0.21 mmol) were added under the nitrogen protection. The reaction was heated to 125° C. for 30 minutes and then cooled down to room temperature. The solution was pull in water and extracted by EA for three times. The combined organic layer was washed by brine and dried over Na₂SO₄, and concentrated under the vacuum. The crude was further purified by flash chromatography with 10% MeOH (containing ~2N NH₃) in DCM to get the pure (6-(2-methylpyridin-4-yl)pyridin-3-yl)methanamine (0.19 g, yield ~45%). MS m/z 200.1 (M+1).

Step 4:

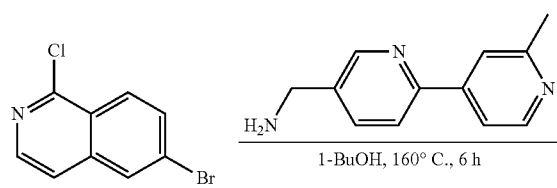

6-bromo-1-chloroisoquinoline (100 mg, 0.41 mmol) and (6-(2-methylpyridin-4-yl)pyridin-3-yl)methanamine (165 mg, 0.82 mmol) were dissolved in 0.5 mL n-BuOH in a sealed tube. The reaction was heat up to 160° C. for 6 h and cooled down to RT. The crude was purified by flash chromatography using 8% MeOH (containing ~2N NH3) in DCM to get the pure 6-bromo-N-((6-(2-methylpyridin-4-yl)pyridin-3-yl)methyl)isoquinolin-1-amine (116 mg, ~70%). MS m/z 405.2 (M+1).

Step 5:

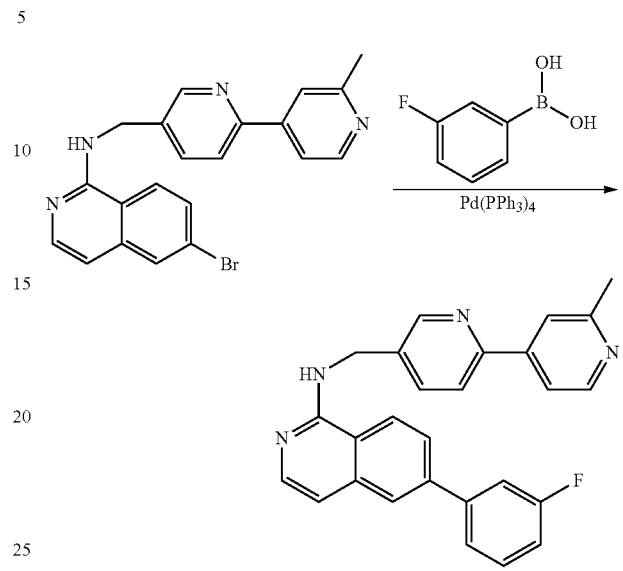

6-bromo-N-((6-(2-methylpyridin-4-yl)pyridin-3-yl)methyl)isoquinolin-1-amine (20 mg, 0.05 mmol), 3-fluorophenylboronic acid (10.5 mg, 0.075 mmol), Na₂CO₃ (21 mg, 0.2 mmol) and Tetrakis(triphenylphosphine)palladium (5.8 mg, 0.005 mmol) were added in a pressure tube. Dioxane/water (3:1, 2 mL) was added into the tube and heated to 125° C. for 10 minutes. After cooling down the reaction to RT, the solution was diluted by 50 mL water and extracted by EA for 3 times. The combined organic layer was dried over Na₂SO₄, and concentrated under the vacuum. The crude was further purified by flash chromatography with 10% MeOH (containing ~2N NH3) in DCM to get the pure 6-(3-fluorophenyl)-N-((6-(2-methylpyridin-4-yl)pyridin-3-yl)methyl)isoquinolin-1-amine (15.8 mg, ~75%). 1H NMR (400 MHz, CDCl3): δ2.71 (s, 3H), 5.00 (d, J=5.6 Hz, 2H), 7.32-7.38 (m, 2H), 7.59-7.65 (m, 1H), 7.75-7.83 (m, 3H), 8.10 (d, J=8.4 Hz, 1H), 8.21 (d, J=8.8 Hz, 1H), 8.27-8.31 (m, 2H), 8.39 (s, 2H), 8.72 (d, J=8.8 Hz, 1H), 8.79 (d, J=6.0 Hz, 1H), 8.91 (d, J=1.6 Hz, 1H), 10.02 (s, 1H). MS m/z 421.2 (M+1).

Example 4

Synthesis of N-(4-(2-methylpyridin-4-yl)benzyl)-2-(2-methylpyridin-4-yl)-1,6-naphthyridin-5-amine (Compound No. 4)

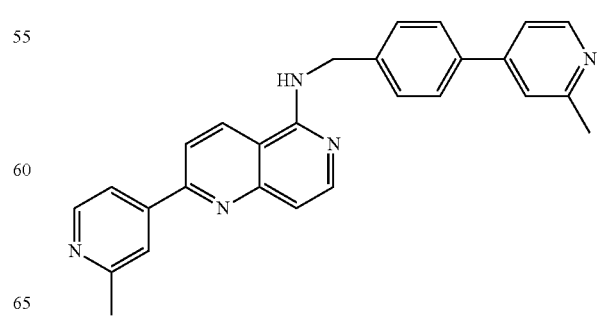

Step 1:

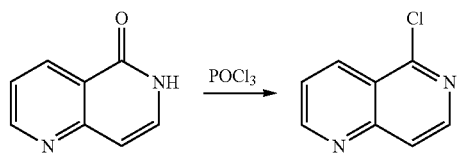

1,6-naphthyridin-5(6H)-one (2.9 g, 19.84 mmol) was dissolved in POCl$_3$ (40 mL) and heated up to 100° C. for 24 h. After cooling down the reaction to room temperature, the excessive POCl$_3$ was removed under the vacuum. Small amount crushed ice in saturated Na$_2$CO$_3$ solution was added slowly, and lots of bubbles and solid came out. The solid was filtered, and the solution was extracted by EA for 3 times. The combined organic layer was dried over Na$_2$SO$_4$, and concentrated under the vacuum. The combined solid was further dried under the vacuum to get 5-chloro-1,6-naphthyridine without further purification (2.6 g, yield ~80%). MS m/z 165.1 (M+1).

Step 2:

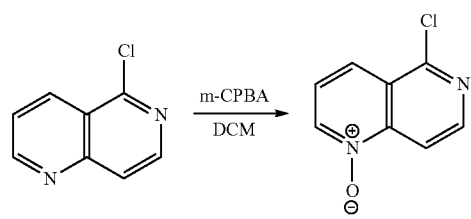 [SMILES: Clc1nccc2ncccc12 ; [O-][n+]1cccc2c(Cl)nccc21]

5-chloro-1,6-naphthyridine (1.5 g, 9.11 mmol) was dissolved in DCM (45 mL) and cooled down by ice bath, m-CPBA (3.7 g, 2 eq, 77% max) was added in small portion and slowly. The reaction was warmed up to RT and continued for 3 hours. 100 mL more DCM was added into the solution, and washed with saturated Na$_2$CO$_3$ solution, water and brine. The organic layer was dried over Na$_2$SO$_4$, and concentrated under the vacuum to get yellow solid N-oxide 5-chloro-1,6-naphthyridine without further purification (1.25 g, yield ~76%).

Step 3:

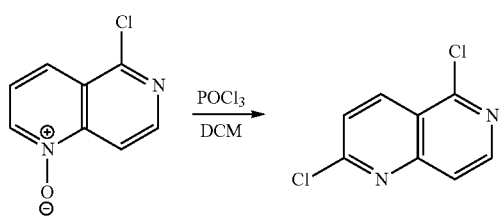

N-oxide 5-chloro-1,6-naphthyridine (1.2 g, 6.64 mmol) was dissolved in dry DCM (30 mL), Et3N (1.85 mL, 13.29 mmol) was added and followed by dropwise adding POCl$_3$ (0.93 mL, 9.97 mmol) in 5 mL dry DCM. The reaction was heated to 48° C. for 2 hours. 100 mL more DCM was added into the solution, and washed with saturated Na$_2$CO$_3$ solution, water and brine. The organic layer was dried over Na$_2$SO$_4$, and concentrated under the vacuum to get the yellow solid. The crude was further purified by silicon column using EA/Hexane (1:4) to get white solid 2,5-dichloro-1,6-naphthyridine (0.6 g, yield ~45%). MS m/z 199.0 (M+1)

Step 4:

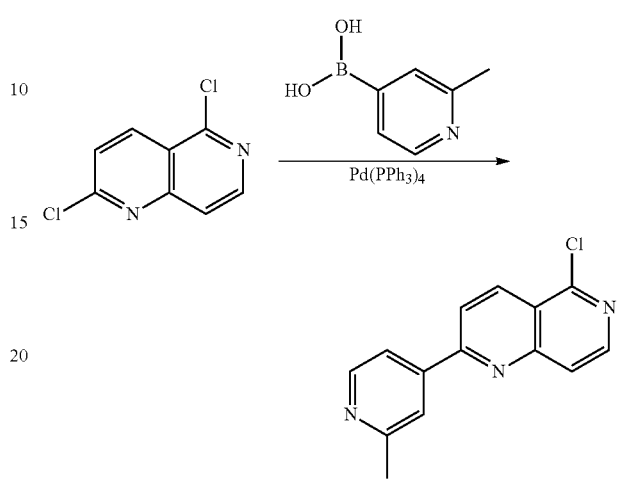

2,5-dichloro-1,6-naphthyridine (200 mg, 1.0 mmol), 2-methylpyridin-4-yl-4-boronic acid (137 mg, 1.0 mmol), Na$_2$CO$_3$ (424 mg, 4.0 mmol) and Tetrakis(triphenylphosphine)palladium (116 mg, 0.1 mmol) were added in a flask, dioxane 16 mL and water 4 mL were further added. The reaction was stirred very well and heated to 90° C. for 4 hours. After cooling down the reaction to RT, the solution was diluted by 100 mL water and extracted by EA for 3 times. The combined organic layer was dried over Na2SO4, and concentrated under the vacuum. The crude was further purified by flash chromatography with EA/Hexane (1:1) to get the solid 5-chloro-2-(2-methylpyridin-4-yl)-1,6-naphthyridine (143 mg, yield ~56%). MS m/z 256.1 (M+1)

Step 5:

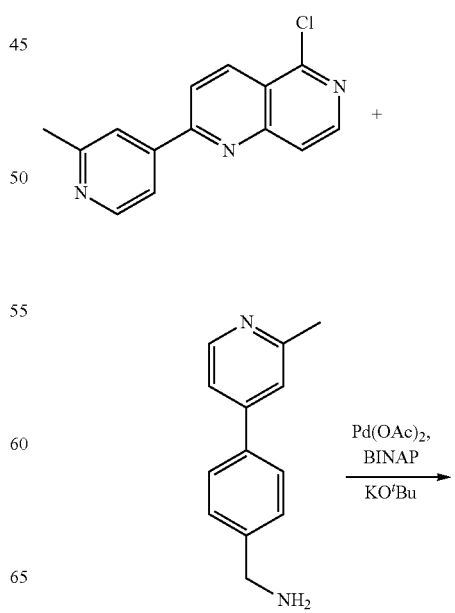

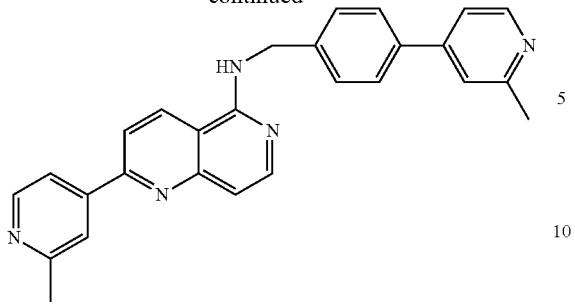

5-chloro-2-(2-methylpyridin-4-yl)-1,6-naphthyridine (20.00 mg, 0.078 mmol) and (4-(2-methylpyridin-4-yl)phenyl)methanamine (25 mg, 0.118 mmol) were dissolved in Toluene (2.0 mL). KO$^t$Bu (13.2 mg, 0.118 mmol), Pd(OAc)$_2$ (2.7 mg, 0.012 mmol) and BINAP (15.0 mg, 0.024 mmol) were added into the mixture under N$_2$. The reaction was heated up to 100° C. for overnight. After cooling down the reaction to RT, poured the mixture into the water, extracted by EA for three times. The combined organic layer was washed with brine, dried over Na$_2$SO$_4$, then concentrated under vacuum. The crude product was purified by prep-TLC by 8% MeOH in DCM to N-(4-(2-methylpyridin-4-yl)benzyl)-2-(2-methylpyridin-4-yl)-1,6-naphthyridin-5-amine (31 mg, yield ~61%). $^1$H NMR (400 MHz, DMSO-d6): δ 9.12 (d, J=8.8 Hz, 1H), 8.77-8.83 (m, 2H), 8.49 (d, J=8.4 Hz, 1H), 8.40 (s, 1H), 8.31 (d, J=6.4 Hz, 1H), 8.21 (s, 1H), 8.11 (d, J=5.6 Hz, 1H), 8.06 (d, J=6.4 Hz, 1H), 7.99 (d, J=8.4 Hz, 2H), 7.65 (d, J=8.4 Hz, 2H), 7.23 (d, J=6.4 Hz, 1H), 5.76 (s, 1H), 4.93 (d, J=5.6 Hz, 2H), 2.72 (s, 6H). MS m/z 432.2 [M+1]+.

Example 5

Synthesis of N-(4-(2-methylpyridin-4-yl)benzyl)-2-phenylpyrido[4,3-b]pyrazin-5-amine (Compound No. 5)

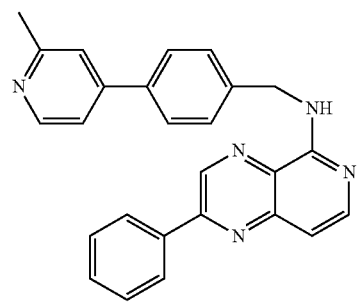 [SMILES: Cc1cc(-c2ccc(CNc3nccc4nc(-c5ccccc5)cnc34)cc2)ccn1]

Step 1:

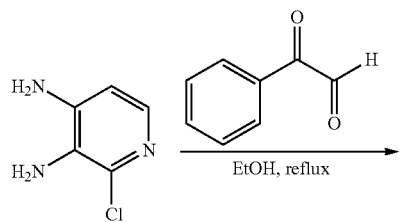

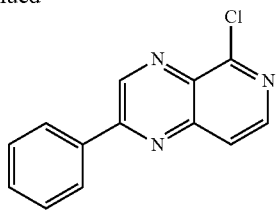

To 20 mL of ethanol was added phenyl gloyoxal monohydrate (940 mg, 6.99 mmol) and 2-chloro-3,4-diaminopyridine (1000 mg, 6.99 mmol). The mixture was refluxed for overnight. After cooling down the reaction, the crude precipitated product was filtered and washed with 15 mL ethanol and dried under vacuum to get 5-chloro-2-phenylpyrido[3,4-b]pyrazine without further purification (1.28 g, yield ~76%), MS m/z 241.0 (M+1); 1H NMR (300 MHz, DMSO-d6): δ 9.82 (s, 1H), 8.64 (d, J=6.0 Hz, 1H), 8.38-8.43 (m, 2H), 8.07 (d, J=6.0 Hz, 1H), 7.64-7.68 (m, 3H).

Step 2:

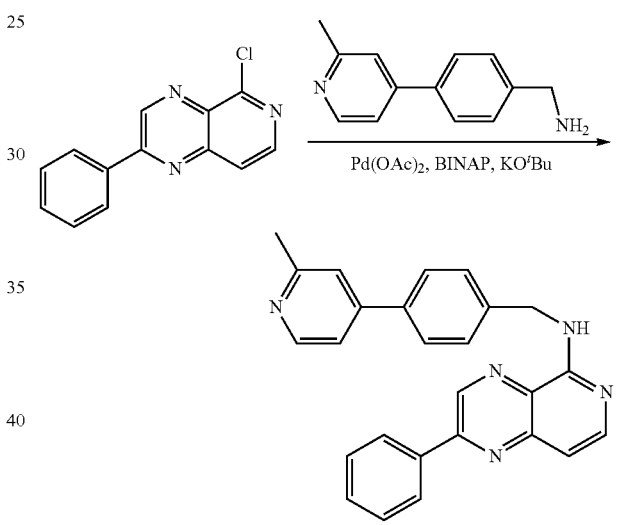

N-(4-(2-methylpyridin-4-yl)benzyl)-2-phenylpyrido[3,4-b]pyrazin-5-amine (50 mg, 0.21 mmol) and (4-(2-methylpyridin-4-yl)phenyl)methanamine (42 mg, 0.21 mmol) were dissolved in Toluene (4.0 mL). KO$^t$Bu (24 mg, 0.21 mmol), Pd(OAc)$_2$ (4.5 mg, 0.021 mmol) and BINAP (26.4 mg, 0.042 mmol) was added into the mixture under N$_2$. The reaction was heated up to 100° C. for overnight. After cooling down the reaction to RT, poured the mixture into the water, extracted by EA for three times. The combined organic layer was washed with brine, dried over Na$_2$SO$_4$, then concentrated under vacuum. The crude product was purified by flash chromatography using 7% MeOH in DCM to get N-(4-(2-methylpyridin-4-yl)benzyl)-2-phenylpyrido[4,3-b]pyrazin-5-amine (61 mg, yield ~72%). MS m/z=404.2 (M+1); $^1$H NMR (400 MHz, DMSO-d6) b 9.53 (s, 1H), 8.77 (d, J=6.4 Hz, 1H), 8.35-8.39 (m, 2H), 8.21 (s, 1H), 8.11 (d, J=6.0 Hz, 1H), 8.07 (d, J=6.4 Hz, 1H), 7.96 (d, J=8.4 Hz, 2H), 7.60-7.65 (m, 5H), 7.14 (d, J=6.0 Hz, 1H), 5.76 (s, 1H), 4.90 (d, J=6.4 Hz, 2H), 2.71 (s, 3H).

Example 6

WNT Pathway Reporter Gene Assay

Materials and Methods: NIH3T3 mouse fibroblast cells (American Type Culture Collection, Manassas, Va.) were transfected with a plasmid containing a luciferase gene driven by 5 copies of TCF elements. Stale cells selected with 1 µg/mL of Zeocin (Gibco/lnvitrogen, Carlsbad, Calif.) are cultured in Dulbecco's modified Eagle's medium (Invitrogen, Carlsbad, Calif.) supplemented with 10% FBS (Invitrogen), 50 unit/mL penicillin and 50 µg/mL of streptomycin (Invitrogen) at 37° C. with 5% CO2 in air atmosphere. Suspension HEK293 cells (ATCC) were transfected with a plasmid containing full-length human WNT-3a cDNA sequence driven by a CMV promoter, and stable cells were selected in FreeStyle 293 medium (Invitrogen) supplemented with 100 ug/mL G418.

The NIH3T3 TCF-Luc cells and 293 WNT3a cells were co-cultured in a 96-well plate with DMEM medium supplemented with 0.5% FBS. After 16 hours, the firefly luciferase activities are measured with the Steady-Glo™ Luciferase Assay System (Promega). The cells were treated with different concentrations of compounds of this invention during the co-culture. The IC50s were defined as the concentration when the compounds reduce the luminescence intensity by 50%. To normalize for cell quantity and viability, CellTiter Glo assay is next performed in a duplicate plate.

All compounds presented in the patent have $IC_{50}$<5 µM in WNT pathway reporter gene assay. Selective examples were listed in Table 2 below.

TABLE 2

| Compound No. | $IC_{50}$ (µM) |
|---|---|
| 1 | <0.003 |
| 2 | <0.003 |
| 3 | 0.010 |
| 4 | 0.005 |
| 5 | 0.070 |
| 9 | 0.010 |
| 14 | 0.003 |
| 16 | 0.015 |
| 20 | 0.050 |
| 22 | 0.005 |
| 23 | 0.020 |
| 28 | <0.003 |
| 33 | 0.050 |
| 35 | <0.003 |
| 37 | 0.020 |
| 39 | 0.070 |
| 47 | 1.25 |
| 50 | 0.035 |
| 61 | 0.005 |
| 63 | 0.005 |
| 68 | 0.025 |
| 69 | 0.015 |
| 70 | <0.003 |
| 75 | 0.005 |
| 84 | 0.015 |
| 96 | 0.001 |
| 97 | 0.001 |
| 104 | 0.005 |
| 108 | 0.008 |
| 110 | 0.002 |

Example 7

Mechanistic Studies of the WNT Pathway Inhibitors

Compounds that inhibited the TCF reporter gene activity induced by the co-cultured Wnt-3a cells in the primary assay were followed up in a mechanistic study to identify the point of action of the compounds. Two different of activators were assessed, one with purified recombinant Wnt-3a protein (StemRD Inc., Burlingame, Calif.), the other with a GSK-3b inhibitor 6-bromoindirubin-3'-oxime (StemRD Inc., Burlingame, Calif.).

Results of such mechanistic studies showed that some of the active compounds in this invention inhibit WNT pathway activation at a point before the WNT-3a interaction with the receptors, as they did not inhibit the TCF reporter gene activation by recombinant WNT-3a protein. The candidates of such action include, but are not limited to wntless/ evenness interrupted (Wls/Evi), porcupine (Porcn), and Vps35p. The direct target of the active compounds is most likely to be Porcn because transfection of Procn into WNT-3a expressing cells abolished the inhibitory effect of the compounds

Example 8

Effect of WNT Pathway Inhibitors on Cancer Cells

Compounds that inhibit Wnt secretion and intracellular signal transduction are expected to inhibit proliferation of cancer cells that depend on autocrine Wnt signaling. The effect of the Wnt pathway inhibitors on cell proliferation in 2-D culture, anchorage independent growth and apoptosis resistance in cell lines known to require Wnt autocrine signaling. Compounds are evaluated by using standard assays on the Wnt dependent cell lines known in the published literature: PA-1 (ovarian teratocarcinoma cancer), MDA-MB-157 (breast cancer), Saos-2 (osteosarcoma) and SNU1076 (head and neck squamous carcinoma). Effects of the inhibitors are seen in these cell lines, further confirming the activities expected for the compounds.

Example 9

Survey of Colorectal Tumors for Mutations

DNA isolated from tumor tissues of 30 colorectal cancer patients were sequenced for common oncogenes. Among the 30 tumors, 15 of them have no detectable mutations in their APC, CTNNB1 or axin-1 genes. Among the 15 tumors, 8 have mutations in k-ras or b-raf genes that are known to cooperate with Wnt pathway for oncogenesis. RNA from these 8 tumors were isolated and analyzed for expression of R spondin 3 by quantitative RT-PCR.

Expression of Rspo3 by quantitative RT-PCR: Data in the FIG. 1 show the level of Rspo3 RNA is higher in 8 tumor samples.

Quantitative PCR primers (SYBR method):

```
Rspo3
5'primer GGACTGAAACACGGGTCCGAGAAATAA (27 nt)

Rspo3
3' primer TCCTTTTTTTCCTCGTTCTCCCTTCTG (27 nt)

GAPDH
5'primer ATCTTCCAGGAGCGAGATCCCTCC (24 nt)

GAPDH
3'primer CCCCCCTGCAAATGAGCCCCA (21 nt)
```

Detection of PTPRK-RSPO3 gene fusion by RT-PCR: According to Seshagiri, et al. (Nature 488: 660-4, 2012), five out of 68 samples have gene fusions between PTPRK and Rspo3 genes. Four of the 5 samples are PTPRK exon1 fused with Rspo3 exon2 (fusion variant 1), and one sample is PTPRK exon7 fused with Rspo3 exon2 (fusion variant 2).

PCR primers for fusion variant 1 (PTPRK Exon1—Rspo3 Exon2):

```
5'primer:
AAACTCGGCATGGATACGACTGCG (24 nt) Tm = 69.3
GC % = 54.2

3'primer:
GCTTCATGCCAATTCTTTCCAGAGCA (26 nt) Tm = 69.8
GC % = 46.2
```

PCR primers for fusion variant 2 (PTPRK Exon7—Rspo3 Exon2):

```
5'primer:
TGCAGTCAATGCTCCAACTTACAAATTATG (30 nt) Tm = 68.1
GC % = 36.7

3'primer:
GCTTCATGCCAATTCTTTCCAGAGCA (26 nt) Tm = 69.8
GC % = 46.2
```

Figure 2:
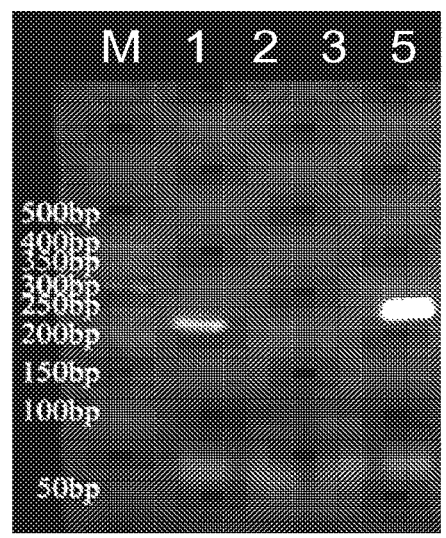
FIG. 2 depicts gene fusions between PTPRK and Rspo3 in colorectal tumor models detected by RT-PCR. Data show that Model #1 and #5 have products of gene fusion between PTPRK and Rspo3. Sequencing data show that Model #1 has fusion between exon 1 of PTPRK to exon 2 of Rspo3, and Model #5 has fusion between exon 7 of PTPRK and exon 2 of Rspo3.

FIG. 2 shows that gene fusions between PTPRK and Rspo3 are present in colorectal tumor models detected by RT-PCR. Sequencing data show that Model #1 has fusion between exon 1 of PTPRK to exon 2 of Rspo3, and #5 has fusion between exon 7 of PTPRK and exon 2 of Rspo3.

Example 10

Evaluation of Efficacy of CGX1321 in the Treatment of Patient-Derived Primary Colorectal Cancer Models Animal: Male BALB/c nude mice, 7-9 weeks old and weight 20-24 g.

Tumor Inoculation: Each mouse was inoculated subcutaneously on the right flank with tumor fragment (2×2×2 mm) for tumor development. Drug treatment started when mean tumor size reaches approximately 125 mm$^3$. Each group consisted of 8 mice. The test compound was administrated to the tumor-bearing mice according to predetermined regimen as shown in the following experiment design table.

Groups and Treatments: (for the two models of CRC011 and CRC141)

Group 1: Vehicle control; n=8; 0 mg/kg; p.o.; qd, 21 days
Group 2: CGX compound; n=8; 7.5 mg/kg; p.o.; qd, 21 days n: number of animals; dosing volume: adjust dosing volume based on body weight (10 μl/g).

Animal Housing: An acclimation period of approximately one week were allowed between animal receipt and tumor inoculation in order to accustom the animals to the laboratory environment. The nude mice will be maintained in a special pathogen-free environment and in micro isolator cages (5 mice per cage). All cages, bedding, and water will be sterilized before use. When working in the mouse room, the investigators will wear a lab coat and latex or vinyl gloves. Each cage will be clearly labeled with a cage card indicating study number, group, sex, and dose level. The cages with food and water will be changed twice a week. The targeted conditions for animal room environment and photoperiod will be as follows: Temperature: 22±3 OC; Humidity: 50±20%; Light cycle: 14 hours light and 10 hours dark Dietary Materials: All animals will have free access to a standard certified commercial laboratory diet. Maximum allowable concentrations of contaminants in the diet are controlled and routinely analyzed by the manufacturers. Autoclaved municipal tap water suitable for human consumption will be available to the animals ad libitum. It is considered that there are no known contaminants in the dietary materials that could influence the tumor growth.

Assignment to Groups: Before commence of treatment, all animals will be weighed and assigned to treatment groups using a randomization procedure. Since tumor size can affect the effectiveness of any given treatment, mice are randomized into groups based upon their tumor sizes. This ensures that each group has approximately the same mean tumor size and range of tumor size.

Observations: The protocol and any amendment(s) or procedures involving the care and use of animals was reviewed and approved by the Institutional Animal Care and Use Committee (IACUC) prior to conduct. During the study, the care and use of animals were conducted in accordance with the regulations of the Association for Assessment and Accreditation of Laboratory Animal Care (AAALAC). After inoculation, the animals were checked daily for morbidity and mortality. At the time of routine monitoring, the animals were checked for any effects of tumor growth on normal behavior such as mobility, food and water consumption, body weight gain/loss, eye/hair matting and any other abnormal effect. Death and observed clinical signs were recorded on the basis of the numbers of animals within each subset. Animals that are observed to be in a continuing deteriorating condition or bearing a tumor exceeding 3,000 mm$^3$ in size were euthanized prior to death or before reaching a comatose state.

Endpoints: The major endpoint is to see if the tumor growth can be delayed or mice can be cured. Body weight will be measured twice weekly, and tumor size will be measured two times per week in two dimensions using a caliper, and the volume will be expressed in mm$^3$ using the formula: V=0.5 a×b$^2$ where a and b are the long and short diameters of the tumor, respectively. The tumor size is then used for calculation of tumor growth inhibition (TGI). TGI, using the formula (1−T/C)×100%, is an indication of anti-tumor effectiveness; T and C are relative mean volumes of the tumors in treated and control groups, respectively, on a given day.

Statistical Analysis: The differences between the mean values of tumor size for comparing groups will be analyzed for significance using the ANOVA test. P<0.05 will be considered to be statistically significant.

Test Compound: CGX1321

Formulation: 20% v/v PEG 400+5% m/v Solutol+55% v/v D5W, sonicate 5 min.

Figure 5:
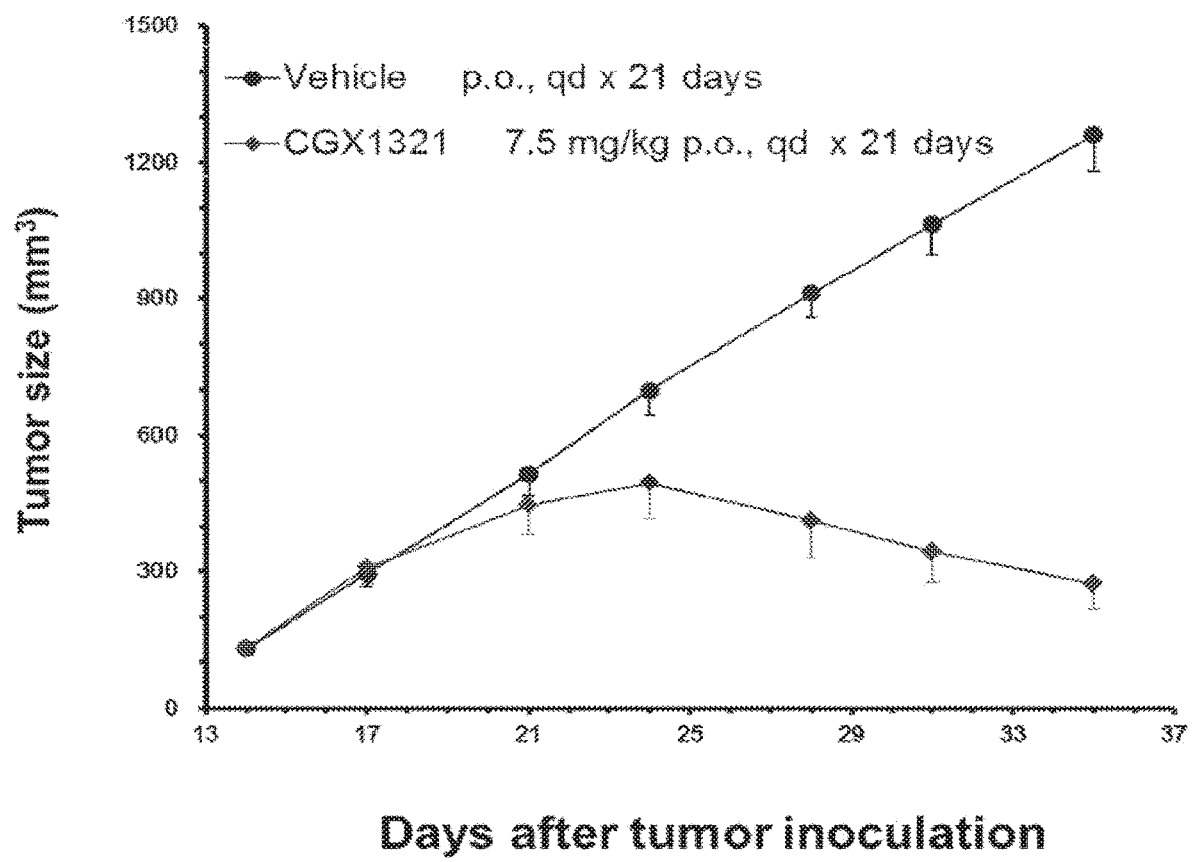
FIG. 5 depicts that patient-derived primary colorectal cancer tissue from Model #1 with gene fusion between exon 1 of PTPRK and exon 2 of Rspo3 was implanted in Balb/c nude mice. When the average tumor size reached approximately 125 $mm^3$, the test compound or vehicle control was administrated at 7.5 mg/kg orally, once daily. Tumor volume as measured every 3 or 4 days until 21 days after treatment.

The results are summarized in FIG. 5, which shows anti-tumor Effect of WNT Inhibitor Compound CGX1321 on Colorectal Cancer Model with Rspo3 fusion. Patient-derived primary colorectal cancer tissue from model #1 with gene fusion between exon 1 of PTPRK and exon 2 of Rspo3 was implanted in Balb/c nude mice. When the average tumor size reached approximately 125 mm$^3$, the test compound or vehicle control was administered at 7.5 mg/kg orally, once daily. Tumor volume as measured every 3 or 4 days until 21 days after treatment.

Example 11

Survey of Gastric, Liver and Esophageal Tumors for Mutations

RNA isolated from tumor tissues of gastric, liver and esophageal cancer patients were reverse-transcribed to cDNA and tested for the presence of an Rspo3-PTPRK or Rspo2-EIF3E fusion by RT-PCR.

PCR primers for Rspo3-PTPRK fusion variant 1 (PTPRK Exon1—Rspo3 Exon2):

```
5' primer:
AAACTCGGCATGGATACGACTGCG (24 nt) Tm = 69.3

3' primer:
GCTTCATGCCAATTCTTTCCAGAGCA (26 nt) Tm = 69.8
```

PCR primers for Rspo3-PTPRK fusion variant 2 (PTPRK Exon7—Rspo3 Exon2):

```
5'primer:
TGCAGTCAATGCTCCAACTTACAAATTATG (30 nt) Tm = 68.1

3'primer:
GCTTCATGCCAATTCTTTCCAGAGCA (26 nt) Tm = 69.8
```

PCR primers for Rspo2-EIF3E fusion variant 1 (EIF3E Exon1—Rspo2 Exon2):

```
5' primer:
ACTACTCGCATCGCGCACTTT (21 nt) Tm = 61.3

3' primer:
GGGAGGACTCAGAGGGAGAC (20 nt) Tm = 64.6
```

PCR primers for Rspo2-EIF3E fusion variant 2 (EIF3E Exon1—Rspo2 Exon3):

```
5' primer:
ACTACTCGCATCGCGCACTTT (21 nt) Tm = 61.3

3' primer:
TGCAGGCACTCTCCATACTG (20 nt) Tm = 60.5
```

FIG. 6 depicts gene fusions between PTPRK and Rspo3 in gastric and liver tumor models detected by RT-PCR. Data show that gastric tumor model # G10 and liver tumor model # L2 and # L8 have products of gene fusion between PTPRK and Rspo3. Sequencing data show that these tumors have fusion between exon 1 of PTPRK to exon 2 of Rspo3.

FIG. 7 depicts gene fusions between PTPRK and Rspo3 in an esophageal tumor model detected by RT-PCR. Data show that esophageal tumor model # E7 has product of gene fusion between PTPRK and Rspo3. Sequencing data show that this tumor has fusion between exon 7 of PTPRK and exon 2 of Rspo3.

FIG. 8 depicts gene fusions between EIF3E and Rspo2 in liver tumor model detected by RT-PCR. Data show that liver tumor model # L7 has a product of gene fusion between exon 1 of EIF3E and exon 2 of Rspo2.

FIG. 9 depicts gene fusions between EIF3E and Rspo2 in gastric and liver tumor models detected by RT-PCR. Data show that gastric tumor models # G6 and # G13 and liver tumor model # L6 have products of gene fusion between exon 1 of EIF3E and exon 3 of Rspo2.

Example 12

Figure 10:
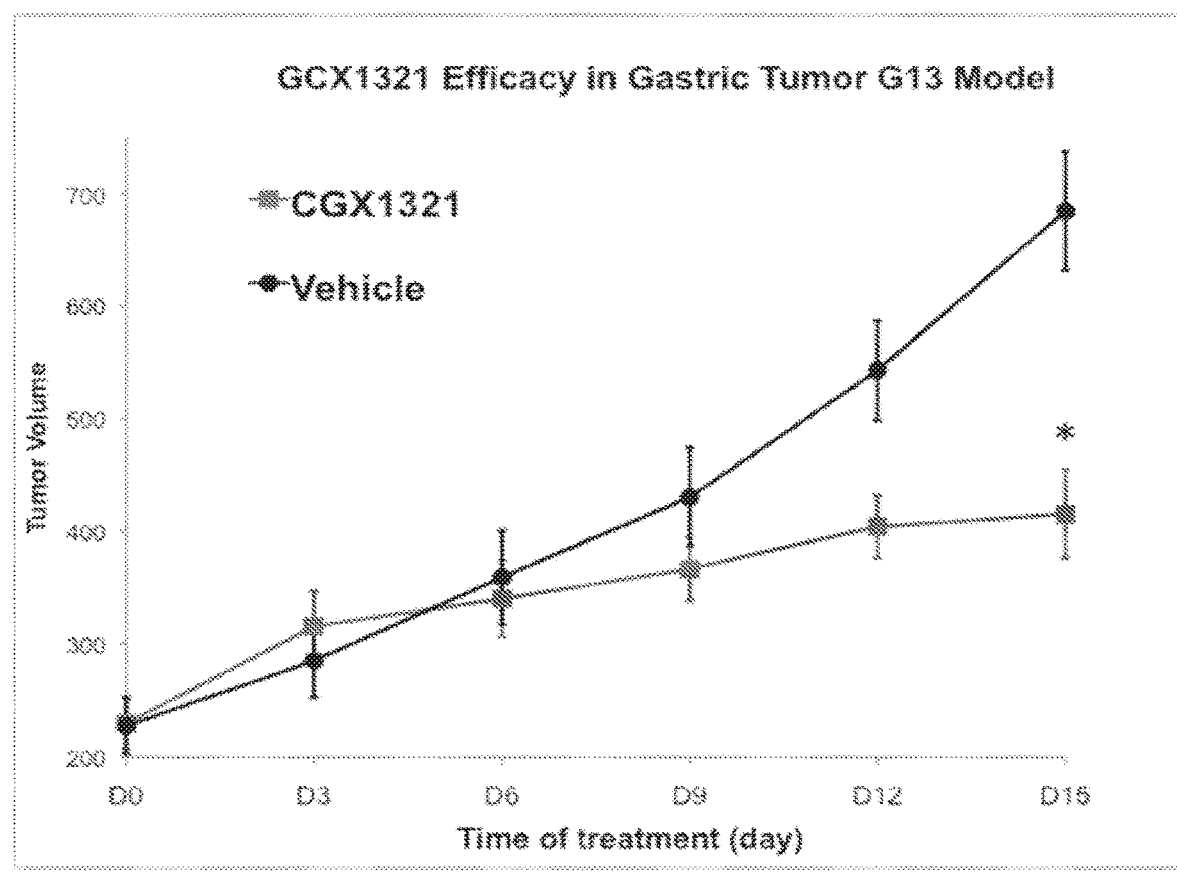
FIG. 10 depicts that patient-derived primary gastric tumor model # G13 with gene fusion between exon 1 of EIF3E and exon 2 of Rspo2 was implanted in Balb/c nude mice. When the average tumor size reached approximately 225 mm$^3$, the test compound CGX1321 or vehicle control was administrated at 20 mg/kg orally, once every two days (qod). Tumor volume as measured every 3 or 4 days until 15 days after treatment.

Evaluation of Efficacy of CGX1321 in the Treatment of Patient-Derived Primary Gastric Cancer Model FIG. 10 depicts that patient-derived primary gastric tumor model # G13 with gene fusion between exon 1 of EIF3E and exon 2 of Rspo2 was implanted in Balb/c nude mice. When the average tumor size reached approximately 225 mm$^3$, the test compound CGX1321 or vehicle control was administrated at 20 mg/kg orally, once every two days (qod). Tumor volume as measured every 3 or 4 days until 15 days after treatment.

The invention claimed is:

1. A method for treating cancer characterized by overexpression of an R-spondin in a subject that has been diagnosed as having overexpression of an R-spondin and has been diagnosed with the cancer being treated, comprising:
administering to the subject a pharmaceutical composition comprising a therapeutically effective amount of a WNT signaling inhibitor, wherein the WNT signaling inhibitor is a small organic molecule, and wherein the WNT signaling inhibitor inhibits porcupine (PORCN).

2. The method of claim 1, wherein the pharmaceutical composition is for topical application and is an aqueous solution, an ointment, a cream or a gel.

3. The method of claim 2, wherein the therapeutically effective amount of the WNT signaling inhibitor is about 0.03 to 2.5 mg/kg of body weight at daily dosages.

4. The method of claim 3, wherein the therapeutically effective amount of the WNT signaling inhibitor is about 0.5 mg to about 100 mg for human.

5. The method of claim 1, wherein the pharmaceutical composition is administered enterally, orally, parenterally, topically or in a nasal or suppository form.

6. The method of claim 5, wherein the pharmaceutical composition is a tablet or a gelatin capsule when administered orally.

7. The method of claim 5, wherein the pharmaceutical composition comprises at least one pharmaceutically acceptable carrier or diluent.

8. The method of claim 1, wherein the cancer is colorectal cancer, gastric cancer, liver cancer, or esophageal cancer.

9. The method of claim 1, wherein the overexpression of R-spondin is detected by an immunoassay using a R-spondin fusion-specific reagent.

10. The method of claim 1, wherein the overexpression of R-spondin is detected by RT-PCR, RT-PCR combined with Real-time PCR, digital PCR, DNA array, high throughput sequencing, or in situ hybridization.

11. The method of claim 1, wherein overexpression of the R-spondin fusion is detected using a circulating tumor cell.

* * * * *

SEQUENCE LISTING

```
<160> NUMBER OF SEQ ID NOS: 22

<210> SEQ ID NO 1
<211> LENGTH: 27
<212> TYPE: DNA
<213> ORGANISM: Artificial Sequence
<220> FEATURE:
<223> OTHER INFORMATION: Rspo3 5' primer

<400> SEQUENCE: 1
ggactgaaac acgggtccga gaaataa                                        27

<210> SEQ ID NO 2
<211> LENGTH: 27
<212> TYPE: DNA
<213> ORGANISM: Artificial Sequence
<220> FEATURE:
<223> OTHER INFORMATION: Rspo3 3' primer

<400> SEQUENCE: 2
tccttttttt cctcgttctc ccttctg                                        27

<210> SEQ ID NO 3
<211> LENGTH: 24
<212> TYPE: DNA
<213> ORGANISM: Artificial Sequence
<220> FEATURE:
<223> OTHER INFORMATION: GAPDH 5' primer

<400> SEQUENCE: 3
```

```
atcttccagg agcgagatcc ctcc                                          24

<210> SEQ ID NO 4
<211> LENGTH: 21
<212> TYPE: DNA
<213> ORGANISM: Artificial Sequence
<220> FEATURE:
<223> OTHER INFORMATION: GAPDH 3' primer

<400> SEQUENCE: 4 ccccctgca aatgagcccc a                                              21

<210> SEQ ID NO 5
<211> LENGTH: 24
<212> TYPE: DNA
<213> ORGANISM: Artificial Sequence
<220> FEATURE:
<223> OTHER INFORMATION: 5' primer - fusion variant 1 (PTPRK Exon1 -
      Rspo3 Exon2)

<400> SEQUENCE: 5
aaactcggca tggatacgac tgcg                                          24

<210> SEQ ID NO 6
<211> LENGTH: 26
<212> TYPE: DNA
<213> ORGANISM: Artificial Sequence
<220> FEATURE:
<223> OTHER INFORMATION: 3' primer - fusion variant 1 (PTPRK Exon1 -
      Rspo3 Exon2)

<400> SEQUENCE: 6
gcttcatgcc aattctttcc agagca                                        26

<210> SEQ ID NO 7
<211> LENGTH: 30
<212> TYPE: DNA
<213> ORGANISM: Artificial Sequence
<220> FEATURE:
<223> OTHER INFORMATION: 5' primer - fusion variant 2 (PTPRK Exon7 -
      Rspo3 Exon2)

<400> SEQUENCE: 7
tgcagtcaat gctccaactt acaaattatg                                    30

<210> SEQ ID NO 8
<211> LENGTH: 26
<212> TYPE: DNA
<213> ORGANISM: Artificial Sequence
<220> FEATURE:
<223> OTHER INFORMATION: 3' primer - fusion variant 2 (PTPRK Exon7 -
      Rspo3 Exon2)

<400> SEQUENCE: 8
gcttcatgcc aattctttcc agagca                                        26

<210> SEQ ID NO 9
<211> LENGTH: 24
<212> TYPE: DNA
<213> ORGANISM: Artificial Sequence
<220> FEATURE:
<223> OTHER INFORMATION: 5' primer - Rspo3- PTPRK fusion variant 1
      (PTPRK Exon1 - Rspo3 Exon2)

<400> SEQUENCE: 9
aaactcggca tggatacgac tgcg                                          24
```

<210> SEQ ID NO 10
<211> LENGTH: 26
<212> TYPE: DNA
<213> ORGANISM: Artificial Sequence
<220> FEATURE:
<223> OTHER INFORMATION: 3' primer - Rspo3- PTPRK fusion variant 1
      (PTPRK Exon1 - Rspo3 Exon2)

<400> SEQUENCE: 10
gcttcatgcc aattctttcc agagca                                        26

<210> SEQ ID NO 11
<211> LENGTH: 30
<212> TYPE: DNA
<213> ORGANISM: Artificial Sequence
<220> FEATURE:
<223> OTHER INFORMATION: 5' primer - Rspo3- PTPRK fusion variant 2
      (PTPRK Exon7 - Rspo3 Exon2)

<400> SEQUENCE: 11
tgcagtcaat gctccaactt acaaattatg                                    30

<210> SEQ ID NO 12
<211> LENGTH: 26
<212> TYPE: DNA
<213> ORGANISM: Artificial Sequence
<220> FEATURE:
<223> OTHER INFORMATION: 3' primer - Rspo3- PTPRK fusion variant 2
      (PTPRK Exon7 - Rspo3 Exon2)

<400> SEQUENCE: 12
gcttcatgcc aattctttcc agagca                                        26

<210> SEQ ID NO 13
<211> LENGTH: 21
<212> TYPE: DNA
<213> ORGANISM: Artificial Sequence
<220> FEATURE:
<223> OTHER INFORMATION: 5' primer - Rspo2- EIF3E fusion variant 1
      (EIF3E Exon1 - Rspo2 Exon2)

<400> SEQUENCE: 13
actactcgca tcgcgcactt t                                             21

<210> SEQ ID NO 14
<211> LENGTH: 20
<212> TYPE: DNA
<213> ORGANISM: Artificial Sequence
<220> FEATURE:
<223> OTHER INFORMATION: 3' primer - Rspo2- EIF3E fusion variant 1
      (EIF3E Exon1 - Rspo2 Exon2)

<400> SEQUENCE: 14
gggaggactc agagggagac                                               20

<210> SEQ ID NO 15
<211> LENGTH: 21
<212> TYPE: DNA
<213> ORGANISM: Artificial Sequence
<220> FEATURE:
<223> OTHER INFORMATION: 5' primer - Rspo2- EIF3E fusion variant 2
      (EIF3E Exon1 - Rspo2 Exon3)

<400> SEQUENCE: 15
actactcgca tcgcgcactt t                                             21

```
<210> SEQ ID NO 16
<211> LENGTH: 20
<212> TYPE: DNA
<213> ORGANISM: Artificial Sequence
<220> FEATURE:
<223> OTHER INFORMATION: 3' primer - Rspo2- EIF3E fusion variant 2
      (EIF3E Exon1 - Rspo2 Exon3)

<400> SEQUENCE: 16
tgcaggcact ctccatactg                                                 20

<210> SEQ ID NO 17
<211> LENGTH: 226
<212> TYPE: DNA
<213> ORGANISM: Artificial Sequence
<220> FEATURE:
<223> OTHER INFORMATION: PCR product of Colorectal Tumor Model #1 with
      PTPRK (e1) - Rspo3 (e2) fusion

<400> SEQUENCE: 17
aaactcggca tggatacgac tgcggcggcg gcgctgcctg cttttgtggc gctcttgctc      60
ctctctcctt ggcctctcct gggatcggcc caaggccagt tctccgcagt gcatcctaac     120
gttagtcaag gctgccaagg aggctgtgca acatgctcag attacaatgg atgtttgtca     180
tgtaagccca gactattttt tgctctggaa agaattggca tgaagc                    226

<210> SEQ ID NO 18
<211> LENGTH: 257
<212> TYPE: DNA
<213> ORGANISM: Artificial Sequence
<220> FEATURE:
<223> OTHER INFORMATION: PCR Product of Colorectal Tumor Model #5 with
      PTPRK (e7) -Rspo3 (e2) fusion

<400> SEQUENCE: 18
tgcagtcaat gctccaactt acaaattatg gcatttagat ccagataccg aatatgagat      60
ccgagttcta cttacaagac ctggtgaagg tggaacgggg ctcccaggac ctccactaat     120
caccagaaca aaatgtgcag tgcatcctaa cgttagtcaa ggctgccaag gaggctgtgc     180
aacatgctca gattacaatg gatgtttgtc atgtaagccc agactatttt ttgctctgga     240
aagaattggc atgaagc                                                    257

<210> SEQ ID NO 19
<211> LENGTH: 226
<212> TYPE: DNA
<213> ORGANISM: Artificial Sequence
<220> FEATURE:
<223> OTHER INFORMATION: RT-PCR product of gastric tumor model #G10 and
      liver tumor model #L2 and #L8 with gene fusion between PTPRK and
      Rspo3.

<400> SEQUENCE: 19
aaactcggca tggatacgac tgcggcggcg gcgctgcctg cttttgtggc gctcttgctc      60
ctctctcctt ggcctctcct gggatcggcc caaggccagt tctccgcagt gcatcctaac     120
gttagtcaag gctgccaagg aggctgtgca acatgctcag attacaatgg atgtttgtca     180
tgtaagccca gactattttt tgctctggaa agaattggca tgaagc                    226

<210> SEQ ID NO 20
<211> LENGTH: 257
<212> TYPE: DNA
<213> ORGANISM: Artificial Sequence
<220> FEATURE:
```

```
<223> OTHER INFORMATION: RT-PCR product of esophageal tumor model #E7
      with gene fusion between PTPRK and Rspo3.

<400> SEQUENCE: 20
tgcagtcaat gctccaactt acaaattatg gcatttagat ccagataccg aatatgagat      60
ccgagttcta cttacaagac ctggtgaagg tggaacgggg ctcccaggac ctccactaat     120
caccagaaca aaatgtgcag tgcatcctaa cgttagtcaa ggctgccaag gaggctgtgc     180
aacatgctca gattacaatg gatgtttgtc atgtaagccc agactatttt ttgctctgga     240
aagaattggc atgaagc                                                    257

<210> SEQ ID NO 21
<211> LENGTH: 155
<212> TYPE: DNA
<213> ORGANISM: Artificial Sequence
<220> FEATURE:
<223> OTHER INFORMATION: RT-PCR product of liver tumor model #L7 with
      gene fusion between exon 1 of EIF3E and exon 2 of Rspo2.

<400> SEQUENCE: 21
actactcgca tcgcgcactt tttggatcgg catctagtct ttccgcttct tgaatttctc      60
tctgtaaagg aggttcgtgg cggagagatg ctgatcgcgc tgaactgacc ggtgcggccc     120
gggggtgagt ggcgagtctc cctctgagtc ctccc                                155

<210> SEQ ID NO 22
<211> LENGTH: 205
<212> TYPE: DNA
<213> ORGANISM: Artificial Sequence
<220> FEATURE:
<223> OTHER INFORMATION: RT-PCR product of gastric tumor models #G6 and
      #G13 and liver tumor model #L6 with gene fusion between exon 1 of
      EIF3E and exon 3 of Rspo2.

<400> SEQUENCE: 22
actactcgca tcgcgcactt tttggatcgg catctagtct ttccgcttct tgaatttctc      60
tctgtaaagg agctagttat gtatcaaatc ccatttgcaa gggttgtttg tcttgttcaa     120
aggacaatgg gtgtagccga tgtcaacaga agttgttctt cttccttcga agagaaggga     180
tgcgccagta tggagagtgc ctgca                                           205
```